(12) United States Patent
Curtiss et al.

(10) Patent No.: US 9,303,264 B2
(45) Date of Patent: Apr. 5, 2016

(54) PHOTOSYNTHETIC MICROORGANISMS EXPRESSING THERMOSTABLE LIPASE

(71) Applicants: Roy Curtiss, Paradise Valley, AZ (US); Xinyao Liu, Jeddah-Thuwal (SA)

(72) Inventors: Roy Curtiss, Paradise Valley, AZ (US); Xinyao Liu, Jeddah-Thuwal (SA)

(73) Assignee: The Arizona Board of Regents for and on Behalf of Arizona State University, Tempe, AZ (US)

( * ) Notice: Subject to any disclaimer, the term of this patent is extended or adjusted under 35 U.S.C. 154(b) by 0 days.

(21) Appl. No.: 13/898,241

(22) Filed: May 20, 2013

(65) Prior Publication Data

US 2013/0316458 A1 Nov. 28, 2013

Related U.S. Application Data

(60) Provisional application No. 61/648,920, filed on May 18, 2012.

(51) Int. Cl.
*G01N 33/569* (2006.01)
*C12N 15/74* (2006.01)
*C12N 9/18* (2006.01)
*C12N 1/06* (2006.01)
*C12P 5/02* (2006.01)

(52) U.S. Cl.
CPC *C12N 15/74* (2013.01); *C12N 1/06* (2013.01); *C12N 9/18* (2013.01); *C12P 5/02* (2013.01)

(58) Field of Classification Search
None
See application file for complete search history.

(56) References Cited

U.S. PATENT DOCUMENTS

| | | | |
|---|---|---|---|
| 4,190,495 A | 2/1980 | Curtiss, III | |
| 4,888,170 A | 12/1989 | Curtiss, III | |
| 4,968,619 A | 11/1990 | Curtiss, III | |
| 5,210,035 A | 5/1993 | Stocker | |
| 5,294,441 A | 3/1994 | Curtiss, III | |
| 5,387,744 A | 2/1995 | Curtiss, III | |
| 5,389,368 A | 2/1995 | Gurtiss, III | |
| 5,424,065 A | 6/1995 | Curtiss, III | |
| 5,468,485 A | 11/1995 | Curtiss, III | |
| 5,536,658 A | 7/1996 | Shotts, Jr. et al. | |
| 5,654,184 A | 8/1997 | Curtiss, III | |
| 5,656,488 A | 8/1997 | Curtiss, III | |
| 5,672,345 A | 9/1997 | Curtiss, III | |
| 5,679,880 A | 10/1997 | Curtiss, III | |
| 5,686,079 A | 11/1997 | Curtiss, III | |
| 5,817,317 A | 10/1998 | Titball | |
| 5,827,705 A | 10/1998 | Dean | |
| 5,840,483 A | 11/1998 | Curtiss, III | |
| 5,855,879 A | 1/1999 | Curtiss, III | |
| 5,855,880 A | 1/1999 | Curtiss, III | |
| 5,961,983 A | 10/1999 | Brey et al. | |
| 6,024,961 A | 2/2000 | Curtiss, III | |
| 6,180,614 B1 | 1/2001 | Davis | |
| 6,248,329 B1 | 6/2001 | Chandrashekar et al. | |
| 6,350,454 B1 | 2/2002 | Thune | |
| 6,383,496 B1 | 5/2002 | Curtiss, III | |
| 6,399,074 B1 | 6/2002 | Roland | |
| 6,403,094 B1 | 6/2002 | Titball | |
| 6,610,529 B1 | 8/2003 | Curtiss, III | |
| 6,780,405 B1 | 8/2004 | Curtiss, III | |
| 6,872,547 B1 | 3/2005 | Curtiss, III | |
| 6,969,513 B2 | 11/2005 | Galen | |
| 7,083,794 B2 | 8/2006 | Curtiss, III | |
| 7,195,757 B2 | 3/2007 | Curtiss, III | |
| 7,205,125 B2 | 4/2007 | Castillo | |
| 7,341,860 B2 | 3/2008 | Curtiss, III | |
| 7,871,604 B1 | 1/2011 | Curtiss, III | |
| 7,968,101 B2 | 6/2011 | Kawaoka | |
| 8,133,493 B2 | 3/2012 | Curtiss, III | |
| 8,445,254 B2 | 5/2013 | Curtiss, III et al. | |
| 8,465,755 B2 | 6/2013 | Curtiss, III et al. | |
| 2003/0031683 A1 | 2/2003 | Curtiss, III | |
| 2003/0175772 A1 | 9/2003 | Wang | |
| 2004/0077556 A1 | 4/2004 | Chinery | |
| 2004/0101531 A1 | 5/2004 | Curtiss, III | |
| 2004/0120962 A1 | 6/2004 | Curtiss, III | |
| 2004/0137003 A1 | 7/2004 | Curtiss, III | |
| 2004/0203039 A1 | 10/2004 | Hensel | |
| 2005/0036987 A1 | 2/2005 | Pawelek et al. | |
| 2005/0106175 A1 | 5/2005 | Montaines | |
| 2005/0106176 A1 | 5/2005 | Curtiss, III | |
| 2005/0118193 A1 | 6/2005 | Andino-Pavlovsky et al. | |
| 2006/0140975 A1 | 6/2006 | Curtiss, III | |
| 2006/0171917 A1 | 8/2006 | Campbell | |
| 2006/0206961 A1 | 9/2006 | Cirpus | |
| 2006/0233829 A1 | 10/2006 | Curtiss, III | |
| 2006/0234346 A1 | 10/2006 | Retallack | |
| 2006/0275255 A1 | 12/2006 | Gudkov | |
| 2007/0025981 A1 | 2/2007 | Szalay | |

(Continued)

FOREIGN PATENT DOCUMENTS

EP 0315682 B1 12/1993
EP 0381706 B1 4/1995

(Continued)

OTHER PUBLICATIONS

Yu et al. ( Journal of Molecular Catalysis B: Enzymatic vol. 66, pp. 81-89, 2010).*
Allan Svenden ( Biochimica et Biophysica Acta vol. 1543, pp. 223-238, 2000).*
He et al. ( Enzyme and Microbial Technology vol. 43, pp. 13-18 , 2008).*
Liu et al. (PNAS vol. 108, No. 17, pp. 6905-6908) Apr. 26, 2011.*
Liu et al. (PNAS vol. 106, No. 51, pp. 21550-2'554) Dec. 22, 2009.*
Royter et al. Extremophiles vol. 13 pp. 769-783, 2009.*
Svendsen, Biochimica et Biophysica Acta, vol. 1543, pp. 223-238, 2000.*
U.S. Appl. No. 08/761,769, Office Action dated Sep. 25, 2001.

(Continued)

*Primary Examiner* — J. Hines
*Assistant Examiner* — Khatol Shahnan Shah
(74) *Attorney, Agent, or Firm* — Polsinelli PC

(57) ABSTRACT

The present invention encompasses a photosynthetic microorganism that produces biofuels and biofuel precursors.

10 Claims, 14 Drawing Sheets
(3 of 14 Drawing Sheet(s) Filed in Color)

(56) References Cited

U.S. PATENT DOCUMENTS

| | | | |
|---|---|---|---|
| 2008/0096809 | A1 | 4/2008 | Shai |
| 2008/0248066 | A1 | 10/2008 | Dubensky, Jr. |
| 2009/0175829 | A1 | 7/2009 | Forbes et al. |
| 2010/0124558 | A1 | 5/2010 | Curtiss et al. |
| 2010/0154293 | A1* | 6/2010 | Hom et al. ............... 44/385 |
| 2010/0255022 | A1 | 10/2010 | Prescott et al. |
| 2010/0285592 | A1 | 11/2010 | Curtiss et al. |
| 2010/0317084 | A1 | 12/2010 | Curtiss, III |
| 2011/0033501 | A1 | 2/2011 | Curtiss, III et al. |
| 2011/0256181 | A1 | 10/2011 | Curtiss et al. |
| 2011/0287052 | A1 | 11/2011 | Curtiss, III et al. |
| 2012/0087946 | A1 | 4/2012 | Curtiss, III |
| 2013/0004537 | A1 | 1/2013 | Curtiss, III et al. |
| 2013/0171190 | A1 | 7/2013 | Curtiss, III et al. |

FOREIGN PATENT DOCUMENTS

| | | | |
|---|---|---|---|
| EP | 0465560 | B1 | 6/1996 |
| EP | 0500699 | B1 | 6/1998 |
| EP | 0558631 | B1 | 3/1999 |
| EP | 0433372 | B1 | 6/2002 |
| EP | 1030690 | B1 | 7/2002 |
| EP | 0556333 | B1 | 3/2003 |
| EP | 1326960 | B1 | 12/2004 |
| EP | 0832255 | B1 | 12/2005 |
| EP | 1537214 | B1 | 3/2006 |
| EP | 1292687 | B1 | 8/2006 |
| WO | 88/09669 | A1 | 12/1988 |
| WO | 89/03427 | A1 | 4/1989 |
| WO | 90/02484 | A1 | 3/1990 |
| WO | 90/11687 | A1 | 10/1990 |
| WO | 90/11688 | A1 | 10/1990 |
| WO | 90/12086 | A1 | 10/1990 |
| WO | 91/06317 | A1 | 5/1991 |
| WO | 92/08486 | A1 | 5/1992 |
| WO | 92/09684 | A1 | 6/1992 |
| WO | 93/04202 | A1 | 3/1993 |
| WO | 94/24291 | A2 | 10/1994 |
| WO | 94/24291 | A3 | 12/1994 |
| WO | 96/40947 | A1 | 12/1996 |
| WO | 99/25387 | A1 | 5/1999 |
| WO | 01/83785 | A2 | 11/2001 |
| WO | 02/30457 | A2 | 4/2002 |
| WO | 01/83785 | A3 | 6/2002 |
| WO | 02/059292 | A2 | 8/2002 |
| WO | 02/030457 | A3 | 1/2003 |
| WO | 02/030457 | A3 | 7/2003 |
| WO | 02/059292 | A3 | 7/2003 |
| WO | 03/079792 | A1 | 10/2003 |
| WO | 03/096812 | A1 | 11/2003 |
| WO | 2004/020643 | A2 | 3/2004 |
| WO | 2004/020643 | A3 | 4/2004 |
| WO | 2005/001069 | A1 | 1/2005 |
| WO | 2012087483 | A1 | 6/2008 |
| WO | 2008/141226 | A2 | 11/2008 |
| WO | 2009/025888 | A2 | 2/2009 |
| WO | 2009/046449 | A1 | 4/2009 |
| WO | 2009/046451 | A1 | 4/2009 |
| WO | 2010/045620 | A1 | 4/2010 |
| WO | 2010/078584 | A1 | 8/2010 |
| WO | 2010/135563 | A1 | 11/2010 |
| WO | 2011/091291 | A1 | 7/2011 |
| WO | 2011/150421 | A2 | 12/2011 |

OTHER PUBLICATIONS

U.S. Appl. No. 08/761,769, Office Action dated Aug. 8, 2002.
U.S. Appl. No. 08/761,769, Notice of Allowance and Fees Due dated Jan. 22, 2003.
U.S. Appl. No. 09/120,970, Office Action dated Sep. 6, 2000.
U.S. Appl. No. 09/120,970, Office Action dated Jun. 5, 2001.
U.S. Appl. No. 09/120,970, Office Action dated Jan. 12, 2005.
U.S. Appl. No. 09/120,970, Office Action dated Nov. 8, 2005.
U.S. Appl. No. 09/120,970, Notice of Allowance and Fees Due dated Aug. 6, 2010.
U.S. Appl. No. 09/560,539, Office Action dated Feb. 12, 2002.
U.S. Appl. No. 09/560,539, Office Action dated Mar. 25, 2003.
U.S. Appl. No. 09/560,539, Office Action dated Aug. 29, 2003.
U.S. Appl. No. 09/560,539, Notice of Allowance and Fees Due dated Mar. 30, 2004.
U.S. Appl. No. 09/686,499, Office Action dated Jun. 20, 2001.
U.S. Appl. No. 09/686,499, Office Action dated Jan. 29, 2002.
U.S. Appl. No. 09/686,499, Office Action dated Dec. 16, 2002.
U.S. Appl. No. 09/686,499, Office Action dated Aug. 27, 2003.
U.S. Appl. No. 09/686,499, Notice of Allowance and Fees Due dated Nov. 2, 2004.
U.S. Appl. No. 10/138,239, Office Action dated Mar. 15, 2005.
U.S. Appl. No. 10/138,239, Office Action dated Sep. 21, 2005.
U.S. Appl. No. 10/138,239, Notice of Allowance and Fees Due dated Mar. 16, 2006.
U.S. Appl. No. 10/414,533, Office Action dated Apr. 12, 2006.
U.S. Appl. No. 10/414,533, Notice of Allowance and Fees Due dated Dec. 8, 2006.
U.S. Appl. No. 10/511,616, Office Action dated Nov. 27, 2009.
U.S. Appl. No. 10/511,616, Office Action dated Jun. 23, 2010.
U.S. Appl. No. 10/511,616, Office Action dated Dec. 27, 2010.
U.S. Appl. No. 10/511,616, Notice of Allowance and Fees Due dated Oct. 26, 2011.
U.S. Appl. No. 10/620,777, Office Action dated Nov. 14, 2006.
U.S. Appl. No. 10/620,777, Office Action dated Oct. 31, 2007.
U.S. Appl. No. 10/924,574, Office Action dated Feb. 28, 2007.
U.S. Appl. No. 10/924,574, Notice of Allowance and Fees Due dated Oct. 1, 2007.
European Patent Application No. 08827622.5, Search Report dated Jun. 27, 2011.
European Patent Application No. 08827622.5, Office Action dated Feb. 22, 2012.
Nieto et al., Complex Structure of the nuclear translocation signal of influenza virus polymerase PA subunit. Journal of General Virology, 1994, pp. 29-36, vol. 75.
U.S. Appl. No. 12/681,711, Office Action dated Jan. 31, 2012.
U.S. Appl. No. 12/789,869, Office Action dated Mar. 22, 2011.
U.S. Appl. No. 12/789,869, Office Action dated Dec. 7, 2011.
Bang et al., OmpR regulates the stationary-phase acid tolerance response of *Salmonella enterica* serovar Typhimurium. J. Bacteriol, 2000, pp. 2245-2252, vol. 182.
Bang et al., Autoinduction of the ompR response regulator by acid shock and control of the *Salmonella enterica* acid tolerance response. Mol Microbiol, 2002, pp. 1235-1250, vol. 44.
Bartlett et al., Influenza A (H5N1): will it be the next pandemic influenza? Are we ready? Ann. Intern. Med., 2005, pp. 460-462, vol. 143.
Bartlett, Planning for avian influenza. Ann. Intern. Med., 2006, pp. 141-144, vol. 145.
Bearson et al., A low-pH-inducible, PhoPQ-dependent acid tolerance response protects *Salmonella typhimurium* against inorganic acid stress. J. Bacteriol, 1998, pp. 2409-2417, vol. 180.
Bertani, Studies on lysonucleic acid sequencesis. I. The mode of phage liberation by lysogenic *Escherichia coli*. J. Bacteriol, 1951, pp. 293-300, vol. 62, No. 3.
Black et al., Aspartic—semialdehydedehydrogenase and aspartic—semialdehyde, J. Biol. Chem., 1955, pp. 39-50, vol. 213.
Briles et al., Immunization of humans with recombinant pneumococcal surface protein A (rPspA) elicits antibodies that passively protect mice from fatal infection with *Streptococcus pneumoniae* bearing heterologous PspA. J. Infect. Dis., 2000, pp. 1694-1701, vol. 182.
Brooks-Walter et al., The pspC gene of *Streptococcus pneumoniae* encodes a polymorphic protein, PspC, which elicits cross-reactive antibodies to PspA and provides immunity to pneumococcal bacteremia. Infect. Immun. 1999, pp. 6533-6542, vol. 67.
Brosius et al., Spacing of the −10 and −35 regions in the tac promoter. Effect on its in vivo activity. J Biol Chem, 1985, pp. 3539-3540, vol. 260, No. 6.
Brown et al., MurA (MurZ), the enzyme that catalyzes the first committed step in peptidoglycan biosynthesis, is essential in *Escherichia coli*. J. Bacteriol., 1995, pp. 4194-4197, vol. 177.

(56) References Cited

OTHER PUBLICATIONS

Buchanan et al., IL-12 Enhances Antibody Responses to T-Independent Polysaccharide Vaccines in the Absence of T and NK Cells. J. Immunol., 1998, pp. 5525-5533, vol. 161.

Buchmeier, et al., DNA repair is more important than catalase for *Salmonella* virulence in mice. J. Clin. Invest., 1995, pp. 1047-1053, vol. 95.

Bumann, Regulated antigen expression in live recombinant *Salmonella enterica* serovar Typhimurium strongly affects colonization capabilities and specific CD4(+)-T-cell responses. Infect. Immun, 2001. pp. 7493-7500, vol. 69, No. 12.

Kotton et al, Enteric pathogens as vaccine vectors for foreign antigen delivery. Infect. Immun., 2004, pp. 5535-5547, vol. 72.

Lee et al., Characterization of recent H5 subtype avian influenza viruses from US poultry. Avian Pathol., 2004, pp. 288-297, vol. 33.

Lee et al., Mechanism of araC autoregulation and the domains of two overlapping promoters, PC and PBAD, in the L-arabinose regulatory region of *Escherichia coli*. Proc. Natl. Acad. Sci. USA, 1981, pp. 752-756, vol. 78.

Li et al. A sopB Deletion Mutation Enhances the Immunogenicity and Protective Efficacy of a Heterologous Antigen Delivered by Live Attenuated *Salmonella enterica* Vaccines. Infection and Immunity, 2008, pp. 5238-5246, vol. 76, No. 11.

Lee et al., Trigger factor retards protein export in *Escherichia coli*. J. Biol Chem, 2002, pp. 43527-43535, vol. 277.

Lefeber et al., Th1-directing adjuvants increase the immunogenicity of oligosaccharide-protein conjugate vaccines related to *Streptococcus pneumoniae* type 3. Infect Immun, 2003, pp. 6915-6920, vol. 71.

Loessner et al., Differential effect of auxotrophies on the release of macromolecules by *Salmonella enterica* vaccine strains. FEMS Microbiol. Lett., 2006, pp. 81-88, vol. 265.

Loewen et al., Genetic mapping of katF, a locus that with katE affects the synthesis of a second catalase species in *Escherichia coli*. J Bacteriol, 1984, pp. 668-675, vol. 160.

Luytjes et al., Amplification, expression, and packaging of foreign gene by influenza virus. Cell, 1989, pp. 1107-1113, vol. 59.

Malley et al., CD4+T cells mediate antibody-independent acquired immunity to pneumococcal colonization. PNAS, 2005, pp. 4848-4853, vol. 102.

Massin et al., Cloning of the chicken RNA polymerase I promoter and use for reverse genetics of influenza A viruses in avian cells. J. Virol. 2005, pp. 13811-13816, vol. 79.

Matthay et al., Evaluation of the opsonic requirements for phagocytosis of *Streptococcus pneumoniae* serotypes VII, XIV, and XIX by chemiluminescence assay. Infect Immun, 1981, pp. 228-235, vol. 31.

McClelland et al. Complete genome sequence of *Salmonella enterica* serovar Typhimurium LT2. Nature, 2001, pp. 852-856, vol. 413, No. 6858.

McDaniel et al., Monoclonal antibodies against protease sensitive pnuemococcal anitigens can protect mice form fatal infection with *Streptococcus pneumoniae*. J. Exp. Med., 1984, pp. 368-397, vol. 160.

McDaniel et al., Use of insertional inactivation to facilitate studies of biological properties of pneumococcal surface protein A (PspA). J. Exp. Med. 1987, pp. 381-394, vol. 165.

Miller et al., A novel suicide vector and its use in construction of insertion mutations: osmoregulation of outer membrane proteins and virulence determinants in Virbrio cholerae requires toxR. J. Bacteriol, 1988, pp. 2575-2583, vol. 170.

Miller et al, Bacteriophage T4 genome. Microbiol. Mol. Biol. Rev, 2003, pp. 86-156, vol. 67, No. 1.

Molinari et al., The annual impact of seasonal influenza in the US; measuring disease burden and costs. Vaccine, 2007, pp. 5086-5096, vol. 25.

Mulvey et al., Regulation of transcription of katE and katF in *Escherichia coli*. J Bacteriol, 1990, pp. 6713-6720, vol. 172.

Murti et al., Localization of RNA polymerases on influenza viral ribonucleoproteins by immunogold labeling. Virology, 1988, pp. 562-566, vol. 164.

Nardelli-Haefliger et al., Human papillomavirus type 16 virus-like particles expresses in attenuated *Salmonella typhimurium* elicit mucosal and systemic neutralizing antibodies in mice. Infect. Immun., 1997, pp. 3328-3336, vol. 65.

Nayak et al., A live recombinant avirulent oral *Salmonella* vaccine expressing pneumococcal surface protein A induces protective responses against *Streptococcus pneumoniae*. Infect. Immun. 1998, pp. 3744-3751, vol. 66.

Neumann et al., An improved reverse genetics system for influenza A virus generation and its implications for vaccine production. Proc. Natl. Acad. Sci. USA, 2005, pp. 16825-16829, vol. 102.

Neumann et al., Generation of influenza A viruses entirely from cloned cDNAs Proc. Natl. Acad. Sci. USA, 1999, pp. 9345-9350, vol. 96.

Neumann et al., RNA polymerase I-mediated expression of influenza viral RNA molecules. Virology, 1994, pp. 477-479, vol. 202.

Noda et al., Architecture of ribonucleoprotein complexes in influenza A virus particles. Nature, 2006, pp. 490-492, vol. 439.

Oehler et al., The three operators of the lac operon cooperate in repression. EMBO J, 1990, pp. 973-979, vol. 9, No. 4.

Ogunniyi et al., Contributions of Pneumolysin, Pneumococcal Surface Protein A (PspA), and PspC to Pathogenicity of *Streptococcus pneumoniae* D39 in a Mouse Model. Infect. Immun. 2007. pp. 1843-1851. vol. 75.

Osterholm, Preparing for the next pandemic, N. Engl. J. Med. 2005, pp. 1839-1842, vol. 352.

Ozaki et al., Generation of high-yielding influenza A viruses in African green monkey kidney (Vero) cells by reverse genetics. J. Virol. 2004, pp. 1851-1857, vol. 78.

Park et al., Engineered viral vaccine constructs with dual specificity: avian influenza and Newcastle disease. Proc. Natl. Acad. Sci. USA, 2006, pp. 8203-8208, vol. 103.

Pascual et al, Expression of Recombinant Enterotoxigenic *Escherichia coli* Colonization Factor Antigen I by *Salmonella typhimurium* Elicits a Biphasic T Helper Cell Response. Infect. Immun., 1999, pp. 6249-6256, vol. 67.

Pashine et al., Th1 dominance in the immune response to live *Salmonella typhimurium* requires bacterial invasiveness but not persistence. Int. Immunol., 1999, pp. 481-489, vol. 11.

Peterson et al., RpoS proteolysis is regulated by a mechanism that does not require the SprE (RssB) response regulator phosphorylation site. J Bacteriol, 2004, pp. 7403-7410, vol. 186.

Pizarro-Cerda et al., The bacterial signal molecule, ppGpp, regulates *Salmonella* virulence nucleic acid sequence expression. Mol Microbiol, 2004, pp. 1827-1844, vol. 52, No. 6.

Prouty et al., *Salmonella enterica* serovar Typhimurium invasion is repressed in the presence of bile. Infect Immun, 2000, pp. 6763-6769, vol. 68.

Quinlivan et al., Attenuation of equine influenza viruses through truncations of the NS1 protein. J. Virol., 2005, pp. 8431-8439, vol. 79.

Rand, Crystal violet can be used to visualize DNA bands during gel electrophoresis and to improve cloning efficiency. Tech Tips Online, 1996 http://www.science-direct.com/science/journal/13662120.

Roberts et al., Oral vaccination against tetanus: comparison of the immunogenicities of *Salmonella* strains expressing fragment C fromt he nirB and htrA promoters. Infect. Immun. 1998, pp. 3080-3087, vol. 66.

Romeo et al, Genetic regulation of glycogen biosynthesis in *Escherichia coli*: in vitro effects of cyclic AMP and guanosine 5'-diphosphate 3'-diphosphate and analysis of in vivo transcripts. J Bacteriol, 1989, pp. 2773-2782, vol. 171.

Sadler et al., A perfectly symmetric lac operator binds the lac repressor very tightly. Proc Natl Acad Sci USA 1983, pp. 6785-6789, vol. 80, No. 22.

Saeland et al., Serum samples from infants vaccinated with a pneumococcal conjugate vaccine, PncT, protect mice against invasive infection caused by *Streptococcus pneumoniae* serotypes 6A and 6B. J Infect Dis, 2001, pp. 253-560, vol. 183.

Hori et al, Construction of self disruptive Bacillus megaterium in response to substrate exhaustion for polyhydroxybutyrate production. Appl Microbiol Biotechnol, 2002, pp. 211-216, vol. 59.

(56) References Cited

OTHER PUBLICATIONS

Houng et al., Expression of Vi antigen in *Escherichia coli* K-12: characterization of ViaB form Citrobacter freundii and identity of ViaA with RcsB J. Bacterio, 1992, pp. 5910-5915, vol. 174, No. 18.
Schuchat et al, Bacterial meningitis in the United States in 1995. Active Surveillance Team. N. Engl. J. Med., 1997, pp. 970-976, vol. 337.
Schulman et al., Independent variation in nature of hemagglutinin and neuraminidase antigens of influenza virus: distinctiveness of hemagglutinin antigen of Hong Kong—68 virus. Proc. Natl. Acad. Sci. USA, 1969, pp. 326-333, vol. 63.
Simonsen et al., The impact of influenza epidemics of hospitalizations. J. Infect. Dis., 2000, pp. 831-837, vol. 181.
Rytkonen et al., SseI, A *Salmonella* deubiquitinase required for macrophase killing and virulence. PNAS, 2007, vol. 104 (pp. 3502-3507).
Ribeiro et al., The role of Polyadenylation Signal Secondary Structures on the Resistance of Plasmid Vectors to Nucleases. J. Gene Med., vol. 6, 2004 (pp. 565-573).
Wang et al., Hemagglutinin (HA) Proteins from H1 and H3 Serotypes of Influenza A Viruses Require Different Antigen Designs for the Induction of Optimal Protective Antibody Responses as Studied by Codon—Optimized HA DNA Vaccines. Journal of Virology, 2006. vol. 80 (pp. 11628-11637).
Sheehan et al., Generation and characterization of hamster monoclonal antibodies that neutralize murine tumor necrosis factors. J Immunol, 1989, pp. 3884-3893, vol. 142.
Sizemore et al., Attenuated bacteria as a DNA delivery vehicle for DNA-mediated immunization. Vaccine, 1997, pp. 804-807, vol. 15.
Snapper et al., Distinct types of T-cell help for the induction of a humoral immune response to *Streptococcus pneumoniae*. Trends Immunol, 2001, pp. 308-311, vol. 22.
Sodeinde et al., Plasminogen activator/coagulase gene of Yersinia pestis is responsible for degradation of plasmid-encoded outer membrane proteins. Infect Immun, 1988, pp. 2749-2752, vol. 56.
Sternberg et al., Bacteriophage-mediated nucleic acid sequenceralized transduction in *Escherichia coli* and *Salmonella typhimurium*. Methods Enzymol, 1991, pp. 18-43, vol. 204.
Straley et al., Virulence genes regulated at the transcriptional level by Ca2+ in Yersinia pestis include structural genes for outer membrane proteins. Infect Immun, 1986, pp. 445-454, vol. 51.
Sun et al., The role of relA and spoT in Yersinia pestis KIM5+ pathogenicity. PLoS One, 2009, pp. E6720, vol. 4.
Thompson et al., The bacterial signal molecule, ppGpp, mediates the environmental regulation of both the invasion and intracellular virulence gene programs of *Salmonella*. J Biol Chem, 2006, pp. 30112-30121, vol. 281.
Une et al., In vivo comparison of avirulent Vwa- and Pgm- or Pstr phenotypes of Yersiniae. Infect Immun, 1984, pp. 895-900, vol. 43.
Uzzau et al., Epitope tagging of chromosomal genes in *Salmonella*. Proc Natl Acad Sci U S A, 2001, pp. 15264-15269, vol. 98.
Viboud et al., Yersinia outer proteins: role in modulation of host cell signaling responses and pathogenesis. Annu Rev Microbiol, 2005, pp. 69-89, vol. 59.
Wasserman et al., Two alanine racemase genes in *Salmonella typhimurium* that differ in structure and function. J. Bacteriol., 1983, pp. 1439-1450, vol. 153.
Whitfield, Biosynthesis and assembly of capsular polysaccharides in *Escherichia coli*. Annu Rev. Biochem., 2006, pp. 39-68, vol. 75.
Winter et al., The *Salmonella enterica* serotype Typhi regulator TviA reduces interleukin-8 production in intestinal epithelial cells by repressing flagellin secretion. Cell Microbiol, 2008, pp. 247-261, vol. 10, No. 1.
Wolf et al., Evolution of aminoacyl tRNA synthetases—analysis of unique domain architectures and phylogenetic trees reveals a complex history of horizontal gene transfer events. Genome Res, 1999, pp. 689-710, vol. 9.
Xiao et al., Residual guanosine 39,59-bispyrophosphate synthetic activity of relA null mutants can be eliminated by spoT null mutations. J Biol Chem, 1991, pp. 5980-5990, vol. 266.

Zahorchak et al., Effect of exogenous nucleotides on Ca2+ dependence and V antigen synthesis in Yersinia pestis. Infect Immun, 1982, pp. 953-959, vol. 38.
Zhang et al., A "one-plasmid" system to generate influenza virus in cultured chicken cells for potential use in influenza vaccine. J. Virol., 2009, pp. 9296-9303, vol. 83.
Zhang et al., Transcription activation parameters at ara pBAD. J Mol Biol, 1996, pp. 14-24, vol. 258, No. 1.
Zinkernagel et al., Antigen localisation regulates immune responses in a dose- and time-dependent fashion: a geographical view of immune reactivity. Immunol Rev, 1997, pp. 199-209, vol. 156.
Briles et al., PspA, a protection-eliciting pneumococcal protein: immunogenicity of isolated native PspA in mice. Vaccine, 1996, pp. 858-867, vol. 14.
Hanisch, et al, The Ralstonia eutropha H16 phasin PhaP1 is targeted to intracellular triacylglycerol inclusions in Rhodococcus opacus PD630 and *Mycobacterium smegmatis* mc2155, and provides an anchor to target other proteins. Microbiology, 2006, pp. 3271-3280, vol. 152.
Kong et al, Regulated Delayed Expression of rfaH in an Attenuated *Salmonella enterica* Serovar Typhimurium Vaccine Enhances Immunogenicity of Outer Membrane Proteins and Heterologous Antigen. Infec Immun. 2009, pp. 5572-5582, vol. 77, No. 12.
U.S. Appl. No. 13/302,575, Office Action dated Sep. 25, 2012.
Morita et al., Antibacterial Activity of Bacillus amyloliquefaciencs Phage Endolysin without Holin Conjugation. Journal of Biosciences and Bioengineering, 2001, pp. 469-473, vol. 91, No. 5.
U.S. Appl. No. 13/302,575, Office Action dated Jun. 18, 2013.
Stevens, Immunization with the C-Domain of alpha-Toxin Prevents Lethal Infection, Localizes Tissue Injury, and Promotes Host Responses to Challenge with Clostridium perfringens. JID, 2004, pp. 767-773, vol. 190.
Verjan et al, Genetic Loci of Major Antigenic Protein Genes of Edwardsiella tarda. Applied and Environmental Microbiology, 2005, pp. 5654-5658, vol. 71, No. 9.
U.S. Appl. No. 12/599,655 Office Action dated Jul. 2, 2012.
U.S. Appl. No. 12/681,721, Office Action dated May 24, 2012.
U.S. Appl. No. 12/759,842, Office Action dated Jun. 7, 2012.
Ellis, New Technologies for Making Vaccines. Vaccines, 1988, pp. 568-574, Chapter 29, WB Saunders Company, United States.
Greenspan et al, Defining eptiopes: It's not as easy as it seems. Nature Biotechnology, 1999, pp. 936-937, vol. 17.
Houghten et al, Relative Importance of Position and Individual Amino Acid Residues in Peptide Antigen-Antibody Interactions: Implications in the Mechanism of Antigenic Drift and Antigenic Shift. Vaccines86, 1986, pp. 21-25; Cold Spring Harbor Laboratory.
U.S. Appl. No. 12/615,872 Office Action dated Oct. 23, 2012.
Bittner et al., RpoS and RpoN are involved in the growth-dependent regulation of rfaH transcription and O antigen expression in *Salmonella enterica* serovar Typhi, Microbial Pathogenisis. vol. 36, 2004 (p. 19).
Kong et al, *Salmonella* Synthesizing 1-Monophosphorylated Lipopolysaccharide Exhibits Low Endotoxic Activity while Retaining its Immunogenicity. J. Immunol. Jun. 1, 2011, vol. 187, pp. 412-423.
Moreno et al., *Salmonella* as Live Trojan Horse for Vaccine Development and Cancer Gene Therapy. Current Gene Therapy, 2010, 10: 56-76.
PCT/US2011/061896 (WO2012/087483)—International Search Report and Written Opinion of the International Searching Authority, Apr. 5, 2012.
Spellberg et al., Type 1/type 2 immunity in infectious diseases. Clin. Infect. Dis., 2001, pp. 76-102, vol. 32.
Schnaitman et al., Genetics of Lipopolysaccharide Biosynthesis in Enteric Bacteria. Microbiological Reviews, 1993, pp. 655-682, vol. 57, No. 3.
Byl et al, Sequence of the Genomore of *Salmonella* Bacteriophage P22. Journal of Bacteriology, 2000, pp. 6472-6484, vol. 182, 22.
Steel et al., Live attenuated influenza viruses containing NS1 truncations as vaccine candidates against H5N1 highly pathogenic avian influenza. J. Virol., 2009, pp. 1742-1753, vol. 83.

(56) References Cited

OTHER PUBLICATIONS

Tacket et al., Safety and immunogenicity in humans of an attenuated *Salmonella typhi* vaccine vector strain expressing plasmid-encoded hepatitis B antigens stabilized by the asd-balanced lethal vector system. Infect Immun, 1997, pp. 3381-3385, vol. 65.
Taubenberger et al., 1918 Influenza: the mother of all pandemics. Emerg. Infect. Dis., 2006, pp. 15-22, vol. 12.
Török et al., Accumulation of ppGpp in a relA mutant of *Escherichia coli* during amino acid starvation. J. Biol. Chem., 1980, pp. 3838-3840, vol. 255.
Tu et al., The PhoP/PhoQ two-component system stabilizes the alternative sigma factor RpoS in *Salmonella enterica*. Proc Natl Acad Sci U S A., 2006, pp. 13503-13508, vol. 103.
Tumpey et al., Characterization of the reconstructed 1918 Spanish influenza pandemic virus. Science, 2005, pp. 77-80, vol. 310.
Van Rossum et al., Host and bacterial factors contributing to the clearance of colonization by *Streptococcus pneumoniae* in a murine model. Infect Immun, 2005, pp. 7718-7726, vol. 73.
Van Velkinburgh et al., PhoP-PhoQ-regulated loci are required for enhanced bile resistance in *Salmonella* spp. Infect Immun, 1999, pp. 1614-1622, vol. 67.
Webster et al., Evolution and ecology of influenza A viruses. Microbiol Rev, 1992, pp. 152-179, vol. 56.
Wilmes-Riesenberg et al., Role of acid tolerance response in virulence of *Salmonella typhimurium*. InfectImmun, 1996, pp. 1085-1092, vol. 64.
Wu et al., The mechanism underlying T cell help for induction of an antigen-specific in vivo humoral immune response to intact *Streptococcus pneumoniae* is dependent on the type of antigen. J Immunol, 2002, pp. 5551-5557, vol. 168.
Zahn, Overexpression of an mRNA dependent on rare codons inhibits protein synthesis and cell growth. J Bacteriol, 1996, pp. 2926-2933, vol. 178, No. 10.
Zhang et al., Characterization and immunogenicity of *Salmonella typhimurium* SL1344 and UK-1 crp and cdt deletion mutants. Infect. Immun., 1997, pp. 5381-5387, vol. 65.
Zobel et al., RNA polymerase I catalysed transcription of insert viral cDNA. Nucleic. Acids. Res., 1993, pp. 3607-3614, vol. 21.
Baek et al., Leucine-Responsive Regulator Protein (Lrp) Acts as a Virulence Respressor in *Salmonella enterica* Servoar Typhimurium. Journal of Bacteriology, 2009, pp. 1278-1292, vol. 191, No. 4.
U.S. Appl. No. 12/615,872, Office Action dated Mar. 14, 2012.
Collins et al, Mutation at rfc or pmi Attenuate *Salmonella typhimurium* Virulence for Mice. Infect and Immun, 1991, pp. 1079-1085, vol. 59, No. 3.
Curtiss et al., Stabilization of Recombinant Avirulent Vaccine Strains in vivo. Res. Microbiol., 1990, pp. 797-805, vol. 141.
Curtiss et al, Avirulent *Salmonell typhimurim* cyc crp oral vaccine strains expressing a streptococcal colonization and virulence antigen. Vaccine, 1988, pp. 155-160, vol. 6.
Darzins et al., Nucleotide sequence analysis of the phosphomannose isomerase gene (pmi) of Pseudomonas aeruginose and comparison with the corresponding *Escherichia coli* gene manA. Gene, 1986, pp. 293-302, vol. 42.
Doggett et al., Immune Responses to *Streptococcus sobrinus* Surface Protein Antigen A Expressed by Recombinant *Salmonella typhimurium*. Infect and Immun, 1993, pp. 1859-1866, vol. 61, No. 5.
Egan et al., A Regulatory Cascade in the Induction of rhaBAD. J. Mol. Biol., 1993, pp. 87-98, vol. 234.
Guzman et al., Tight regulations, Modulations, and High-Level Expression by Vectors Containing the Arabinose Pbad Promotor. Journal of Bacteriology, 1995, pp. 4121-4130, vol. 177, No. 14.
Kennedy et al., Attenuation and Immunogenicity of cya crp Derivatives of *Salmonella choleraeuis* in Pigs. Infect Immun, 1999, pp. 4628-4636, vol. 67, No. 9.
Nickerson et al., Role of Sigma Factor RpoS in Initial Stages of *Salmonella typhimurium* Infection. Infect Immun, 1997, p. 1814-1823, vol. 65, No. 5.

Schodel et al., Hybrid Hepatitis B Virus Core-Pre-S Proteins Synthesized in Avirulent *Salmonella typhimurium* and *Salmonella typhi* for Oral Vaccination. Infect Immun, 1994, pp. 1669-1676, vol. 62, No. 5.
Schodel, Recombinant Avirulent Salmonellae as Oral Vaccine Carriers. Infection, 1992, vol. 20, pp. 1-12, No. 1.
Siegele et al., Gene Expression from plasmids containing the araBAD promoter at subsaturating inducer concentrations represents mixed populations. PNAS, 1997, pp. 8168-8172, vol. 94.
Song et al., Organization and Regulation of the d-Xylose Operons in *Escherichia coli* K-12: XyIR Acts as a Transcriptional Activator. Journal of Bacteriology, 1997, pp. 7025-7032, vol. 179, No. 22.
Srinivasan et al., Oral Immunization with Attenuated *Salmonella* Expressing Human Sperm Antigen Induces Antibodies in Serum and the Reproductive Tract. Biology of Reproduction, 1995, p. 462-471 vol. 53.
PCT/US2008/063293 (WO 2009/025888)—International Search Report and Written Opinion of the International Searching Authority, Feb. 12, 2009.
Mesika et al., A Regulated, NFkB—Assisted Import of Plasmid DNA into Mammalian Cell Nuclei, Molecular Therapy, vol. 3, No. 5, May 2001, pp. 653-657.
Quenee, et al., Yersinia pestis caf1 Variants and the Limits of Plague Vaccine Protection, Infection and Immunity, May 2008, vol. 76, No. 5, pp. 2025-2036.
U.S. Appl. No. 13/088,141, Office Action dated Dec. 6, 2012.
U.S. Appl. No. 13/006,072, Office Action dated Dec. 11, 2012.
Kong. Improving DNA Vaccine Vector for Efficient Vaccine Delivery using Live Attenuated Bacterial Carrier. American Society for Microbiology, T-010, 2008, vol. 108, p. 668.
Whitworth et al., Expression of the Rickettsia prowazekii pld or tlyC Gene in *Salmonella enterica* Serovar Typhimurium Mediates Phagosomal Escape, Infection and Immunity, 2005, vol. 73(10), pp. 6668-6673.
Folkesson et al., Components of the peptidoglycan-recycling pathway modulate invasion and intracellular survival of *Salmonella enterica* serovar Typhimurium. Cellular Microbiology, 2005, vol. 7(1) pp. 147-155.
U.S. Appl. No. 12/599,655, Office Action dated Mar. 12, 2013.
U.S. Appl. No. 12/681,711, Office Action dated Nov. 28, 2012.
U.S. Appl. No. 12/789,869, Office Action dated Jun. 3, 2014.
U.S. Appl. No. 13/088,141, Office Action dated Apr. 24, 2014.
U.S. Appl. No. 13/574,718, Office Action dated Sep. 6, 2013.
U.S. Appl. No. 13/574,718, Office Action dated Apr. 28, 2014.
Takaya, A. et al, The ATP-Dependent Lon Protease of *Salmonella enterica* Serovar Typhimurium Regulates Invasion and Expression of Genes Carried on *Salmonella* Pathogenicity Island 1. Journal of Bacteriology. Jan. 2002, vol. 184(1), pp. 224-232: abstract.
Navasa, M. et al., Temperature has reciprocal effect on colanic acid and polysialic acid biosynthesis in *E. coli* K92. Appl. Microbiol Biotechnol., Jan. 13, 2009, vol. 82, pp. 721-729.
PCT/US/2008/063303 (WO2008/141226)—International Search Report and Written Opinion of the International Searching Authority, Nov. 26, 2008.
U.S. Appl. No. 12/759,842, Office Action dated Oct. 4, 2011
PCT/US2008/078991 (WO2009/046449)—International Search Report and Written Opinion of the International Searching Authority, Dec. 15, 2008.
PCT/US2008/078993 (WO2009/046451)—International Search Report and Written Opinion of the International Searching Authority, Dec. 15, 2008.
PCT/US2010/035630 (WO2010/135563)—International Search Report and Written Opinion of the International Searching Authority, Sep. 29, 2010.
PCT/US2009/061100 (WO2010/045620)—International Search Report and Written Opinion of the International Searching Authority, Dec. 4, 2009.
PCT/US2010/020137 (WO 2010/078584)—International Search Report and Written Opinion of the International Searching Authority, Mar. 9, 2010.
PCT/US2011/022110 (WO2011/091291)—International Search Report and Written Opinion of the International Searching Authority, Apr. 11, 2011.

(56) References Cited

OTHER PUBLICATIONS

PCT/US2011/038588 (WO2011/150421)—International Search Report and Written Opinion of the International Searching Authority, Nov. 22, 2011.
PCT/US98/24295—International Preliminary Examination Report, Dec. 26, 2000 (WO/1999/025387).
PCT/US2001/013915—International Preliminary Examination Report, Aug. 16, 2002 (WO/2001/083785).
European Patent Application No. 89910552.2 (EP0433372), Intention to Grant dated Jun. 19, 2001.
European Patent Application No. 89910552.2 (EP0433372), Office Action dated Oct. 10, 1994.
European Patent Application No. 89910552.2 (EP0433372), Office Action dated Sep. 12, 1995.
European Patent Application No. 89910552.2 (EP0433372), Office Action dated Jun. 20, 2000.
European Patent Application No. 89910552.2 (EP0433372), Decision to Grant dated May 6, 2002.
European Patent Application No. 90905859.6 (EP0465560), Office Action dated Feb. 19, 1992.
European Patent Application No. 90905859.6 (EP0465560), Office Action dated Feb. 9, 1994.
European Patent Application No. 90905859.6 (EP0465560), Intention to Grant dated Jan. 4, 1995.
European Patent Application No. 90905859.0 (EP0465560), Decision to Grant dated Apr. 25, 1996.
European Patent Application No. 96919292.1 (EP0832255), Office Action dated Sep. 30, 2003.
European Patent Application No. 96919292.1 (EP0832255), Office Action dated Jul. 13, 2004.
European Patent Application No. 96919292.1 (EP0832255), Intention to Grant dated May 25, 2005.
European Patent Application No. 96919292.1 (EP0832255), Decision to Grant dated Nov. 4, 2005.
European Patent Application No. 98958581.5 (EP1030690), Office Action dated Jan. 31, 2001.
European Patent Application No. 98958581.5 (EP1030690), Intention to Grant dated Sep. 27, 2001.
European Patent Application No. 98958581.5 (EP1030690), Decision to Grant dated May 24, 2002.
European Patent Application No. 01944119.5 (EP1292687), Office Action dated Oct. 18, 2004.
European Patent Application No. 01944119.5 (EP1292687), Office Action dated Aug. 4, 2005.
European Patent Application No. 01944119.5 (EP1292687), Intention to Grant dated Jan. 26, 2006.
European Patent Application No. 01944119.5 (EP1292687), Decision to Grant dated Jul. 20, 2006.
European Patent Application No. 01979646.5 (EP1326960), Intention to Grant dated Apr. 8, 2004.
European Patent Application No. 01979646.5 (EP1326960), Decision to Grant dated Oct. 28, 2004.
European Patent Application No. 03721711.4 (EP1499191), Search Report dated May 23, 2006.
European Patent Application No. 03721711.4 (EP1499191), Office Action dated Aug. 24, 2006.
European Patent Application No. 03721711.4 (EP1499191), Office Action dated Jan. 17, 2007.
European Patent Application No. 03721711.4 (EP1499191), Office Action dated Mar. 23, 2009.
European Patent Application No. 03721711.4 (EP1499191), Office Action dated Jun. 15, 2010.
European Patent Application No. 03721711.4 (EP1499191), Intention to Grant dated Oct. 21, 2011.
European Patent Application No. 03770256.0 (EP1537214), Intention to Grant dated Aug. 12, 2005.
U.S. Appl. No. 08/473,789, Office Action dated Apr. 15, 1997.
U.S. Appl. No. 08/473,789, Office Action dated Dec. 23, 1997.
U.S. Appl. No. 08/473,789, Office Action dated Nov. 13, 1998.
U.S. Appl. No. 08/473,789, Office Action dated Jun. 14, 1999.
U.S. Appl. No. 08/473,789, Office Action dated Jan. 21, 2000.
U.S. Appl. No. 08/473,789, Office Action dated Jul. 25, 2000.
U.S. Appl. No. 08/473,789, Office Action dated Sep. 27, 2001.
U.S. Appl. No. 08/761,769, Office Action dated Jul. 20, 1998.
U.S. Appl. No. 08/761,769, Office Action dated Mar. 3, 1999.
U.S. Appl. No. 08/761,769, Office Action dated Aug. 9, 2000.
CDC, Update: influenza activity—United States, Sep. 30, 2007-Apr. 5, 2008, and composition of the Sep. 2008 influenza vaccine. MMWR Morb. Mortal. Wkly Rep., 2008, pp. 404-409, vol. 57.
Chen et al., Genetic mapping of the cold-adapted phenotype of B/Ann Arbor/1/66, the master donor virus for live attenuated influenza vaccines (FluMist). Virology, 2006, pp. 416-423, vol. 345.
U.S. Appl. No. 13/006,072, Office Action dated Apr. 19, 2012.
Sun et al., Highly efficient method for introducing successive multiple scarless gene deletions and markerless gene insertions into the Yersinia pestis chromosome. Appl Environ Microbiol, 2008, pp. 4241-4245, vol. 74.
Curtiss et al., New technologies in using recombinant attenuated *Salmonella* vaccine vectors. Crit. Rev. Immunol., 2010, pp. 255-270, vol. 30.
Curtiss et al., *Salmonella* strains with regulated delayed attenuation in vivo. Infect. Immun., 2009, pp. 1071-1082, vol. 77.
Curtiss et al., *Salmonella typhimurium* deletion mutants lacking adenylate cyclase and cyclic Amp receptor protein are avirulent and immunogenic. Infect Immun, 1987, pp. 3035-3043, vol. 55.
Waltman et al., Biochemical Characteristics of Edwardsiella ictaluri. Applied and Enviornmental Microbiology, 1986, pp. 101-104, vol. 51, No. 1.
Curtiss, Bacterial infectious disease control by vaccine development. J. Clin. Investig., 2002, pp. 1061-1066, vol. 110.
Curtiss, Chromosomal aberrations associated with mutations to bacteriophage resistance in *Escherichia coli*. J. Bacteriol., 1965, pp. 28-40, vol. 89.
Daigle et al., Identification of *Salmonella typhi* genes expressed within macrophages by selective capture of transcribed sequences (Scots). Mol Microbiol, 2001, pp. 1211-1222, vol. 41.
U.S. Appl. No. 13/700,591, Office Action dated Apr. 2, 2014.
Dean, 1997. Import of plasmid DNA into the nucleus is sequence specific. Exp. Cell Res., 1997, pp. 293-302, vol. 230.
Reed et al., The W-Beijing Lineage of *Mycobacterium tuberculosis* Overproduces Triglycerides and Has the DosR Dormancy Regulon Constitutively Upregulated. Journal of Bacteriology, 2007, pp. 2583-2589, vol. 189, No. 7.
Dunstan et al., Comparison of the Abilities of Different Attenuated *Salmonella typhimurium* Strains to Elicit Humoral Immune Responses against a Heterologous Antigen. Infect. Immun., 1998, pp. 732-740, vol. 66.
Dusek et al., Brown, Systemic and mucosal immune responses in mice orally immunized with avirulent *Salmonella typhimurium* expressing a cloned Porphyromonas gingivalis hemagglutinin. Infect Immun, 1994, pp. 1652-1657, vol. 62, No. 5.
Pickard et al., Characterization of defined ompR mutants of *Salmonella typhi*: ompR is involved in the regulation of Vi polysaccharide expression. Infect Immun, 1994, pp. 3984-3993, vol. 62, No. 9.
Egorov et al., Transfectant influenza A viruses with long deletions in the NS1 protein grow efficiently in Vero cells. J. Virol., 1998, pp. 6437-6441, vol. 72.
Enami et al., Introduction of site-specific mutations into the genome of influenza virus. Proc. Natl. Acad. Sci. USA, 1990, pp. 3802-3805, vol. 87.
Fodor et al., Rescue of influenza A virus from recombinant DNA. J. Virol., 1999, pp. 9679-9682, vol. 73.
Formal et al., Construction of a potential bivalent vaccine strain: introduction of Shigella sonnei form I antigen genes into the galE *Salmonella typhi* Ty21a typhoid vaccine strain. Infect. Immun., 1981, pp. 746-750, vol. 34.
Fraser et al., The amino acid composition of T3 bacteriophage. J Biol Chem, 1953, pp. 291-295, vol. 205, No. 1.
Galan et al., Cloning and molecular characterization of genes whose products allow *Salmonella typhimurium* to penetrate tissue culture cells. Proc Natl Acad Sci U S A, 1989, pp. 6383-6387, vol. 86.

(56) References Cited

OTHER PUBLICATIONS

Galen et al., Optimization of Plasmid Maintenance in the Attenuated Live Vector Vaccine Strain *Salmonella typhi* CVD 908-htrA. Infect. Immun., 1999, pp. 6424-6433, vol. 67.

Garmory et al., Antibiotic-free plasmid stabilization by operator-repressor titration for vaccine delivery by using live *Salmonella enterica* serovar Typhimurium. Infect. Immun., 2005, pp. 2005-2011, vol. 73.

Gay et al., Positive selection procedure for entrapment of insertion sequence elements in gram-negative bacteria. J Bacteriol, 1985, pp. 918-921, vol. 164, No. 2.

Gentschev et al., Delivery of the p67 sporozoite antigen of Theileria parva by using recombinant *Salmonella dublin*: secretion of the product enhances specific antibody responses in cattle. Infect. Immun., 1998, pp. 2060-2064, vol. 66.

Gerdil, The annual production cycle for influenza vaccine. Vaccine, 2003, pp. 1776-1779, vol. 21.

Ghany et al. Candidate live, attenuated *Salmonella enterica* serotype Typhimurium vaccines with reduced fecal shedding are immunogenic and effective oral vaccines. Infect. Immun., 2007, pp. 1835-1842, vol. 75.

Greenwood, The epidemiology of pneumococcal infection in children in the developing world. Philos. Trans. R. Soc. Lond. B. Biol. Sci., 1999, pp. 777-785, vol. 354.

Gulig et al., Plasmid-associated virulence of *Salmonella typhimurium*. Infect Immun, 1987, pp. 2891-2901, vol. 55.

Lefman J. et al, Three-Dimensional Electron Microscopic Imaging of Membrane Invaginations in *Excherichia coli* Overproducing the Chemotaxis Receptor Tsr. Journal of Bacteriology. Aug. 2004, vol. 186 (15), pp. 5052-5061: abstract p. 5054.

Hall et al., The role of fur in the acid tolerance response of *Salmonella typhimurium* is physiologically and genetically separable from its role in iron acquisition. J Bacteriol, 1996, pp. 5683-5691, vol. 178.

Hess et al., Superior efficacy of secreted over somatic antigen display in recombinant *Salmonella* vaccine induced protection against listeriosis. Proc. Natl. Acad. Sci. USA, 1996, pp. 1458-1463, vol. 93.

Hicks et al., Incidence of pneumococcal disease due to non-pneumococcal conjugate vaccine (PCV7) serotypes in the United States during the era of widespread PCV7 vaccination, 1998-2004. J Infect Dis, 2007, pp. 1346-1354, vol. 196.

Hitchcock et al., Morphological heteronucleic acid sequenceity among *Salmonella* lipopolysaccharide chemotypes in silver-stained polyacrylamide gels. J Bacteriol, 1983, pp. 269-277, vol. 154, No. 1.

Hoffmann et al., "Ambisense" approach for the generation of influenza a virus: vRNA and mRNA synthesis from one template. Virology, 2000, pp. 310-317, vol. 267.

Hohmann et al., Macrophage-inducible expression of a model antigen in *Salmonella typhimurium* enhances immunogenicity. Proc Natl Acad Sci U S A, 1995, pp. 2904-2908, vol. 92, No. 7.

Hollingshead et al., Diversity of PspA: mosaic genes and evidence for past recombination in *Streptococcus pneumoniae*. Infect Immun., 2000, pp. 5889-5900, vol. 68.

Hopkins et al., A recombinant *Salmonella typhimurium* vaccine induces local immunity by four different routes of immunization. Infect Immun, 1995, pp. 3279-3286, vol. 63.

Jin et al., Multiple amino acid residues confer temperature sensitivity to human influenza virus vaccine strains (FluMist) derived from cold-adapted a/Ann Arbor/6/60. Virology, 2003, pp. 18-24, vol. 306.

Kang et al., Immune responses dependent on antigen location in recombinant attenuated *Salmonella typhimurium* vaccines following oral immunization. FEMS Immunol. Med. Microbiol. Lett., 2003, pp. 99-104, vol. 37.

Kang et al., Immune responses to recombinant pneumococcal PspA antigen delivered by live attenuated *Salmonella enterica* serovar typhimurium vaccine. Infect. Immun., 2002, pp. 1739-1749, vol. 70.

Kang et al., Transduction-mediated transfer of unmarked deletion and point mutations through use of counterselectable suicide vectors. J Bacteriol, 2002, pp. 307-312, vol. 184.

Katzman et al., Invertebrate connective tissue. Isolation of D-arabinose from sponge acidic polysaccharide. Biochem J, 1970, pp. 17-19, vol. 119, No. 1.

Hurme et al, A Proteinaceous Gene Regulator Thermameter in *Salmonella*. Cell, 1997, pp. 55-64, vol. 90.

Kilbourne, Studies on influenza in the pandemic of 1957-1958. III. Isolation of influenza A (Asian strain) viruses from influenza patients with pulmonary complications; details of virus isolation and characterization of isolates, with quantitative comparison of isolation methods. J. Clin. Invest., 1959, pp. 266-274, vol. 38.

Klumpp et al., Roles of the influenza virus polymerase and nucleoprotein in forming a functional RNP structure. EMBO J., 1997, pp. 1248-1257, vol. 16.

Kong et al, Regulated programmed lysis of recombinant *Salmonella* in host tissues to release protective antigens and confer biological containment. PNAS, 2008, pp. 9361-9366, vol. 105, No. 27.

Konjufca et al., A Recombinant Attenuated *Salmonella enterica* Serovar Typhimurium Vaccine Encoding Eimeria acervulina Antigen Offers Protection against E. acervulina Challenge. Infect. Immun., 2006, pp. 6785-6796, vol. 74.

Hess et al., Secretion of different listeriolysin cognates by recombinant attenuated *Salmonella typhimurium*: superior efficacy of haemolytic over non-haemolytic constructs after oral vaccination. Microbes Infect, 2000, pp. 1799-1806, vol. 2.

Hohmann et al., Evaluation of a phoP/phoQ-deleted, aroA-deleted live oral *Salmonella typhi* vaccine strain in human volunteers. Vaccine, 1996, pp. 19-24, vol. 14.

Hu et al., The inducible lac operator-repressor system is functional in mammalian cells. Cell, 1987, pp. 555-566, vol. 48, No. 4.

Hu et al., The inducible lac operator-repressor system is functional for control of expression of injected DNA in Xenopus oocytes. Gene, 1988, pp. 301-313, vol. 62, No. 2.

Huang et al., Genome-wide screen of *Salmonella* nucleic acid sequences expressed during infection in pigs, using in vivo expression technology. Appl Environ Microbiol, 2007, pp. 7522-7530, vol. 73, No. 23.

Iannelli et al., Allelic variation in the highly polymorphic locus pspC of *Streptococcus pneumoniae*. Gene, 2002, pp. 63-71, vol. 284.

In Soo Lee et al., The stationary-phase sigma factor sS (RpoS) is required for a sustained acid tolerance response in virulent *Salmonella typhimurium*. Molecular Microbiology, 1995, pp. 155-167, vol. 17.

Isoda et al., Expression of a Porphyromonas gingivalis hemagglutinin on the surface of a *Salmonella* vaccine vector. Vaccine, 2007, pp. 117-126, vol. 25, No. 1.

Ivancic-Bace et al, Effects of recJ, recQ, and recFOR mutations on recombination in nuclease-deficient recB recD double mutants of *Escherichia coli*. J. Bacteriol., 2005, pp. 1350-1356, vol. 187.

Kaufmann et al., Impact of intracellular location of and antigen display by intracellular bacteria: implications for vaccine development. Immunol. Lett., 1999, pp. 81-84, vol. 65.

Khan et al., Immunogenicity and protective efficacy of DnaJ (hsp40) of *Streptococcus pneumoniae* against lethal infection in mice. Vaccine, 2006, pp. 6225-6231, vol. 24.

Kim et al., Direct transcriptional control of the plasminogen activator gene of Yersinia pestis by the cyclic Amp receptor protein. J Bacteriol, 2007, pp. 8890-8900, vol. 189.

Kolodrubetz et al., Regulation of the L-arabinose transport operons in *Escherichia coli*. J Mol Biol, 1981, pp. 215-227, vol. 151, No. 2.

Kwon et al., *Salmonella*-based vaccines for infectious diseases. Expert Review of Vaccines, 2007, pp. 147-152, vol. 6.

Lange et al., Identification of a central regulator of stationary-phase gene expression in *Escherichia coli*. Mol Microbiol, 1991, pp. 49-59, vol. 5.

Lee et al., Regulation of L-arabinose transport in *Salmonella typhimurium* LT2. Mol Gen Genet, 1982, pp. 136-141, vol. 185, No. 1.

Lee et al., Surface-displayed viral antigens on *Salmonella* carrier vaccine. Nat Biotechnol, 2000, pp. 645-648, vol. 18, No. 6.

Lewis, The lac repressor. C R Biol, 2005, pp. 521-548, vol. 328, No. 6.

(56) References Cited

OTHER PUBLICATIONS

Lobell et al., AraC-DNA looping: orientation and distance-dependent loop breaking by the cyclic Amp receptor protein. J Mol Biol, 1991, pp. 45-54, vol. 218.
Lobocka et al., Organization and expression of the *Escherichia coli* K-12 dad operon encoding the smaller subunit of D-amino acid dehydrogenase and the catabolic alanine racemase. J. Bacteriol., 1994, pp. 1500-1510, vol. 176.
Loessner et al., Bacteria-mediated DNA transfer in gene therapy and vaccination. Expert. Opin. Biol. Ther., 2004, pp. 157-168, vol. 4.
Loessner et al., Remote control of tumour-targeted *Salmonella enterica* serovar Typhimurium by the use of L-arabinose as inducer of bacterial gene expression in vivo. Cell Microbiol, 2007, pp. 1529-1537, vol. 9.
Marshall et al., Use of the stationary phase inducible promoters, spy and dps, to drive heterologous antigen expression in *Salmonella* vaccine strains. Vaccine, 2000, pp. 1298-1306, vol. 18, No. 14.
Medina et al., Use of live bacterial vaccine vectors for antigen delivery: potential and limitations. Vaccine, 2001, pp. 1573-1580, vol. 19.
Mehigh et al., Expression of the low calcium response in Yersinia pestis. Microb Pathog, 1989, pp. 203-217, vol. 6.
Moore et al., Enhanced protective immunity against pneumococcal infection with PspA DNA and protein. Vaccine, 2006, p. 5755, vol. 24.
Mossing et al., Upstream operators enhance repression of the lac promoter. Science, 1986, pp. 889-892, vol. 233, No. 4766.
Motin et al., Passive immunity to Yersiniae mediated by anti-recombinant V antigen and protein A-V antigen fusion peptide. Infect Immun, 1994, pp. 4192-4201, vol. 62.
Muller et al., Repression of lac promoter as a function of distance, phase and quality of an auxiliary lac operator. J Mol Biol, 1996, pp. 21-29, vol. 257, No. 1.
Muller-Hill et al., Mutants that mke more lac repressor. Proc Natl Acad Sci U S A, 1968, pp. 1259-1264, vol. 59, No. 4.
Muller-Hill, Lac repressor and lac operator. Prog Biophys Mol Biol, 1975, pp. 227-252, vol. 30, No. 2-3.
Nabors et al., Immunization of healthy adults with a single recombinant pneumococcal surface protein A (PspA) variant stimulates broadly cross-reactive antibodies to heterologous PspA molecules. Vaccine, 2000, p. 1743, vol. 18.
Nakayama et al., Construction of an Asd+ expression-cloning vector: stable maintenance and high level expression of cloned nucleic acid sequences in a *Salmonella* vaccine strain. BioTechnology, 1988, pp. 693-697, vol. 6.
Nedialkov et al., Resistance to lipopolysaccharide mediated by the Yersinia pestis V antigen-polyhistidine fusion peptide: amplification of interleukin-10. Infect Immun, 1997, pp. 1196-1203, vol. 65.
Neutra et al., Antigen sampling across epithelial barriers and induction of mucosal immune responses. Annu Rev Immunol, 1996, pp. 275-300, vol. 14.
O'Callaghan et al., High efficiency transformation of *Salmonella typhimurium* and *Salmonella typhi* by electroporation. Mol Gen Genet, 1990, pp. 156-158, vol. 223, No. 1.
Ortqvist et al., Randomised trial of 23-valent pneumococcal capsular polysaccharide vaccine in prevention of pneumonia in middle-aged and elderly people. Swedish Pneumococcal Vaccination Study Group. Lancet, 1998, pp. 399-403, vol. 3.
Perry et al., Temperature regulation of the hemin storage (Hms+) phenotype of Yersinia pestis is posttranscriptional. J Bacteriol, 2004, pp. 1638-1647, vol. 186.
Petersen et al., Essential role for cyclic AMP and its receptor protein in Yersinia enterocolitica virulence. Infect Immun, 2004, pp. 3665-3672, vol. 70.
Ramarathinam et al., *Salmonella typhimurium* induces IFN-gamma production in murine splenocytes. Role of natural killer cells and macrophages. J Immunol, 1993, pp. 3973-3981, vol. 150.
Raupach et al., Bacterial virulence, proinflammatory cytokines and host immunity: how to choose the appropriate *Salmonella* vaccine strain? Microbes and Infection, 2001, p. 1261, vol. 3.

Roland et al., Construction and evaluation of a delta cya delta crp *Salmonella typhimurium* strain expressing avian pathogenic *Escherichia coli* O78 LPS as a vaccine to prevent airsacculitis in chickens. Avian Dis, 1999, pp. 429-441, vol. 43, No. 3.
Sarubbi et al., (1989) Characterization of the spoT gene of *Escherichia coli*. J Biol Chem, 1989, pp. 15074-15082, vol. 264.
Schmieger et al., Altered cotransduction frequencies exhibited by HT-mutants of *Salmonella*-phage P22. Mol Gen Genet, 1976, pp. 307-309, vol. 143.
Schmieger, Phage P22-mutants with increased or decreased transduction abilities. Mol Gen Genet, 1972, pp. 75-88, vol. 119.
Schödel et al., Hybrid hepatitis B virus core antigen as a vaccine carrier moiety. II. Expression in avirulent *Salmonella* spp. for mucosal immunization. Adv Exp Med Biol., 1996, pp. 15-21, vol. 397.
Schodel, Prospects for oral vaccination using recombinant bacteria expressing viral epitopes. Adv. Virus Res., 1992, pp. 409-446, vol. 41.
Schwyn et al., Universal chemical assay for the detection and determination of siderophores. Analytical Biochemistry, 1987, p. 47, vol. 160.
Sedgwick et al., A solid-phase immunoenzymatic technique for the enumeration of specific antibody-secreting cells. Journal of Immunological Methods, 1983, p. 301, vol. 57.
Shalaby, Development of oral vaccines to stimulate mucosal and systemic immunity: barriers and novel strategies. Clin Immunol Immunopathol, 1995, pp. 127-134, vol. 74, No. 2.
Alonso et al, Anti-polysaccharide immunoglobulin isotype levels and opsonic activity of antisera: relationships with protection against *Streptococcus pneumoniae* infection in mice. J Infect Dis, 1995, pp. 562-565, vol. 172.
Amann et al., Tightly regulated tac promoter vectors useful for the expression of unfused and fused proteins in *Escherichia coli*. Nucleic acid sequence, 1988. pp. 301-315, vol. 69, No. 2.
Anderson et al., Delivery of the Pertactin/P.69 polypeptide of Bordetella pertussis using an attenuated *Salmonella typhimurium* vaccine strain: expression levels and immune response. Vaccine, 1996, pp. 1384-1390 , vol. 14, No. 14.
Aravind et al., The HD domain defines a new superfamily of metal-dependent phosphohydrolases. Trends Biochem Sci, 1998, pp. 469-472, vol. 23.
Arricau et al., The RcsB-RcsC regulatory system of *Salmonella typhi* differentially modulates the expression of invasion proteins, flagellin and Vi antigen in response to osmolarity., Mol Microbiol, 1998, pp. 85-50, vol. 29, No. 3.
Arulanandam et al., Intranasal vaccination with pneumococcal surface protein a and interleukin-12 augments antibody-mediated opsonization and protective immunity against *Streptococcus pneumoniae* infection. Infect Immun, 2001, pp. 6718-6724, vol. 69.
Audia et al., Breaking through the acid barrier: an orchestrated response to proton stress by enteric bacteria. Int J Med Microbiol, 2001, pp. 97-106, vol. 291.
Battesti et al., Acyl carrier protein/SpoT interaction, the switch linking SpoT-dependent stress response to fatty acid metabolism. Mol Microbiol, 2006, pp. 1048-1063, vol. 62.
Blattner et al., The complete genome sequence of *Escherichia coli* K-12. Science, 1997, pp. 1453-1474, vol. 277.
Branger et al., Oral vaccination with different antigens from Yersinia pestis KIM delivered by live attenuated *Salmonella typhimurium* elicits a protective immune response against plague. Adv Exp Med Biol, 2007, pp. 387-399, vol. 603.
Briles et al. The potential for using protein vaccines to protect against otitis media caused by *Streptococcus pneumoniae*. Vaccine, 2001, pp. S87-S95, vol. 19, Suppl 1.
Brubaker, Interleukin-10 and inhibition of innate immunity to Yersiniae: roles of Yops and LcrV (V antigen). Infect Immun, 2003, pp. 3673-3681, vol. 71.
Brubaker, The Vwa+ virulence factor of Yersiniae: the molecular basis of the attendant nutritional requirement for Ca2+. Rev Infect Dis, 1983,pp. S748-S758, vol. 5, Suppl 4.
Brumell et al., (2004) *Salmonella* redirects phagosomal maturation. Curr Opin Microbiol, 2004, pp. 78-84, vol. 7.

(56) References Cited

OTHER PUBLICATIONS

Cárdenas et al., Oral immunization using live attenuated *Salmonella* spp. as carriers of foreign antigens. Clin. Microbiol. Rev., 1992, pp. 328-342, vol. 5, No. 3.

Charnetzky et al., RNA synthesis in Yersinia pestis during growth restriction in calcium-deficient medium. J Bacteriol, 1982, pp. 108-195, vol. 149.

Chatfield et al., Use of the nirB promoter to direct the stable expression of heterologous antigens in *Salmonella* oral vaccine strains: development of a single-dose oral tetanus vaccine. Biotechnology (N Y), 1992, pp. 888-892, vol. 10, No. 8.

Cheng et al., Simultaneous analyses of neutral carbohydrates and amino sugars in freshwaters with HPLC—PAD. J. Chromatogr. Sci., 2003, pp. 434-438, vol. 41.

Chipman et al., The ACT domain family. Curr Opin Struct Biol, 2001, pp. 694-700, vol. 11.

Chromy et al., Proteomic characterization of Yersinia pestis virulence. J Bacteriol, 2005, pp. 8172-8180, vol. 187.

Coombes et al., SseL is a *Salmonella*-Specific Translocated Effector Integrated into the SsrB-Controlled *Salmonella* Pathogenicity Island 2 Type III Secretion System. Infection and Immunity, 2007, pp. 574-580, vol. 75, No. 2.

Cornelis et al., The virulence plasmid of Yersinia, an antihost genome. Microbiol Mol Biol Rev, 1998, pp. 1315-1352, vol. 62.

Curtiss et al. Nonrecombinant and recombinant avirulent *Salmonella* vaccines for poultry. Vet Immunol Immunopathol, 1996, pp. 365-372, vol. 54.

Curtiss et al., Live oral avirulent *Salmonella* vaccines. Vet. Microbiol., 1993, pp. 397-405, vol. 37.

Curtiss et al., Recombinant *Salmonella* vectors in vaccine development. Dev Biol Stand., 1994, pp. 23-33, vol. 82.

Datsenko et al., One-step inactivation of chromosomal genes in *Escherichia coli* K-12 using PCR products. Proc Natl Acad Sci U S A, 2000, pp. 6640-6645, vol. 97.

Davison, Towards safer vectors for the field release of recombinant bacteria. Environ. Biosafety Res., 2002, pp. 9-18, vol. 1.

De Groote et al., Homocysteine antagonism of nitric oxide-related cytostasis in *Salmonella typhimurium*. Science, 1996, pp. 414-417, vol. 272.

Dekruyff et al., Induction of immunoglobulin synthesis by CD4+ T cell clones. Seminars in Immunology, 1993, pp. 421-430, vol. 5.

Del Beccaro et al., Bacteriology of acute otitis media: a new perspective. J Pediatr, 1992, pp. 81-84, vol. 120.

Deng et al., Genome sequence of Yersinia pestis Kim. J Bacteriol, 2002, pp. 4601-4611, vol. 184.

Doggett et al., Delivery of antigens by recombinant avirulent *Salmonella* strains. Adv. Exp. Med. Biol., 1992, pp. 165-173, vol. 327.

Doublet et al., The murI gene of *Escherichia coli* is an essential gene that encodes a glutamate racemase activity. J. Bacteriol., 1993, pp. 2970-2979, vol. 175.

Dubnau, DNA uptake in bacteria. Annu. Rev. Microbiol., 1999, pp. 217-244, vol. 53.

Edwards et al., Improved allelic exchange vectors and their use to analyze 987P fimbria nucleic acid sequence expression. Gene, 1998, pp. 149-157, vol. 207, No. 2.

Fooks, Development of oral vaccines for human use. Curr Opin Mol Ther, 2000, pp. 80-86, vol. 2, No. 1.

Foster et al., How *Salmonella* survive against the odds. Annu Rev Microbiol, 1995, pp. 145-174, vol. 49.

Galen et al., Can a 'flawless' live vector vaccine strain be engineered? Trends Microbiol, 2001, pp. 372-376, vol. 9, No. 8.

Garmory et al., The Use of Live Attenuated Bacteria as a Delivery System for Heterologous Antigens. Journal of Drug Targeting, 2003, pp. 471, vol. 11.

Garzon et al., recB recJ mutants of *Salmonella typhimurium* are deficient in transductional recombination, DNA repair and plasmid maintenance. Mol. Gen. Genet., 1996, pp. 570-580, vol. 250.

Gentry et al., Mutational analysis of the *Escherichia coli* spoT gene identifies distinct but overlapping regions involved in ppGpp synthesis and degradation. Mol Microbiol, 1996, pp. 1373-1384, vol. 19.

Gentschev et al., The *E. coli* alpha-hemolysin secretion system and its use in vaccine development. Trends Microbiol, 2002, pp. 39-45, vol. 10, No. 1.

Giannella et al., Gastric acidity and cholera. Ann Intern Med, 1973, p. 780, vol. 78.

Gilbert, The lac repressor and the lac operator. Ciba Found Symp, 1972, pp. 24-59, vol. 7.

Gong et al., Characterization of the Yersinia pestis Yfu ABC inorganic iron transport system. Infect Immun, 2001, pp. 2829-2837, vol. 69.

Gor et al., TH1-TH2: a Procrustean paradigm. Nat Immunol, 2003, p. 503-5, vol. 4.

Grillot-Courvalin et al., Functional gene transfer from intracellular bacteria to mammalian cells. Nat. Biotechnol., 1998, pp. 862-866, vol. 16.

Guerrant et al., Magnitude and Impact of Diarrheal Diseases. Arch. Med. Res., 2002, pp. 351-355, vol. 33.

Gunn, Mechanisms of bacterial resistance and response to bile. Microbes Infect, 2000, pp. 907-913, vol. 2.

Hengge-Aronis et al., Identification and molecular analysis of glgS, a novel growth-phase-regulated and rpoSdependent gene involved in glycogen synthesis in *Escherichia coli*. Mol Microbiol, 1992, pp. 1877-1886, vol. 6.

\* cited by examiner

```
                        SEQUENCE LISTING

<160> NUMBER OF SEQ ID NOS: 58

<210> SEQ ID NO 1
<211> LENGTH: 417
<212> TYPE: PRT
<213> ORGANISM: Bacillus stearothermophilus

<400> SEQUENCE: 1

Met Met Lys Gly Cys Arg Val Met Val Val Leu Leu Gly Leu Cys Phe
1               5                   10                  15

Val Phe Gly Leu Ser Val Pro Gly Gly Arg Thr Glu Ala Ala Ser Leu
            20                  25                  30

Arg Ala Asn Asp Ala Pro Ile Val Leu Leu His Gly Phe Thr Gly Trp
        35                  40                  45

Gly Arg Glu Glu Met Phe Gly Phe Lys Tyr Trp Gly Gly Val Arg Gly
    50                  55                  60

Asp Ile Glu Gln Trp Leu Asn Asp Asn Gly Tyr Arg Thr Tyr Thr Leu
65                  70                  75                  80

Ala Val Gly Pro Leu Ser Ser Asn Trp Asp Arg Ala Cys Glu Ala Tyr
                85                  90                  95

Ala Gln Leu Val Gly Gly Thr Val Asp Tyr Gly Ala Ala His Ala Ala
            100                 105                 110

Lys His Gly His Ala Arg Phe Gly Arg Thr Tyr Pro Gly Leu Leu Pro
        115                 120                 125

Glu Leu Lys Arg Gly Gly Arg Ile His Ile Ile Ala His Ser Gln Gly
    130                 135                 140

Gly Gln Thr Ala Arg Met Leu Val Ser Leu Leu Glu Asn Gly Ser Gln
145                 150                 155                 160

Glu Glu Arg Glu Tyr Ala Lys Ala His Asn Val Ser Leu Ser Pro Leu
```

```
            165                 170                 175
Phe Glu Gly Gly His His Phe Val Leu Ser Val Thr Thr Ile Ala Thr
            180                 185                 190

Pro His Asp Gly Thr Thr Leu Val Asn Met Val Asp Phe Thr Asp Arg
        195                 200                 205

Phe Phe Asp Leu Gln Lys Ala Val Leu Glu Ala Ala Ala Val Ala Ser
    210                 215                 220

Asn Val Pro Tyr Thr Ser Gln Val Tyr Asp Phe Lys Leu Asp Gln Trp
225                 230                 235                 240

Gly Leu Arg Arg Gln Pro Gly Glu Ser Phe Asp His Tyr Phe Glu Arg
                245                 250                 255

Leu Lys Arg Ser Pro Val Trp Thr Ser Thr Asp Thr Ala Arg Tyr Asp
            260                 265                 270

Leu Ser Val Ser Gly Ala Glu Lys Leu Asn Gln Trp Val Gln Ala Ser
        275                 280                 285

Pro Asn Thr Tyr Tyr Leu Ser Phe Ser Thr Glu Arg Thr Tyr Arg Gly
    290                 295                 300

Ala Leu Thr Gly Asn His Tyr Pro Glu Leu Gly Met Asn Ala Phe Ser
305                 310                 315                 320

Ala Val Val Cys Ala Pro Phe Leu Gly Ser Tyr Arg Asn Pro Thr Leu
                325                 330                 335

Gly Ile Asp Ser His Trp Leu Glu Asn Asp Gly Ile Val Asn Thr Ile
            340                 345                 350

Ser Met Asn Gly Pro Lys Arg Gly Ser Asn Asp Arg Ile Val Pro Tyr
        355                 360                 365

Asp Gly Thr Leu Lys Lys Gly Val Trp Asn Asp Met Gly Thr Tyr Asn
    370                 375                 380

Val Asp His Leu Glu Ile Ile Gly Val Asp Pro Asn Pro Ser Phe Asp
385                 390                 395                 400

Ile Arg Ala Phe Tyr Leu Arg Leu Ala Glu Gln Leu Ala Ser Leu Gln
                405                 410                 415

Pro

<210> SEQ ID NO 2
<211> LENGTH: 418
<212> TYPE: PRT
<213> ORGANISM: Bacillus stearothermophilus

<400> SEQUENCE: 2

Met Met Lys Cys Cys Arg Arg Val Ala Leu Val Leu Leu Gly Leu Trp
1               5                   10                  15

Phe Val Phe Cys Ile Ser Val Leu Gly Gly Arg Ala Glu Ala Ala
            20                  25                  30

Ser Arg Ala Asn Asp Ala Pro Ile Val Leu Leu His Gly Phe Thr Gly
        35                  40                  45

Trp Gly Arg Glu Glu Met Phe Gly Phe Lys Tyr Trp Gly Gly Val Arg
    50                  55                  60

Gly Asp Ile Glu Gln Trp Leu Asn Asp Asn Gly Tyr Arg Thr Tyr Thr
65                  70                  75                  80

Leu Ala Val Gly Pro Leu Ser Ser Asn Trp Asp Arg Ala Cys Glu Ala
                85                  90                  95

Tyr Ala Gln Leu Val Gly Gly Thr Val Asp Tyr Gly Ala Ala His Ala
            100                 105                 110

Ala Lys His Gly His Ala Arg Phe Gly Arg Thr Tyr Pro Gly Leu Leu
```

```
            115                 120                 125
Pro Glu Leu Lys Arg Gly Gly Arg Ile His Ile Ala His Ser Gln
130                 135                 140

Gly Gly Gln Thr Ala Arg Met Leu Val Ser Leu Leu Glu Asn Gly Ser
145                 150                 155                 160

Gln Glu Glu Arg Glu Tyr Ala Lys Ala His Asn Val Ser Leu Ser Pro
                165                 170                 175

Leu Phe Glu Gly Gly His His Phe Val Leu Ser Val Thr Thr Ile Ala
                180                 185                 190

Thr Pro His Asp Gly Thr Thr Leu Val Asn Met Val Asp Phe Thr Asp
                195                 200                 205

Arg Phe Phe Asp Leu Gln Lys Ala Val Leu Lys Ala Ala Val Ala
210                 215                 220

Ser Asn Val Pro Tyr Thr Ser Gln Val Tyr Asp Phe Lys Leu Asp Gln
225                 230                 235                 240

Trp Gly Leu Arg Arg Gln Pro Gly Glu Ser Phe Asp Gln Tyr Phe Glu
                245                 250                 255

Arg Leu Lys Arg Ser Pro Val Trp Thr Ser Thr Asp Thr Ala Arg Tyr
                260                 265                 270

Asp Leu Ser Val Pro Gly Ala Glu Lys Leu Asn Gln Trp Val Lys Ala
                275                 280                 285

Ser Pro Asn Thr Tyr Tyr Leu Ser Phe Ala Thr Glu Arg Thr Tyr Arg
                290                 295                 300

Gly Ala Leu Thr Gly Asn Tyr Tyr Pro Glu Leu Gly Met Asn Ala Phe
305                 310                 315                 320

Ser Ala Val Val Cys Ala Pro Phe Leu Gly Ser Tyr Arg Asn Ala Thr
                325                 330                 335

Leu Gly Ile Asp Asp Arg Trp Leu Glu Asn Asp Gly Ile Val Asn Thr
                340                 345                 350

Phe Ser Met Asn Gly Pro Lys Arg Gly Ser Thr Asp Arg Ile Val Pro
                355                 360                 365

Tyr Asp Gly Thr Ile Lys Lys Gly Val Trp Asn Asp Met Gly Thr Tyr
370                 375                 380

Asn Val Asp His Leu Glu Val Ile Gly Val Asp Pro Asn Pro Leu Phe
385                 390                 395                 400

Asp Ile Arg Ala Phe Tyr Leu Arg Leu Ala Glu Gln Leu Ala Ser Leu
                405                 410                 415

Gln Pro

<210> SEQ ID NO 3
<211> LENGTH: 417
<212> TYPE: PRT
<213> ORGANISM: Geobacillus stearothemophilus

<400> SEQUENCE: 3

Met Met Lys Gly Cys Arg Val Met Phe Val Leu Leu Gly Leu Trp Leu
1               5                   10                  15

Val Phe Gly Leu Ser Val Pro Gly Gly Arg Ala Glu Ala Ala Thr Ser
                20                  25                  30

Arg Ala Asn Asp Ala Pro Ile Val Leu Leu His Gly Phe Thr Gly Trp
                35                  40                  45

Gly Arg Glu Glu Met Phe Gly Phe Lys Tyr Trp Gly Gly Val Arg Gly
            50                  55                  60

Asp Ile Glu Gln Trp Leu Asn Asp Asn Gly Tyr Arg Thr Tyr Thr Leu
```

```
            65                  70                  75                  80
    Ala Val Gly Pro Leu Ser Ser Asn Trp Asp Arg Ala Cys Glu Ala Tyr
                         85                  90                  95

Ala Gln Leu Val Gly Gly Thr Val Asp Tyr Gly Ala Ala His Ala Ala
                        100                 105                 110

Lys His Gly His Ala Arg Phe Gly Arg Thr Tyr Pro Gly Leu Leu Pro
                        115                 120                 125

Glu Leu Lys Arg Gly Gly Arg Ile His Ile Ala His Ser Gln Gly
                        130                 135                 140

Gly Gln Thr Ala Arg Met Leu Val Ser Leu Leu Glu Asn Gly Ser Gln
    145                 150                 155                 160

Glu Glu Arg Glu Tyr Ala Lys Ala His Asn Val Ser Leu Ser Pro Leu
                        165                 170                 175

Phe Glu Gly Gly His His Phe Val Leu Ser Val Thr Thr Ile Ala Thr
                        180                 185                 190

Pro His Asp Gly Thr Thr Leu Val Asn Met Val Asp Phe Thr Asp Arg
                        195                 200                 205

Phe Phe Asp Leu Gln Lys Ala Val Leu Glu Ala Ala Val Ala Ser
                        210                 215                 220

Asn Val Pro Tyr Thr Ser Gln Val Tyr Asp Phe Lys Leu Asp Gln Trp
    225                 230                 235                 240

Gly Leu Arg Arg Gln Pro Gly Glu Ser Phe Asp His Tyr Phe Glu Arg
                        245                 250                 255

Leu Lys Arg Ser Pro Val Trp Thr Ser Thr Ala Arg Tyr Asp
                        260                 265                 270

Leu Ser Val Ser Gly Ala Glu Lys Leu Asn Gln Trp Val Gln Ala Ser
                        275                 280                 285

Pro Asn Thr Tyr Tyr Leu Ser Phe Ala Thr Glu Arg Thr Tyr Arg Gly
                        290                 295                 300

Ala Leu Thr Gly Asn Tyr Tyr Pro Glu Leu Gly Met Asn Ala Phe Ser
    305                 310                 315                 320

Ala Val Val Cys Ala Pro Phe Leu Gly Ser Tyr Arg Asn Pro Thr Leu
                        325                 330                 335

Gly Ile Asp Asp Arg Trp Leu Glu Asn Asp Gly Ile Val Asn Thr Val
                        340                 345                 350

Ser Met Asn Gly Pro Lys Arg Gly Ser Ser Asp Arg Ile Val Pro Tyr
                        355                 360                 365

Asp Gly Ala Leu Lys Lys Gly Val Trp Asn Asp Met Gly Thr Tyr Asn
                        370                 375                 380

Val Asp His Leu Glu Ile Ile Gly Val Asp Pro Asn Pro Ser Phe Asp
    385                 390                 395                 400

Ile Arg Ala Phe Tyr Leu Arg Leu Ala Glu Gln Leu Ala Ser Leu Gln
                        405                 410                 415

Pro

<210> SEQ ID NO 4
    <211> LENGTH: 319
    <212> TYPE: PRT
    <213> ORGANISM: Geobacillus stearothemophilus

<400> SEQUENCE: 4

Gly Leu Val Val Gly Tyr Gly Leu Cys Ser Ala Tyr Arg Ser Arg Gly
    1                   5                   10                  15

Ala Ala Glu Ala Ala Ser Pro Arg Ala Asn Asp Ala Pro Ile Val Leu
```

```
            20                  25                  30
Leu His Gly Phe Thr Gly Trp Gly Arg Glu Glu Met Leu Gly Phe Lys
            35                  40                  45

Tyr Trp Gly Gly Val Arg Gly Asp Ile Glu Gln Trp Leu Asn Asp Asn
 50                  55                  60

Gly Tyr Arg Thr Tyr Thr Leu Ala Val Gly Pro Leu Ser Ser Asn Trp
 65                  70                  75                  80

Asp Arg Ala Cys Glu Ala Tyr Ala Gln Leu Val Gly Gly Thr Val Asp
                 85                  90                  95

Tyr Gly Ala Ala His Ala Ala Lys His Gly His Ala Arg Phe Gly Arg
                100                 105                 110

Pro Tyr Pro Gly Leu Leu Ala Gly Ile Glu Arg Arg Lys Pro Ala Ser
            115                 120                 125

Ile Gln Ser Val His Arg Pro Arg Glu Gly Arg Ala Gly Met Leu
            130                 135                 140

Gly Phe Arg Ser Leu Gly Glu Thr Gly Gly Gln Arg Arg Gly Gly Glu
145                 150                 155                 160

Tyr Ala Gln Gly Ser His Asn Arg Gly Arg Leu Val Gly Pro Phe Val
                165                 170                 175

Leu Arg Gly Gly His Pro Phe Leu Cys Arg Ala Val Thr Asp His Ser
            180                 185                 190

Gln Thr Pro Ser Gly Arg Glu Pro Thr Pro Cys Lys His Gly Leu Ile
            195                 200                 205

Ser Pro Asp Pro Leu Phe Leu Thr Cys Gln Lys Gly Gly Ala Trp Lys
            210                 215                 220

Arg Arg Leu Val Arg Gln Pro Thr Ala Pro Tyr His Lys Arg Asn Tyr
225                 230                 235                 240

Thr Ile Leu Ser Leu Gly Pro Met Gly Gly Leu Arg Arg Glu Pro Arg
                245                 250                 255

Arg Ile Arg Ser Thr Ile Tyr Phe Gly Thr Ala Gln Ala Pro Pro Leu
            260                 265                 270

Ser Gly His Arg Thr Arg Tyr Pro Pro Arg Tyr Asp Leu Ile Arg Ser
            275                 280                 285

Arg Gly Leu Arg Arg Gly Ile Arg Leu Gly Glu Ser Gln Pro Asn Thr
            290                 295                 300

Tyr Tyr Leu Glu Leu Phe Tyr Pro Asn Gly Arg Ile Glu Glu Leu
305                 310                 315

<210> SEQ ID NO 5
<211> LENGTH: 418
<212> TYPE: PRT
<213> ORGANISM: Geobacillus stearothemophilus

<400> SEQUENCE: 5

Met Met Lys Cys Cys Arg Arg Val Ala Leu Val Leu Gly Leu Trp
1               5                  10                  15

Phe Val Phe Cys Ile Ser Val Leu Gly Gly Arg Ala Glu Ala Ala
            20                  25                  30

Ser Arg Ala Asn Asp Ala Pro Ile Val Leu Leu His Gly Phe Thr Gly
            35                  40                  45

Trp Gly Arg Glu Glu Met Phe Gly Phe Lys Tyr Trp Gly Gly Val Arg
 50                  55                  60

Gly Asp Ile Glu Gln Trp Leu Asn Asp Asn Gly Tyr Arg Thr Tyr Thr
 65                  70                  75                  80
```

```
Leu Ala Val Gly Pro Leu Ser Ser Asn Trp Asp Arg Ala Cys Glu Ala
                 85                  90                  95

Tyr Ala Gln Leu Val Gly Gly Thr Val Asp Tyr Gly Ala Ala His Ala
            100                 105                 110

Ala Lys His Gly His Ala Arg Phe Gly Arg Thr Tyr Pro Gly Leu Leu
        115                 120                 125

Pro Glu Leu Lys Arg Gly Gly Arg Ile His Ile Ala His Ser Gln
130                 135                 140

Gly Gly Gln Thr Ala Arg Met Leu Val Ser Leu Glu Asn Gly Ser
145                 150                 155                 160

Gln Glu Glu Arg Glu Tyr Ala Lys Ala His Asn Val Ser Leu Ser Pro
                165                 170                 175

Leu Phe Glu Gly Gly His His Phe Val Leu Arg Val Thr Thr Ile Ala
            180                 185                 190

Thr Pro His Asp Gly Thr Thr Leu Val Asn Met Val Asp Phe Thr Asp
        195                 200                 205

Arg Phe Phe Asp Leu Gln Lys Ala Val Leu Lys Ala Ala Ala Val Ala
210                 215                 220

Ser Asn Val Pro Tyr Thr Ser Gln Val Tyr Asp Phe Lys Leu Asp Gln
225                 230                 235                 240

Trp Gly Leu Arg Arg Gln Pro Gly Glu Ser Phe Asp Gln Tyr Phe Glu
                245                 250                 255

Arg Leu Lys Arg Ser Pro Val Trp Thr Ser Asp Thr Ala Arg Tyr
            260                 265                 270

Asp Leu Ser Val Pro Gly Ala Glu Lys Leu Asn Gln Trp Val Lys Ala
        275                 280                 285

Ser Pro Asn Thr Tyr Tyr Leu Ser Phe Ala Thr Glu Arg Thr Tyr Arg
290                 295                 300

Gly Ala Leu Thr Gly Asn Tyr Tyr Pro Glu Leu Gly Met Asn Ala Phe
305                 310                 315                 320

Ser Ala Val Val Cys Ala Pro Phe Leu Gly Ser Tyr Arg Asn Ala Thr
                325                 330                 335

Leu Gly Ile Asp Asp Arg Trp Leu Glu Asn Asp Gly Ile Val Asn Thr
            340                 345                 350

Phe Ser Met Asn Gly Pro Lys Arg Gly Ser Thr Asp Arg Ile Val Pro
        355                 360                 365

Tyr Asp Gly Thr Ile Lys Lys Gly Val Trp Asn Asp Met Gly Thr Tyr
370                 375                 380

Asn Val Asp His Leu Glu Val Ile Gly Val Asp Pro Asn Pro Leu Phe
385                 390                 395                 400

Asp Ile Arg Ala Phe Tyr Leu Arg Leu Ala Glu Gln Leu Ala Ser Leu
                405                 410                 415

Gln Pro

<210> SEQ ID NO 6
<211> LENGTH: 417
<212> TYPE: PRT
<213> ORGANISM: Bacillus stearothermophilus

<400> SEQUENCE: 6

Met Met Lys Gly Cys Arg Val Met Val Val Leu Leu Gly Leu Trp Phe
1               5                   10                  15

Val Phe Gly Leu Ser Val Pro Gly Gly Arg Thr Glu Ala Ala Ser Pro
            20                  25                  30
```

```
Arg Ala Asn Asp Ala Pro Ile Val Leu Leu His Gly Phe Thr Gly Trp
             35                  40                  45

Gly Arg Glu Glu Met Leu Gly Phe Lys Tyr Trp Gly Gly Val Arg Gly
 50                  55                  60

Asp Ile Glu Gln Trp Leu Asn Asp Asn Gly Tyr Arg Thr Tyr Thr Leu
 65                  70                  75                  80

Ala Val Gly Pro Leu Ser Ser Asn Trp Asp Arg Ala Cys Glu Ala Tyr
                 85                  90                  95

Ala Gln Leu Val Gly Gly Thr Val Asp Tyr Gly Ala Ala His Ala Ala
            100                 105                 110

Asn Asp Gly His Ala Arg Phe Gly Arg Thr Tyr Pro Gly Leu Leu Pro
            115                 120                 125

Glu Leu Lys Arg Gly Gly Arg Val His Ile Ile Ala His Ser Gln Gly
130                 135                 140

Gly Gln Thr Ala Arg Met Leu Val Ser Leu Leu Glu Asn Gly Ser Gln
145                 150                 155                 160

Glu Glu Arg Glu Tyr Ala Lys Glu His Asn Val Ser Leu Ser Pro Leu
                165                 170                 175

Phe Glu Gly Gly His Arg Phe Val Leu Ser Val Thr Thr Ile Ala Thr
            180                 185                 190

Pro His Asp Gly Thr Thr Leu Val Asn Met Val Asp Phe Thr Asp Arg
            195                 200                 205

Phe Phe Asp Leu Gln Lys Ala Val Leu Glu Ala Ala Ala Val Ala Ser
210                 215                 220

Asn Ala Pro Tyr Thr Ser Glu Ile Tyr Asp Phe Lys Leu Asp Gln Trp
225                 230                 235                 240

Gly Leu Arg Arg Glu Pro Gly Glu Ser Phe Asp His Tyr Phe Glu Arg
                245                 250                 255

Leu Lys Arg Ser Pro Val Trp Thr Ser Thr Asp Thr Ala Arg Tyr Asp
            260                 265                 270

Leu Ser Val Pro Gly Ala Glu Thr Leu Asn Arg Trp Val Lys Ala Ser
            275                 280                 285

Pro Asn Thr Tyr Tyr Leu Ser Phe Ser Thr Glu Arg Thr Tyr Arg Gly
290                 295                 300

Ala Leu Thr Gly Asn Tyr Tyr Pro Glu Leu Gly Met Asn Ala Phe Ser
305                 310                 315                 320

Ala Ile Val Cys Ala Pro Phe Leu Gly Ser Tyr Arg Asn Ala Ala Leu
                325                 330                 335

Gly Ile Asp Ser His Trp Leu Gly Asn Asp Gly Ile Val Asn Thr Ile
            340                 345                 350

Ser Met Asn Gly Pro Lys Arg Gly Ser Asn Asp Arg Ile Val Pro Tyr
            355                 360                 365

Asp Gly Thr Leu Lys Lys Gly Val Trp Asn Asp Met Gly Thr Tyr Lys
370                 375                 380

Val Asp His Leu Glu Val Ile Gly Val Asp Pro Asn Pro Ser Phe Asn
385                 390                 395                 400

Ile Arg Ala Phe Tyr Leu Arg Leu Ala Glu Gln Leu Ala Ser Leu Arg
                405                 410                 415

Pro

<210> SEQ ID NO 7
<211> LENGTH: 291
<212> TYPE: PRT
<213> ORGANISM: Thermomyces lanuginosus
```

<400> SEQUENCE: 7

```
Met Arg Ser Ser Leu Val Leu Phe Phe Leu Ser Ala Trp Thr Ala Leu
1               5                   10                  15

Ala Arg Pro Val Arg Arg Ala Val Pro Gln Asp Leu Leu Asp Gln Phe
            20                  25                  30

Glu Leu Phe Ser Gln Tyr Ser Ala Ala Tyr Cys Ala Ala Asn Asn
        35                  40                  45

His Ala Pro Val Gly Ser Asp Val Thr Cys Ser Glu Asn Val Cys Pro
    50                  55                  60

Glu Val Asp Ala Ala Asp Ala Thr Phe Leu Tyr Ser Phe Glu Asp Ser
65                  70                  75                  80

Gly Leu Gly Asp Val Thr Gly Leu Leu Ala Leu Asp Asn Thr Asn Lys
                85                  90                  95

Leu Ile Val Leu Ser Phe Arg Gly Ser Arg Ser Val Glu Asn Trp Ile
            100                 105                 110

Ala Asn Leu Ala Ala Asp Leu Thr Glu Ile Ser Asp Ile Cys Ser Gly
        115                 120                 125

Cys Glu Gly His Val Gly Phe Val Thr Ser Trp Arg Ser Val Ala Asp
130                 135                 140

Thr Ile Arg Glu Gln Val Gln Asn Ala Val Asn Glu His Pro Asp Tyr
145                 150                 155                 160

Arg Val Val Phe Thr Gly His Ser Leu Gly Ala Leu Ala Thr Ile
                165                 170                 175

Ala Ala Ala Ala Leu Arg Gly Asn Gly Tyr Asn Ile Asp Val Phe Ser
        180                 185                 190

Tyr Gly Ala Pro Arg Val Gly Asn Arg Ala Phe Ala Glu Phe Leu Thr
            195                 200                 205

Ala Gln Thr Gly Gly Thr Leu Tyr Arg Ile Thr His Thr Asn Asp Ile
210                 215                 220

Val Pro Arg Leu Pro Pro Arg Asp Trp Gly Tyr Ser His Ser Ser Pro
225                 230                 235                 240

Glu Tyr Trp Val Thr Ser Gly Asn Asp Val Pro Val Thr Ala Asn Asp
                245                 250                 255

Ile Thr Val Val Glu Gly Ile Asp Ser Thr Asp Gly Asn Asn Gln Gly
            260                 265                 270

Asn Ile Pro Asp Ile Pro Ser His Leu Trp Tyr Phe Gly Pro Ile Ser
        275                 280                 285

Glu Cys Asp
290
```

<210> SEQ ID NO 8
<211> LENGTH: 563
<212> TYPE: PRT
<213> ORGANISM: Galactomyces geotrichum

<400> SEQUENCE: 8

```
Met Val Ser Lys Ser Phe Phe Leu Ala Ala Val Asn Val Val Gly
1               5                   10                  15

Val Leu Ala Gln Ala Pro Thr Ala Val Leu Asn Asp Asn Glu Val Ile
            20                  25                  30

Thr Gly Val Leu Glu Gly Gln Val Asp Thr Phe Lys Gly Ile Pro Phe
        35                  40                  45

Ala Asp Pro Pro Val Ala Asp Leu Arg Phe Lys His Pro Gln Ser Phe
    50                  55                  60
```

```
Thr Gly Ser Tyr Gln Gly Leu Gln Ala Lys Asp Phe Ser Ala Cys
 65                  70                  75                  80

Met Gln Ile Asp Pro Tyr Asn Ser Leu Thr Ile Leu Asp Asn Val Leu
             85                  90                  95

Asn Leu Gly Lys Ile Ile Pro Glu Asp Phe Arg Gly Pro Ile Tyr Asp
             100                 105                 110

Met Ala Lys Gly Thr Val Ser Met Ser Glu Asp Cys Leu Tyr Leu Asn
             115                 120                 125

Val Phe Arg Pro Ala Gly Thr Lys Pro Ser Asp Lys Leu Pro Val Met
     130                 135                 140

Val Trp Ile Tyr Gly Gly Ala Phe Ile Tyr Gly Ser Ser Ala Ala Tyr
 145                 150                 155                 160

Pro Gly Asn Gly Tyr Val Lys Glu Ser Val Lys Met Gly Gln Pro Val
             165                 170                 175

Val Phe Val Ser Ile Asn Tyr Arg Thr Gly Pro Phe Gly Phe Leu Gly
             180                 185                 190

Gly Asp Gly Ile Thr Ala Glu Gly Asn Thr Asn Ser Gly Leu His Asp
             195                 200                 205

Gln Arg Lys Gly Leu Glu Trp Val Ser Asp Asn Ile Ala Asn Phe Gly
     210                 215                 220

Gly Asp Pro Asp Lys Val Met Ile Phe Gly Glu Ser Ala Gly Ala Met
 225                 230                 235                 240

Ser Val Gly His Gln Leu Ile Ala Tyr Gly Gly Asp Asn Thr Tyr Asn
             245                 250                 255

Gly Lys Pro Leu Phe His Ser Ala Ile Leu Gln Ser Gly Gly Pro Leu
             260                 265                 270

Pro Tyr Tyr Asp Ser Thr Ser Val Gly Pro Glu Lys Ala Tyr Asn Arg
             275                 280                 285

Phe Ala Glu Tyr Ala Gly Cys Asp Thr Thr Ala Ser Asp Val Asp Ile
 290                 295                 300

Leu Gln Cys Leu Arg Ser Lys Ser Ser Gln Val Leu His Asp Ala Gln
 305                 310                 315                 320

Asn Ser Tyr Asp Leu Lys Asp Leu Phe Gly Leu Pro Glu Phe Leu
             325                 330                 335

Gly Phe Gly Pro Arg Pro Asp Gly Asp Ile Leu Pro Gly Ser Ala Phe
             340                 345                 350

Glu Leu Tyr Arg Ser Gly Arg Tyr Ala Lys Val Pro Tyr Ile Thr Gly
             355                 360                 365

Asn Gln Glu Asp Glu Gly Thr Val Leu Ala Pro Val Ala Leu Asn Ala
             370                 375                 380

Thr Thr Thr Pro His Val Lys Lys Trp Leu Gln Tyr Ile Phe Asn Gln
 385                 390                 395                 400

Ala Ser Asp Ser Ser Ile Glu Arg Val Leu Glu Leu Tyr Pro Gln Thr
             405                 410                 415

Leu Ser Glu Gly Ser Pro Phe Arg Thr Gly Ile Leu Asn Ala Leu Thr
             420                 425                 430

Pro Gln Phe Lys Arg Val Ala Ala Ile Leu Ser Asp Leu Leu Phe Gln
             435                 440                 445

Ser Pro Arg Arg Ile Met Leu Asn Ala Thr Lys Asp Val Asn Arg Trp
     450                 455                 460

Thr Tyr Ile Ser Thr His Leu His Asn Leu Val Pro Phe Leu Gly Thr
 465                 470                 475                 480
```

```
Phe His Gly Asn Glu Leu Val Ile Gln Phe Asn Val Asn Val Gly Pro
                485                 490                 495

Ala Asp Ser Tyr Leu Arg Tyr Phe Ile Ser Phe Ala Asn His His Asp
            500                 505                 510

Pro Asn Val Gly Thr Asn Leu Leu Thr Trp Asn Lys Tyr Thr Asp Glu
            515                 520                 525

Gly Lys Glu Met Leu Glu Ile Lys Met Phe Asp Asn Ser Met Arg Thr
            530                 535                 540

Asp Asp Phe Arg Ile Glu Gly Ile Ser Asn Phe Glu Ser Asp Val Asn
545                 550                 555                 560

Leu Tyr Gly

<210> SEQ ID NO 9
<211> LENGTH: 417
<212> TYPE: PRT
<213> ORGANISM: Geobacillus thermocatenulatus

<400> SEQUENCE: 9

Met Met Lys Gly Cys Arg Val Met Val Leu Leu Gly Leu Trp Phe
1               5                   10                  15

Val Phe Gly Leu Ser Val Pro Gly Gly Arg Thr Glu Ala Ala Ser Pro
            20                  25                  30

Arg Ala Asn Asp Ala Pro Ile Val Leu Leu His Gly Phe Thr Gly Trp
        35                  40                  45

Gly Arg Glu Glu Met Leu Gly Phe Lys Tyr Trp Gly Gly Val Arg Gly
    50                  55                  60

Asp Ile Glu Gln Trp Leu Asn Asp Asn Gly Tyr Arg Thr Tyr Thr Leu
65                  70                  75                  80

Ala Val Gly Pro Leu Ser Ser Asn Trp Asp Arg Ala Cys Glu Ala Tyr
                85                  90                  95

Ala Gln Leu Val Gly Gly Thr Val Asp Tyr Gly Ala Ala His Ala Ala
            100                 105                 110

Lys His Gly His Ala Arg Phe Gly Arg Thr Tyr Pro Gly Leu Leu Pro
        115                 120                 125

Glu Leu Lys Arg Gly Gly Arg Val His Ile Ile Ala His Ser Gln Gly
    130                 135                 140

Gly Gln Thr Ala Arg Met Leu Val Ser Leu Leu Glu Asn Gly Ser Gln
145                 150                 155                 160

Glu Glu Arg Glu Tyr Ala Lys Ala His Asn Val Ser Leu Ser Pro Leu
                165                 170                 175

Phe Glu Gly Gly His His Phe Val Leu Ser Val Thr Thr Ile Ala Thr
            180                 185                 190

Pro His Asp Gly Thr Thr Leu Val Asn Met Val Asp Phe Thr Asp Arg
        195                 200                 205

Phe Phe Asp Leu Gln Lys Ala Val Leu Lys Ala Ala Val Ala Ser
    210                 215                 220

Asn Val Pro Tyr Thr Ser Gln Val Tyr Asp Phe Lys Leu Asp Gln Trp
225                 230                 235                 240

Gly Leu Arg Arg Gln Pro Gly Glu Ser Phe Asp His Tyr Phe Glu Arg
                245                 250                 255

Leu Lys Arg Ser Pro Val Trp Thr Ser Thr Asp Thr Ala Arg Tyr Asp
            260                 265                 270

Leu Ser Ile Pro Gly Ala Glu Lys Leu Asn Gln Trp Val Gln Ala Ser
        275                 280                 285
```

```
Pro Asn Thr Tyr Tyr Leu Ser Phe Ser Thr Glu Arg Thr His Arg Gly
            290                 295                 300
Ala Leu Thr Gly Asn Tyr Tyr Pro Glu Leu Gly Met Asn Ala Phe Ser
305                 310                 315                 320
Ala Val Val Cys Ala Pro Phe Leu Gly Ser Tyr Arg Asn Glu Ala Leu
                325                 330                 335
Gly Ile Asp Asp Arg Trp Leu Glu Asn Asp Gly Ile Val Asn Thr Val
            340                 345                 350
Ser Met Asn Gly Pro Lys Arg Gly Ser Ser Asp Arg Ile Val Pro Tyr
            355                 360                 365
Asp Gly Thr Leu Lys Lys Gly Val Trp Asn Asp Met Gly Thr Cys Asn
370                 375                 380
Val Asp His Leu Glu Val Ile Gly Val Asp Pro Asn Pro Ser Phe Asp
385                 390                 395                 400
Ile Arg Ala Phe Tyr Leu Arg Leu Ala Glu Gln Leu Ala Ser Leu Arg
                405                 410                 415
Pro

<210> SEQ ID NO 10
<211> LENGTH: 416
<212> TYPE: PRT
<213> ORGANISM: Geobacillus thermoleovorans

<400> SEQUENCE: 10

Met Lys Cys Cys Arg Val Met Phe Val Leu Leu Gly Leu Trp Leu Val
1               5                   10                  15
Phe Gly Leu Ser Val Ser Gly Gly Arg Ala Glu Ala Ala Ser Arg
            20                  25                  30
Ala Asn Asp Ala Pro Ile Val Leu Leu His Gly Phe Thr Gly Trp Gly
            35                  40                  45
Arg Glu Glu Met Phe Gly Phe Lys Tyr Trp Gly Gly Val Arg Gly Asp
50                  55                  60
Ile Glu Gln Trp Leu Asn Asp Asn Gly Tyr Arg Thr Tyr Thr Leu Ala
65                  70                  75                  80
Val Gly Pro Leu Ser Ser Asn Trp Asp Arg Ala Cys Glu Ala Tyr Ala
                85                  90                  95
Gln Leu Val Gly Gly Thr Val Asp Tyr Gly Ala Ala His Ala Ala Lys
            100                 105                 110
His Gly His Ala Arg Phe Gly Arg Thr Tyr Pro Gly Leu Leu Pro Glu
            115                 120                 125
Leu Lys Arg Gly Gly Arg Ile His Ile Ile Ala His Ser Gln Gly Gly
            130                 135                 140
Gln Thr Ala Arg Met Leu Val Ser Leu Leu Glu Asn Gly Ser Gln Glu
145                 150                 155                 160
Glu Arg Glu Tyr Ala Lys Ala His Asn Val Ser Leu Ser Pro Leu Phe
                165                 170                 175
Glu Gly Gly His His Phe Val Leu Ser Val Thr Thr Ile Ala Thr Pro
            180                 185                 190
His Asp Gly Thr Thr Leu Val Asn Met Val Asp Phe Thr Asp Arg Phe
            195                 200                 205
Phe Asp Leu Gln Lys Ala Val Leu Glu Ala Ala Val Ala Ser Asn
            210                 215                 220
Val Pro Tyr Thr Ser Gln Val Tyr Asp Phe Lys Leu Asp Gln Trp Gly
225                 230                 235                 240
```

Leu Arg Arg Gln Pro Gly Glu Ser Phe Asp His Tyr Phe Glu Arg Leu
            245                 250                 255

Lys Arg Ser Pro Val Trp Thr Ser Thr Asp Thr Ala Arg Tyr Asp Leu
        260                 265                 270

Ser Val Ser Gly Ala Glu Lys Leu Asn Gln Trp Val Gln Ala Ser Pro
    275                 280                 285

Asn Thr Tyr Tyr Leu Ser Phe Ala Thr Glu Arg Thr Tyr Arg Gly Ala
290                 295                 300

Leu Thr Gly Asn Tyr Tyr Pro Glu Leu Gly Met Asn Ala Phe Ser Ala
305                 310                 315                 320

Val Val Cys Ala Pro Phe Leu Gly Ser Tyr Arg Asn Pro Thr Leu Gly
                325                 330                 335

Ile Asp Asp Arg Trp Leu Glu Asn Asp Gly Ile Val Asn Thr Val Ser
            340                 345                 350

Met Asn Gly Pro Lys Arg Gly Ser Ser Asp Arg Ile Val Pro Tyr Asp
        355                 360                 365

Gly Ala Leu Lys Lys Gly Val Trp Asn Asp Met Gly Thr Tyr Asn Val
    370                 375                 380

Asp His Leu Glu Ile Ile Gly Val Asp Pro Asn Pro Ser Phe Asp Ile
385                 390                 395                 400

Arg Ala Phe Tyr Leu Arg Leu Ala Glu Gln Leu Ala Ser Leu Arg Pro
                405                 410                 415

<210> SEQ ID NO 11
<211> LENGTH: 416
<212> TYPE: PRT
<213> ORGANISM: Geobacillus thermoleovorans

<400> SEQUENCE: 11

Met Lys Gly Cys Arg Val Met Phe Val Leu Leu Gly Leu Trp Leu Val
1               5                   10                  15

Phe Gly Leu Ser Val Pro Gly Gly Arg Ala Glu Ala Ala Thr Ser Arg
            20                  25                  30

Ala Asn Asp Ala Pro Ile Val Leu His Gly Phe Thr Gly Trp Gly
        35                  40                  45

Arg Glu Glu Met Phe Gly Phe Lys Tyr Trp Gly Gly Val Arg Gly Asp
    50                  55                  60

Ile Glu Gln Trp Leu Asn Asp Asn Gly Tyr Arg Thr Tyr Thr Leu Ala
65                  70                  75                  80

Val Gly Pro Leu Ser Ser Asn Trp Asp Arg Ala Cys Glu Ala Tyr Ala
                85                  90                  95

Gln Leu Val Gly Gly Thr Val Asp Tyr Gly Ala Ala His Ala Ala Lys
            100                 105                 110

His Gly His Ala Arg Phe Gly Arg Thr Tyr Pro Gly Leu Leu Pro Glu
        115                 120                 125

Leu Lys Arg Gly Gly Arg Ile His Ile Ile Ala His Ser Gln Gly Gly
    130                 135                 140

Gln Thr Ala Arg Met Leu Val Ser Leu Leu Glu Asn Gly Ser Gln Glu
145                 150                 155                 160

Glu Arg Glu Tyr Ala Lys Ala His Asn Val Ser Leu Ser Pro Leu Phe
                165                 170                 175

Glu Gly Gly His His Phe Val Leu Ser Val Thr Thr Ile Ala Thr Pro
            180                 185                 190

His Asp Gly Thr Thr Leu Val Asn Met Val Asp Phe Thr Asp Arg Phe
        195                 200                 205

```
Phe Asp Leu Gln Lys Ala Val Leu Glu Ala Ala Ala Val Ala Ser Asn
    210                 215                 220

Ala Pro Tyr Thr Ser Glu Ile Tyr Asp Phe Lys Leu Asp Gln Trp Gly
225                 230                 235                 240

Leu Arg Arg Glu Pro Gly Glu Ser Phe Asp His Tyr Phe Glu Arg Leu
                245                 250                 255

Lys Arg Ser Pro Val Trp Thr Ser Thr Asp Thr Ala Arg Tyr Asp Leu
                260                 265                 270

Ser Val Pro Gly Ala Glu Thr Leu Asn Arg Trp Val Lys Ala Ser Pro
            275                 280                 285

Asn Thr Tyr Tyr Leu Ser Phe Ser Thr Glu Arg Thr Tyr Arg Gly Ala
        290                 295                 300

Leu Thr Gly Asn Tyr Tyr Pro Glu Leu Gly Met Asn Ala Phe Ser Ala
305                 310                 315                 320

Ile Val Cys Ala Pro Phe Leu Gly Ser Tyr Arg Asn Ala Ala Leu Gly
                325                 330                 335

Ile Asp Ser His Trp Leu Glu Asn Asp Gly Ile Val Asn Thr Ile Ser
                340                 345                 350

Met Asn Gly Pro Lys Arg Gly Ser Ser Asp Arg Ile Val Pro Tyr Asp
            355                 360                 365

Gly Ala Leu Lys Lys Gly Val Trp Asn Asp Met Gly Thr Tyr Asn Val
        370                 375                 380

Asp His Leu Glu Ile Ile Gly Val Asp Pro Asn Pro Ser Phe Asp Ile
385                 390                 395                 400

Arg Ala Phe Tyr Leu Arg Leu Ala Glu Gln Leu Ala Ser Phe Gly Pro
                405                 410                 415

<210> SEQ ID NO 12
<211> LENGTH: 416
<212> TYPE: PRT
<213> ORGANISM: Geobacillus thermoleovorans

<400> SEQUENCE: 12

Met Lys Cys Cys Arg Val Met Phe Val Leu Leu Gly Leu Trp Leu Val
1               5                   10                  15

Phe Gly Leu Ser Val Ser Gly Gly Arg Ala Glu Ala Ala Ala Ser Arg
            20                  25                  30

Ala Asn Asp Ala Pro Ile Val Leu Leu His Gly Phe Thr Gly Trp Gly
        35                  40                  45

Arg Glu Glu Met Phe Gly Phe Lys Tyr Trp Gly Gly Val Arg Gly Asp
50                  55                  60

Ile Glu Gln Trp Leu Asn Asp Asn Gly Tyr Arg Thr Tyr Thr Leu Ala
65                  70                  75                  80

Val Gly Pro Leu Ser Ser Asn Trp Asp Arg Ala Cys Glu Ala Tyr Ala
                85                  90                  95

Gln Leu Val Gly Gly Thr Val Asp Tyr Gly Ala Ala His Ala Ala Lys
            100                 105                 110

His Gly His Ala Arg Phe Gly Arg Thr Tyr Pro Gly Leu Leu Pro Glu
        115                 120                 125

Leu Lys Arg Gly Gly Arg Ile His Ile Ile Ala His Ser Gln Gly Gly
    130                 135                 140

Gln Thr Ala Arg Met Leu Val Ser Leu Leu Glu Asn Gly Ser Gln Glu
145                 150                 155                 160

Glu Arg Glu Tyr Ala Lys Ala His Asn Val Ser Leu Ser Pro Leu Phe
```

```
                    165                 170                 175
Glu Gly Gly His His Phe Val Leu Ser Val Thr Thr Ile Ala Thr Pro
                180                 185                 190

His Asp Gly Thr Thr Leu Val Asn Met Val Asp Phe Thr Asp Arg Phe
            195                 200                 205

Phe Asp Leu Gln Lys Ala Val Leu Glu Ala Ala Val Ala Ser Asn
        210                 215                 220

Val Pro Tyr Thr Ser Gln Val Tyr Asp Phe Lys Leu Asp Gln Trp Gly
225                 230                 235                 240

Leu Arg Arg Gln Pro Gly Glu Ser Phe Asp His Tyr Phe Glu Arg Leu
                245                 250                 255

Lys Arg Ser Pro Val Trp Thr Ser Thr Asp Thr Ala Arg Tyr Asp Leu
                260                 265                 270

Ser Val Ser Gly Ala Glu Lys Leu Asn Gln Trp Val Gln Ala Ser Pro
                275                 280                 285

Asn Thr Tyr Tyr Leu Ser Phe Ala Thr Glu Arg Thr Tyr Arg Gly Ala
            290                 295                 300

Leu Thr Gly Asn Tyr Tyr Pro Glu Leu Gly Met Asn Ala Phe Ser Ala
305                 310                 315                 320

Val Val Cys Ala Pro Phe Leu Gly Ser Tyr Arg Asn Pro Thr Leu Gly
                325                 330                 335

Ile Asp Asp Arg Trp Leu Glu Asn Asp Gly Ile Val Asn Thr Val Ser
                340                 345                 350

Met Asn Gly Pro Lys Arg Gly Ser Ser Asp Arg Ile Val Pro Tyr Asp
                355                 360                 365

Gly Ala Leu Lys Lys Gly Val Trp Asn Asp Met Gly Thr Tyr Asn Val
                370                 375                 380

Asp His Leu Glu Ile Ile Gly Val Asp Pro Asn Pro Ser Phe Asp Ile
385                 390                 395                 400

Arg Ala Phe Tyr Leu Arg Leu Ala Glu Gln Leu Ala Ser Leu Arg Pro
                405                 410                 415

<210> SEQ ID NO 13
<211> LENGTH: 416
<212> TYPE: PRT
<213> ORGANISM: Geobacillus thermoleovorans

<400> SEQUENCE: 13

Met Lys Cys Cys Arg Val Met Phe Val Leu Leu Gly Leu Trp Leu Val
1               5                   10                  15

Phe Gly Leu Ser Val Pro Gly Gly Arg Ala Glu Ala Ala Thr Ser Arg
                20                  25                  30

Ala Asn Asp Ala Pro Ile Val Leu Leu His Gly Phe Thr Gly Trp Gly
            35                  40                  45

Arg Glu Glu Met Phe Gly Phe Lys Tyr Trp Gly Gly Val Arg Gly Asp
        50                  55                  60

Ile Glu Gln Trp Leu Asn Asp Asn Gly Tyr Arg Thr Tyr Thr Leu Ala
65                  70                  75                  80

Val Gly Pro Leu Ser Ser Asn Trp Asp Arg Ala Cys Glu Ala Tyr Ala
                85                  90                  95

Gln Leu Val Gly Gly Thr Val Asp Tyr Gly Ala Ala His Ala Ala Lys
            100                 105                 110

His Gly His Ala Arg Phe Gly Arg Thr Tyr Pro Gly Leu Leu Pro Glu
        115                 120                 125
```

-continued

Leu Lys Arg Gly Gly Arg Ile His Ile Ile Ala His Ser Gln Gly Gly
130                 135                 140

Gln Thr Ala Arg Met Leu Val Ser Leu Leu Glu Asn Gly Ser Gln Glu
145                 150                 155                 160

Glu Arg Glu Tyr Ala Lys Ala His Asn Val Ser Leu Ser Pro Leu Phe
                165                 170                 175

Glu Gly Gly His His Phe Val Leu Ser Val Thr Thr Ile Ala Thr Pro
            180                 185                 190

His Asp Gly Thr Thr Leu Val Asn Met Val Asp Phe Thr Asp Arg Phe
        195                 200                 205

Phe Asp Leu Gln Lys Ala Val Leu Glu Ala Ala Val Ala Ser Asn
210                 215                 220

Ala Pro Tyr Thr Ser Glu Ile Tyr Asp Phe Lys Leu Asp Gln Trp Gly
225                 230                 235                 240

Leu Arg Arg Glu Pro Gly Glu Ser Phe Asp His Tyr Phe Glu Arg Leu
                245                 250                 255

Lys Arg Ser Pro Val Trp Thr Ser Thr Asp Thr Ala Arg Tyr Asp Leu
            260                 265                 270

Ser Val Pro Gly Ala Glu Thr Leu Asn Arg Trp Val Lys Ala Ser Pro
        275                 280                 285

Asn Thr Tyr Tyr Leu Ser Phe Ser Thr Glu Arg Thr Tyr Arg Gly Ala
290                 295                 300

Leu Thr Gly Asn Tyr Tyr Pro Glu Phe Gly Met Asn Ala Phe Ser Ala
305                 310                 315                 320

Ile Val Cys Ala Pro Phe Phe Gly Ser Tyr Arg Asn Ala Ala Leu Gly
                325                 330                 335

Ile Asp Ser His Trp Leu Glu Asn Asp Gly Ile Val Asn Thr Ile Ser
            340                 345                 350

Met Asn Gly Pro Lys Arg Gly Ser Ser Asp Arg Ile Val Pro Tyr Asp
        355                 360                 365

Gly Ala Leu Lys Lys Gly Val Trp Asn Asp Met Gly Thr Tyr Asn Val
370                 375                 380

Asp His Leu Glu Ile Ile Gly Val Asp Pro Asn Pro Ser Phe Asp Ile
385                 390                 395                 400

Arg Ala Phe Tyr Leu Arg Leu Ala Glu Gln Leu Ala Ser Leu Arg Pro
                405                 410                 415

<210> SEQ ID NO 14
<211> LENGTH: 416
<212> TYPE: PRT
<213> ORGANISM: Geobacillus thermoleovorans

<400> SEQUENCE: 14

Met Lys Gly Cys Arg Val Met Phe Val Leu Leu Gly Leu Trp Leu Val
1               5                   10                  15

Phe Gly Leu Ser Val Pro Gly Arg Ala Glu Ala Ala Thr Ser Arg
                20                  25                  30

Ala Asn Asp Ala Pro Ile Val Leu Leu His Gly Phe Thr Gly Trp Gly
            35                  40                  45

Arg Glu Glu Met Phe Gly Phe Lys Tyr Trp Gly Val Arg Gly Asp
        50                  55                  60

Ile Glu Gln Trp Leu Asn Asp Asn Gly Tyr Arg Thr Tyr Thr Leu Ala
65                  70                  75                  80

Val Gly Pro Leu Ser Ser Asn Trp Asp Arg Ala Cys Glu Ala Tyr Ala
                85                  90                  95

```
Gln Leu Val Gly Gly Thr Val Asp Tyr Gly Ala Ala His Ala Ala Lys
                100                 105                 110

His Gly His Ala Arg Phe Gly Arg Thr Tyr Pro Gly Leu Leu Pro Glu
            115                 120                 125

Leu Lys Arg Gly Gly Arg Ile His Ile Ile Ala His Ser Gln Gly Gly
        130                 135                 140

Gln Thr Ala Arg Met Leu Val Ser Leu Leu Glu Asn Gly Ser Gln Glu
145                 150                 155                 160

Glu Arg Glu Tyr Ala Lys Ala His Asn Val Ser Leu Ser Pro Leu Phe
                165                 170                 175

Glu Gly Gly His His Phe Val Leu Ser Val Thr Thr Ile Ala Thr Pro
            180                 185                 190

His Asp Gly Thr Thr Leu Val Asn Met Val Asp Phe Thr Asp Arg Phe
        195                 200                 205

Phe Asp Leu Gln Lys Ala Val Leu Glu Ala Ala Val Ala Ser Asn
210                 215                 220

Ala Pro Tyr Thr Ser Glu Ile Tyr Asp Phe Lys Leu Asp Gln Trp Gly
225                 230                 235                 240

Leu Arg Arg Glu Pro Gly Glu Ser Phe Asp His Tyr Phe Glu Arg Leu
                245                 250                 255

Lys Arg Ser Pro Val Trp Thr Ser Thr Asp Thr Ala Arg Tyr Asp Leu
            260                 265                 270

Ser Val Pro Gly Ala Glu Thr Leu Asn Arg Trp Val Lys Ala Ser Pro
        275                 280                 285

Asn Thr Tyr Tyr Leu Ser Phe Ser Thr Glu Arg Thr Tyr Arg Gly Ala
290                 295                 300

Leu Thr Gly Asn Tyr Tyr Pro Glu Leu Gly Met Asn Ala Phe Ser Ala
305                 310                 315                 320

Ile Val Cys Ala Pro Phe Leu Gly Ser Tyr Arg Asn Ala Ala Leu Gly
                325                 330                 335

Ile Asp Ser His Trp Leu Glu Asn Asp Gly Ile Val Asn Thr Ile Ser
            340                 345                 350

Met Asn Gly Pro Lys Arg Gly Ser Ser Asp Arg Ile Val Pro Tyr Asp
        355                 360                 365

Gly Ala Leu Lys Lys Gly Val Trp Asn Asp Met Gly Thr Tyr Asn Val
370                 375                 380

Asp His Leu Glu Ile Ile Gly Val Asp Pro Asn Pro Ser Phe Asp Ile
385                 390                 395                 400

Arg Ala Phe Tyr Leu Arg Leu Ala Glu Gln Leu Ala Ser Phe Gly Pro
                405                 410                 415

<210> SEQ ID NO 15
<211> LENGTH: 405
<212> TYPE: PRT
<213> ORGANISM: Bacillus sp. NG-27

<400> SEQUENCE: 15

Met Leu Lys Thr Leu Arg Lys Pro Phe Ile Ala Gly Leu Ala Leu Ser
1               5                   10                  15

Leu Leu Leu Thr Gly Gly Ala Ser Ser Val Phe Ala Gln Gly Asn Gly
                20                  25                  30

Gln Ala Gly Pro Pro Lys Gly Gly Ile Phe Lys Glu Gly Glu Lys Gly
            35                  40                  45

Asn Gly Asn Val Gln Pro Phe Ala Trp Gln Val Ala Ser Leu Ala Asp
```

```
            50                  55                  60
Arg Tyr Glu Glu Ser Phe Asp Ile Gly Ala Ala Val Glu Pro His Gln
 65                  70                  75                  80

Leu Asn Gly Arg Gln Gly Lys Val Leu Lys His His Tyr Asn Ser Ile
                 85                  90                  95

Val Ala Glu Asn Ala Met Lys Pro Ile Ser Leu Gln Pro Glu Glu Gly
                100                 105                 110

Val Phe Thr Trp Asp Gly Ala Asp Ala Ile Val Glu Phe Ala Arg Lys
                115                 120                 125

Asn Asn Met Asn Leu Arg Phe His Thr Leu Val Trp His Asn Gln Val
130                 135                 140

Pro Asp Trp Phe Phe Leu Asp Glu Glu Gly Asn Pro Met Val Glu Glu
145                 150                 155                 160

Thr Asn Glu Ala Lys Arg Gln Ala Asn Lys Glu Leu Leu Leu Glu Arg
                165                 170                 175

Leu Glu Thr His Ile Lys Thr Val Val Glu Arg Tyr Lys Asp Asp Val
                180                 185                 190

Thr Ala Trp Asp Val Val Asn Glu Val Val Asp Asp Gly Thr Pro Asn
                195                 200                 205

Glu Arg Gly Leu Arg Glu Ser Val Trp Tyr Gln Ile Thr Gly Asp Glu
210                 215                 220

Tyr Ile Arg Val Ala Phe Glu Thr Ala Arg Lys Tyr Ala Gly Glu Asp
225                 230                 235                 240

Ala Lys Leu Phe Ile Asn Asp Tyr Asn Thr Glu Val Thr Pro Lys Arg
                245                 250                 255

Asp His Leu Tyr Asn Leu Val Gln Asp Leu Leu Ala Asp Gly Val Pro
                260                 265                 270

Ile Asp Gly Val Gly His Gln Ala His Ile Gln Ile Asp Trp Pro Thr
                275                 280                 285

Ile Asp Glu Ile Arg Thr Ser Met Glu Met Phe Ala Gly Leu Gly Leu
                290                 295                 300

Asp Asn Gln Val Thr Glu Leu Asp Val Ser Leu Tyr Gly Trp Pro Pro
305                 310                 315                 320

Arg Pro Ala Phe Pro Thr Tyr Asp Ala Ile Pro Gln Glu Arg Phe Gln
                325                 330                 335

Ala Gln Ala Asp Arg Tyr Asn Gln Leu Phe Glu Leu Tyr Glu Glu Leu
                340                 345                 350

Asp Ala Asp Leu Ser Ser Val Thr Phe Trp Gly Ile Ala Asp Asn His
                355                 360                 365

Thr Trp Leu Asp Asp Arg Ala Arg Glu Tyr Asn Asp Gly Val Gly Lys
370                 375                 380

Asp Ala Pro Phe Val Phe Asp Pro Asn Tyr Arg Val Lys Pro Ala Phe
385                 390                 395                 400

Trp Arg Ile Ile Asp
                405

<210> SEQ ID NO 16
<211> LENGTH: 308
<212> TYPE: PRT
<213> ORGANISM: Artificial Sequence
<220> FEATURE:
<223> OTHER INFORMATION: uncultured bacterium from metagenomic library
      colon

<400> SEQUENCE: 16
```

```
Met Pro Ile Thr Ala Arg Asn Thr Leu Ala Ser Leu Leu Leu Ala Ser
 1               5                  10                  15
Ser Ala Leu Leu Leu Ser Gly Thr Ala Phe Ala Ala Asn Pro Pro Gly
             20                  25                  30
Gly Asp Pro Asp Pro Gly Cys Gln Thr Asp Cys Asn Tyr Gln Arg Gly
         35                  40                  45
Pro Asp Pro Thr Asp Ala Tyr Leu Glu Ala Ala Ser Gly Pro Tyr Thr
 50                  55                  60
Val Ser Thr Ile Arg Val Ser Ser Leu Val Pro Gly Phe Gly Gly Gly
 65                  70                  75                  80
Thr Ile His Tyr Pro Thr Asn Ala Gly Gly Gly Lys Met Ala Gly Ile
                 85                  90                  95
Val Val Ile Pro Gly Tyr Leu Ser Phe Glu Ser Ser Ile Glu Trp Trp
            100                 105                 110
Gly Pro Arg Leu Ala Ser His Gly Phe Val Val Met Thr Ile Asp Thr
            115                 120                 125
Asn Thr Ile Tyr Asp Gln Pro Ser Gln Arg Arg Asp Gln Ile Glu Ala
    130                 135                 140
Ala Leu Gln Tyr Leu Val Asn Gln Ser Asn Ser Ser Ser Pro Ile
145                 150                 155                 160
Ser Gly Met Val Asp Ser Ser Arg Leu Ala Ala Val Gly Trp Ser Met
                165                 170                 175
Gly Gly Gly Gly Thr Leu Gln Leu Ala Ala Asp Gly Gly Ile Lys Ala
                180                 185                 190
Ala Ile Ala Leu Ala Pro Trp Asn Ser Ser Ile Asn Asp Phe Asn Arg
            195                 200                 205
Ile Gln Val Pro Thr Leu Ile Phe Ala Cys Gln Leu Asp Ala Ile Ala
    210                 215                 220
Pro Val Ala Leu His Ala Ser Pro Phe Tyr Asn Arg Ile Pro Asn Thr
225                 230                 235                 240
Thr Pro Lys Ala Phe Phe Glu Met Thr Gly Gly Asp His Trp Cys Ala
                245                 250                 255
Asn Gly Gly Asn Ile Tyr Ser Ala Leu Leu Gly Lys Tyr Gly Val Ser
                260                 265                 270
Trp Met Lys Leu His Leu Asp Gln Asp Thr Arg Tyr Ala Pro Phe Leu
            275                 280                 285
Cys Gly Pro Asn His Ala Ala Gln Thr Leu Ile Ser Glu Tyr Arg Gly
            290                 295                 300
Asn Cys Pro Tyr
305

<210> SEQ ID NO 17
<211> LENGTH: 418
<212> TYPE: PRT
<213> ORGANISM: Bacillus sp. TP10A.1

<400> SEQUENCE: 17

Met Met Lys Cys Cys Arg Arg Val Ala Leu Val Leu Leu Gly Leu Trp
 1               5                  10                  15
Leu Val Phe Cys Leu Ser Val Pro Gly Gly Arg Ala Glu Ala Ala Ala
             20                  25                  30
Ser Arg Ala Asn Asp Ala Pro Ile Val Leu Leu His Gly Phe Thr Gly
             35                  40                  45
Trp Gly Arg Glu Glu Met Phe Gly Phe Lys Tyr Trp Gly Gly Val Arg
 50                  55                  60
```

Gly Asp Ile Glu Gln Leu Leu Asn Ala Gln Gly Tyr Arg Thr Tyr Thr
65                  70                  75                  80

Leu Ala Val Gly Pro Leu Ser Ser Asn Trp Asp Arg Ala Cys Glu Ala
                85                  90                  95

Tyr Ala Gln Leu Val Gly Gly Thr Val Asp Tyr Gly Ala Ala His Ala
            100                 105                 110

Ala Lys His Gly His Ala Arg Phe Gly Arg Thr Tyr Pro Gly Leu Leu
        115                 120                 125

Pro Glu Leu Lys Arg Gly Gly Arg Val His Ile Ile Ala His Ser Gln
130                 135                 140

Gly Gly Gln Thr Ala Arg Met Leu Val Ser Leu Leu Glu Asn Gly Ser
145                 150                 155                 160

Lys Glu Glu Arg Glu Tyr Ala Lys Ala His Asn Val Ser Leu Ser Pro
                165                 170                 175

Leu Phe Glu Gly Gly His Asn Phe Val Leu Ser Val Thr Thr Ile Ala
            180                 185                 190

Thr Pro His Asp Gly Thr Thr Leu Val Asn Met Val Asp Phe Thr Asp
        195                 200                 205

Arg Phe Phe Asp Leu Gln Lys Ala Val Leu Lys Ala Ala Ala Val Ala
210                 215                 220

Ser Asn Val Pro Tyr Thr Ser Gln Val Tyr Asp Phe Lys Leu Asp Gln
225                 230                 235                 240

Trp Gly Leu Arg Arg Gln Pro Gly Glu Ser Phe Asp Gln Tyr Phe Glu
                245                 250                 255

Arg Leu Lys Gln Ser Pro Val Trp Thr Ser Ala Asp Thr Ala Arg Tyr
            260                 265                 270

Asp Leu Ser Val Pro Gly Ala Glu Ala Leu Asn Gln Trp Val Gln Ala
        275                 280                 285

Ser Pro Asn Thr Tyr Tyr Leu Ser Phe Ala Thr Glu Arg Thr Tyr Arg
290                 295                 300

Gly Ala Leu Thr Gly Asn Tyr Tyr Pro Glu Leu Gly Met Asn Val Phe
305                 310                 315                 320

Ser Ala Ala Val Cys Ala Pro Phe Leu Gly Ser Tyr Arg Asn Ala Ala
                325                 330                 335

Leu Gly Ile Asp Asp Arg Trp Leu Glu Asn Asp Gly Ile Val Asn Thr
            340                 345                 350

Phe Ser Met Asn Gly Pro Lys Arg Gly Ser Thr Asp Arg Ile Val Pro
        355                 360                 365

Tyr Asp Gly Thr Leu Lys Lys Gly Val Trp Asn Asp Met Gly Thr Tyr
370                 375                 380

Asn Val Asp His Leu Glu Val Ile Gly Val Asp Pro Asn Pro Leu Phe
385                 390                 395                 400

Asp Ile His Ala Phe Tyr Leu Arg Leu Ala Glu Gln Leu Ala Ser Leu
                405                 410                 415

Arg Pro

<210> SEQ ID NO 18
<211> LENGTH: 384
<212> TYPE: PRT
<213> ORGANISM: Aneurinibacillus thermoaerophilus

<400> SEQUENCE: 18

Met Gln Lys Glu Arg Lys Asn Gln Tyr Pro Ile Val Leu Val His Gly
1               5                   10                  15

-continued

Phe Ala Gly Trp Gly Arg Asp Glu Met Leu Gly Val Lys Tyr Trp Gly
            20                  25                  30

Gly Met His Asp Ile Gln Glu Asp Leu Lys Gln Tyr Gly Tyr Glu Thr
        35                  40                  45

His Thr Ala Val Val Gly Pro Phe Ser Ser Asn Trp Asp Arg Ala Cys
 50                  55                  60

Glu Leu Tyr Ala Gln Leu Val Gly Gly Thr Val Asp Tyr Gly Ala Ala
 65                  70                  75                  80

His Ala Glu Lys Tyr Gly His Asp Arg Phe Gly Arg Thr Tyr Pro Gly
                85                  90                  95

Leu Leu Lys Asn Trp Asp Gly Glu His Lys Ile His Leu Ile Gly His
            100                 105                 110

Ser Met Gly Gly Gln Thr Val Arg Val Leu Thr Gln Leu Leu Lys Glu
        115                 120                 125

Gly Ser Gln Glu Glu Arg Glu Tyr Ala Lys Lys His Gly Val Gln Leu
130                 135                 140

Ser Pro Leu Phe Glu Gly Gly Lys Ser Trp Val His Ser Val Thr Thr
145                 150                 155                 160

Ile Ala Thr Pro Asn Asp Gly Thr Thr Leu Ala Asp Val Val Thr Gln
                165                 170                 175

Leu Ile Pro Ala Ala Gln Gln Ile Met Gly Leu Ala Ala Ala Val Ser
            180                 185                 190

Gly Asn Thr Asn Val Pro Val Tyr Asp Phe Lys Leu Asp Gln Trp Gly
        195                 200                 205

Leu Lys Arg Lys Ala Gly Glu Ser Phe Val His Tyr Ala Asp Arg Val
210                 215                 220

Trp Asn Ser Gly Ile Trp Thr Asn Thr Lys Asp Ile Ser Ala Trp Asp
225                 230                 235                 240

Leu Lys Pro Glu Gly Ala Lys Glu Leu Asn Asn Trp Val Lys Ala Gln
                245                 250                 255

Pro Asp Val Tyr Tyr Phe Ser Tyr Ser Gly Glu Ala Thr Phe Arg Ser
            260                 265                 270

Leu Ile Thr Gly His His Leu Pro Asp Leu Thr Met Asn Lys Leu Ile
        275                 280                 285

Thr Pro Phe Gly Ile Phe Leu Gly Cys Tyr Gly Ser Asp Glu Lys Trp
290                 295                 300

Trp Gln Asn Asp Gly Ile Val Asn Thr Ile Ser Met Asn Gly Pro Lys
305                 310                 315                 320

Leu Gly Ser Thr Asp Glu Ile Val Pro Tyr Asp Gly Thr Pro Lys Ile
                325                 330                 335

Gly Lys Trp Asn Asp Met Gly Ile Gln Glu Asn Trp Asp His Ala Asp
            340                 345                 350

Tyr Ile Gly Leu Ser Leu Ser Tyr Val Leu Gly Ile Glu Lys Ile Glu
        355                 360                 365

Asp Phe Tyr Arg Gly Val Ala Asp Met Leu Gly Ser Leu Ser Val Arg
370                 375                 380

<210> SEQ ID NO 19
<211> LENGTH: 417
<212> TYPE: PRT
<213> ORGANISM: Bacillus sp. Tosh

<400> SEQUENCE: 19

Met Met Lys Cys Cys Arg Val Met Phe Val Leu Leu Gly Leu Trp Leu

```
1               5                   10                  15
Val Phe Gly Leu Ser Val Pro Gly Gly Arg Ala Glu Ala Thr Ser
                20                  25                  30
Arg Ala Asn Asp Ala Pro Ile Val Leu Leu His Gly Phe Thr Gly Trp
                35              40                  45
Gly Arg Glu Glu Met Phe Gly Phe Lys Tyr Trp Gly Val Arg Gly
    50                  55                  60
Asp Ile Glu Gln Trp Leu Asn Asp Asn Gly Tyr Arg Thr Tyr Thr Leu
65                  70                  75                  80
Ala Val Gly Pro Leu Ser Ser Asn Trp Asp Arg Ala Cys Glu Ala Tyr
                85                  90                  95
Ala Gln Leu Val Gly Thr Val Asp Tyr Gly Ala Ala His Ala Ala
                100                 105                 110
Lys His Gly His Ala Arg Phe Gly Arg Thr Tyr Pro Gly Leu Leu Pro
                115                 120                 125
Glu Leu Lys Arg Gly Gly Arg Ile His Ile Ile Ala His Ser Gln Gly
        130                 135                 140
Gly Gln Thr Ala Arg Met Leu Val Ser Leu Leu Glu Asn Gly Ser Gln
145                 150                 155                 160
Glu Glu Arg Glu Tyr Ala Lys Ala His Asn Val Ser Leu Ser Pro Leu
                165                 170                 175
Phe Glu Gly Gly His His Phe Val Leu Ser Val Thr Thr Ile Ala Thr
                180                 185                 190
Pro His Asp Gly Thr Thr Leu Val Asn Met Val Asp Phe Thr Asp Arg
        195                 200                 205
Phe Phe Asp Leu Gln Lys Ala Val Leu Glu Ala Ala Val Ala Ser
210                 215                 220
Asn Ala Pro Tyr Thr Ser Glu Ile Tyr Asp Phe Lys Leu Asp Gln Trp
225                 230                 235                 240
Gly Leu Arg Arg Glu Pro Gly Glu Ser Phe Asp His Tyr Phe Glu Arg
                245                 250                 255
Leu Lys Arg Ser Pro Val Trp Thr Ser Thr Asp Thr Ala Arg Tyr Asp
            260                 265                 270
Leu Ser Val Pro Gly Ala Glu Thr Leu Asn Arg Trp Val Lys Ala Ser
        275                 280                 285
Pro Asn Thr Tyr Tyr Leu Ser Phe Ser Thr Glu Arg Thr Tyr Arg Gly
        290                 295                 300
Ala Leu Thr Gly Asn Tyr Tyr Pro Glu Leu Gly Met Asn Ala Phe Ser
305                 310                 315                 320
Ala Ile Val Cys Ala Pro Phe Leu Gly Ser Tyr Arg Asn Ala Ala Leu
                325                 330                 335
Gly Ile Asp Ser His Trp Leu Glu Asn Asp Gly Ile Val Asn Thr Ile
                340                 345                 350
Ser Met Ser Gly Pro Lys Arg Gly Ser Ser Asp Arg Ile Val Pro Tyr
                355                 360                 365
Asp Gly Ala Leu Lys Lys Gly Val Trp Asn Asp Met Gly Thr Tyr Asn
        370                 375                 380
Val Asp His Leu Glu Ile Gly Val Asp Pro Asn Pro Ser Phe Asp
385                 390                 395                 400
Ile Arg Ala Phe Tyr Leu Arg Leu Ala Glu Gln Leu Ala Ser Leu Arg
                405                 410                 415
Pro
```

<210> SEQ ID NO 20
<211> LENGTH: 416
<212> TYPE: PRT
<213> ORGANISM: Geobacillus zalihae

<400> SEQUENCE: 20

```
Met Lys Cys Cys Arg Ile Met Phe Val Leu Leu Gly Leu Trp Phe Val
1               5                   10                  15

Phe Gly Leu Ser Val Pro Gly Gly Arg Thr Glu Ala Ala Ser Leu Arg
            20                  25                  30

Ala Asn Asp Ala Pro Ile Val Leu Leu His Gly Phe Thr Gly Trp Gly
        35                  40                  45

Arg Glu Glu Met Phe Gly Phe Lys Tyr Trp Gly Gly Val Arg Gly Asp
    50                  55                  60

Ile Glu Gln Trp Leu Asn Asp Asn Gly Tyr Arg Thr Tyr Thr Leu Ala
65                  70                  75                  80

Val Gly Pro Leu Ser Ser Asn Trp Asp Arg Ala Cys Glu Ala Tyr Ala
                85                  90                  95

Gln Leu Val Gly Gly Thr Val Asp Tyr Gly Ala Ala His Ala Ala Lys
            100                 105                 110

His Gly His Ala Arg Phe Gly Arg Thr Tyr Pro Gly Leu Leu Pro Glu
        115                 120                 125

Leu Lys Arg Gly Gly Arg Ile His Ile Ile Ala His Ser Gln Gly Gly
    130                 135                 140

Gln Thr Ala Arg Met Leu Val Ser Leu Leu Glu Asn Gly Ser Gln Glu
145                 150                 155                 160

Glu Arg Glu Tyr Ala Lys Ala His Asn Val Ser Leu Ser Pro Leu Phe
                165                 170                 175

Glu Gly Gly His His Phe Val Leu Ser Val Thr Thr Ile Ala Thr Pro
            180                 185                 190

His Asp Gly Thr Thr Leu Val Asn Met Val Asp Phe Thr Asp Arg Phe
        195                 200                 205

Phe Asp Leu Gln Lys Ala Val Leu Glu Ala Ala Ala Val Ala Ser Asn
    210                 215                 220

Val Pro Tyr Thr Ser Gln Val Tyr Asp Phe Lys Leu Asp Gln Trp Gly
225                 230                 235                 240

Leu Arg Arg Gln Pro Gly Glu Ser Phe Asp His Tyr Phe Glu Arg Leu
                245                 250                 255

Lys Arg Ser Pro Val Trp Thr Ser Thr Asp Thr Ala Arg Tyr Asp Leu
            260                 265                 270

Ser Val Ser Gly Ala Glu Lys Leu Asn Gln Trp Val Gln Ala Ser Pro
        275                 280                 285

Asn Thr Tyr Tyr Leu Ser Phe Ser Thr Glu Arg Thr Tyr Arg Gly Ala
    290                 295                 300

Leu Thr Gly Asn His Tyr Pro Glu Leu Gly Met Asn Ala Phe Ser Ala
305                 310                 315                 320

Val Val Cys Ala Pro Phe Leu Gly Ser Tyr Arg Asn Pro Thr Leu Gly
                325                 330                 335

Ile Asp Asp Arg Trp Leu Glu Asn Asp Gly Ile Val Asn Thr Val Ser
            340                 345                 350

Met Asn Gly Pro Lys Arg Gly Ser Ser Asp Arg Ile Val Pro Tyr Asp
        355                 360                 365

Gly Thr Leu Lys Lys Gly Val Trp Asn Asp Met Gly Thr Tyr Asn Val
    370                 375                 380
```

```
Asp His Leu Glu Ile Ile Gly Val Asp Pro Asn Pro Ser Phe Asp Ile
385                 390                 395                 400

Arg Ala Phe Tyr Leu Arg Leu Ala Glu Gln Leu Ala Ser Leu Gln Pro
                405                 410                 415

<210> SEQ ID NO 21
<211> LENGTH: 212
<212> TYPE: PRT
<213> ORGANISM: Bacillus subtilis

<400> SEQUENCE: 21

Met Lys Phe Val Lys Arg Ile Ile Ala Leu Val Thr Ile Leu Met
1               5                   10                  15

Leu Ser Val Thr Ser Leu Phe Ala Leu Gln Pro Ser Ala Lys Ala Ala
                20                  25                  30

Glu His Asn Pro Val Val Met Val His Gly Ile Gly Gly Ala Ser Phe
                35                  40                  45

Asn Phe Ala Gly Ile Lys Ser Tyr Leu Val Ser Gln Gly Trp Ser Arg
        50                  55                  60

Asp Lys Leu Tyr Ala Val Asp Phe Trp Asp Lys Thr Gly Thr Asn Tyr
65              70                  75                  80

Asn Asn Gly Pro Val Leu Ser Arg Phe Val Gln Lys Val Leu Asp Glu
                85                  90                  95

Thr Gly Ala Lys Lys Val Asp Ile Val Ala His Ser Met Gly Gly Ala
                100                 105                 110

Asn Thr Leu Tyr Tyr Ile Lys Asn Leu Asp Gly Gly Asn Lys Val Ala
            115                 120                 125

Asn Val Val Thr Leu Gly Gly Ala Asn Arg Leu Thr Thr Gly Lys Ala
            130                 135                 140

Leu Pro Gly Thr Asp Pro Asn Gln Lys Ile Leu Tyr Thr Ser Ile Tyr
145                 150                 155                 160

Ser Ser Ala Asp Met Ile Val Met Asn Tyr Leu Ser Arg Leu Asp Gly
                165                 170                 175

Ala Arg Asn Val Gln Ile His Gly Val Gly His Ile Gly Leu Leu Tyr
                180                 185                 190

Ser Ser Gln Val Asn Ser Leu Ile Lys Glu Gly Leu Asn Gly Gly Gly
            195                 200                 205

Gln Asn Thr Asn
        210

<210> SEQ ID NO 22
<211> LENGTH: 210
<212> TYPE: PRT
<213> ORGANISM: Bacillus subtilis

<400> SEQUENCE: 22

Met Lys Lys Val Leu Met Ala Phe Ile Ile Cys Leu Ser Leu Ile Leu
1               5                   10                  15

Ser Val Leu Ala Ala Pro Pro Ser Gly Ala Lys Ala Glu Ser Val His
                20                  25                  30

Asn Pro Val Val Leu Val His Gly Ile Ser Gly Ala Ser Tyr Asn Phe
                35                  40                  45

Phe Ala Ile Lys Asn Tyr Leu Ile Ser Gln Gly Trp Gln Ser Asn Lys
        50                  55                  60

Leu Tyr Ala Ile Asp Phe Tyr Asp Lys Thr Gly Asn Asn Leu Asn Asn
65              70                  75                  80
```

```
Gly Pro Gln Leu Ala Ser Tyr Val Asp Arg Val Leu Lys Glu Thr Gly
                85                  90                  95

Ala Lys Lys Val Asp Ile Val Ala His Ser Met Gly Gly Ala Asn Thr
            100                 105                 110

Leu Tyr Tyr Ile Lys Tyr Leu Gly Gly Asn Lys Ile Gln Asn Val
        115                 120                 125

Val Thr Leu Gly Gly Ala Asn Gly Leu Val Ser Ser Thr Ala Leu Pro
130                 135                 140

Gly Thr Asp Pro Asn Gln Lys Ile Leu Tyr Thr Ser Ile Tyr Ser Leu
145                 150                 155                 160

Asn Asp Gln Ile Val Ile Asn Ser Leu Ser Arg Leu Gln Gly Ala Arg
                165                 170                 175

Asn Ile Gln Leu Tyr Gly Ile Gly His Ile Gly Leu Leu Ser Asn Ser
            180                 185                 190

Gln Val Asn Gly Tyr Ile Lys Glu Gly Leu Asn Gly Gly Gly Leu Asn
        195                 200                 205

Thr Asn
    210

<210> SEQ ID NO 23
<211> LENGTH: 418
<212> TYPE: PRT
<213> ORGANISM: Geobacillus kaustophilus

<400> SEQUENCE: 23

Met Met Lys Cys Cys Arg Arg Val Ala Leu Val Leu Leu Gly Leu Trp
1               5                   10                  15

Phe Val Phe Cys Ile Ser Val Leu Gly Gly Arg Ala Glu Ala Ala Ala
            20                  25                  30

Ser Arg Ala Asn Asp Ala Pro Ile Val Leu Leu His Gly Phe Thr Gly
        35                  40                  45

Trp Gly Arg Glu Glu Met Phe Gly Phe Lys Tyr Trp Gly Gly Val Arg
    50                  55                  60

Gly Asp Ile Glu Gln Trp Leu Asn Asp Asn Gly Tyr Arg Thr Tyr Thr
65                  70                  75                  80

Leu Ala Val Gly Pro Leu Ser Ser Asn Trp Asp Arg Ala Cys Glu Ala
                85                  90                  95

Tyr Ala Gln Leu Val Gly Gly Thr Val Asp Tyr Gly Ala Ala His Ala
            100                 105                 110

Ala Lys His Gly His Ala Arg Phe Gly Arg Thr Tyr Pro Gly Leu Leu
        115                 120                 125

Pro Glu Leu Lys Arg Gly Gly Arg Ile His Ile Ile Ala His Ser Gln
130                 135                 140

Gly Gly Gln Thr Ala Arg Met Leu Val Ser Leu Leu Glu Asn Gly Ser
145                 150                 155                 160

Gln Glu Glu Arg Glu Tyr Ala Lys Ala His Asn Val Ser Leu Ser Pro
                165                 170                 175

Leu Phe Glu Gly Gly His His Phe Val Leu Ser Val Thr Thr Ile Ala
            180                 185                 190

Thr Pro His Asp Gly Thr Thr Leu Val Asn Met Val Asp Phe Thr Asp
        195                 200                 205

Arg Phe Phe Asp Leu Gln Lys Ala Val Leu Glu Ala Ala Val Ala
210                 215                 220

Ser Asn Val Pro Tyr Thr Ser Gln Val Tyr Asp Phe Lys Leu Asp Gln
```

```
                225                 230                 235                 240
Trp Gly Leu Arg Arg Gln Pro Gly Glu Ser Phe Asp His Tyr Phe Glu
                    245                 250                 255

Arg Leu Lys Arg Ser Pro Val Trp Thr Ser Asp Thr Ala Arg Tyr
                260                 265                 270

Asp Leu Ser Val Pro Gly Ala Glu Lys Leu Asn Gln Trp Val Lys Ala
                275                 280                 285

Ser Pro Asn Thr Tyr Tyr Leu Ser Phe Ala Thr Glu Arg Thr Tyr Arg
290                 295                 300

Gly Ala Leu Thr Gly Asn Tyr Tyr Pro Glu Leu Gly Met Asn Ala Phe
305                 310                 315                 320

Ser Ala Val Val Cys Ala Pro Phe Leu Gly Ser Tyr Arg Asn Ala Thr
                    325                 330                 335

Leu Gly Ile Asp Asp Arg Trp Leu Glu Asn Asp Gly Ile Val Asn Thr
                340                 345                 350

Phe Ser Met Asn Gly Pro Lys Arg Gly Ser Thr Asp Arg Ile Val Pro
                355                 360                 365

Tyr Asp Gly Thr Ile Lys Lys Gly Val Trp Asn Tyr Met Gly Thr Tyr
370                 375                 380

Asn Val Asp His Leu Glu Val Ile Gly Val Asp Pro Asn Pro Leu Phe
385                 390                 395                 400

Asp Ile Arg Ala Phe Tyr Leu Arg Leu Ala Glu Gln Leu Ala Ser Leu
                    405                 410                 415

Gln Pro

<210> SEQ ID NO 24
<211> LENGTH: 416
<212> TYPE: PRT
<213> ORGANISM: Bacillus sp. 42

<400> SEQUENCE: 24

Met Lys Cys Cys Arg Ile Met Phe Val Leu Leu Gly Leu Trp Phe Val
1               5                   10                  15

Phe Gly Leu Ser Val Pro Gly Gly Arg Thr Glu Ala Ala Ser Leu Arg
                20                  25                  30

Ala Asn Asp Ala Pro Ile Val Leu Leu His Gly Phe Thr Gly Trp Gly
            35                  40                  45

Arg Glu Glu Met Phe Gly Phe Lys Tyr Trp Gly Gly Val Arg Gly Asp
        50                  55                  60

Ile Glu Gln Trp Leu Asn Asp Asn Gly Tyr Arg Thr Tyr Thr Leu Ala
65                  70                  75                  80

Val Gly Pro Leu Ser Ser Asn Trp Asp Arg Ala Cys Glu Ala Tyr Ala
                85                  90                  95

Gln Leu Val Gly Gly Thr Val Asp Tyr Gly Ala Ala His Ala Ala Lys
            100                 105                 110

His Gly His Ala Arg Phe Gly Arg Thr Tyr Pro Gly Leu Leu Pro Glu
        115                 120                 125

Leu Lys Arg Gly Gly Arg Ile His Ile Ile Ala His Ser Gln Gly Gly
    130                 135                 140

Gln Thr Ala Arg Met Leu Val Ser Leu Leu Glu Asn Gly Ser Gln Glu
145                 150                 155                 160

Glu Arg Glu Tyr Ala Lys Ala His Asn Val Ser Leu Ser Pro Trp Phe
                165                 170                 175

Glu Gly Gly His His Phe Val Leu Ser Val Thr Thr Ile Ala Thr Pro
```

```
              180                 185                 190
His Asp Gly Thr Thr Leu Val Asn Met Val Asp Phe Thr Asp Arg Phe
            195                 200                 205

Phe Asp Leu Gln Lys Ala Val Leu Glu Ala Ala Val Ala Ser Asn
210                 215                 220

Val Pro Tyr Thr Ser Gln Val Tyr Asp Phe Lys Leu Asp Gln Trp Gly
225                 230                 235                 240

Leu Arg Arg Gln Pro Gly Glu Ser Phe Asp His Tyr Phe Glu Arg Leu
            245                 250                 255

Lys Arg Ser Pro Val Trp Thr Ser Thr Asp Thr Ala Arg Tyr Asp Leu
            260                 265                 270

Ser Val Ser Gly Ala Glu Lys Leu Asn Gln Trp Val Gln Ala Ser Pro
            275                 280                 285

Asn Thr Tyr Tyr Leu Ser Phe Ser Thr Glu Arg Thr Tyr Arg Gly Ala
            290                 295                 300

Leu Thr Gly Asn His Tyr Pro Glu Leu Gly Met Asn Ala Phe Ser Ala
305                 310                 315                 320

Val Val Cys Ala Pro Phe Leu Gly Ser Tyr Arg Asn Pro Thr Leu Gly
            325                 330                 335

Ile Asp Asp Arg Trp Leu Glu Asn Asp Gly Ile Val Asn Thr Val Ser
            340                 345                 350

Met Asn Gly Pro Lys Arg Gly Ser Ser Asp Arg Ile Val Pro Tyr Asp
            355                 360                 365

Gly Thr Leu Lys Lys Gly Val Trp Asn Asp Met Gly Thr Tyr Asn Val
370                 375                 380

Asp His Leu Glu Ile Ile Gly Val Asp Pro Asn Pro Ser Phe Asp Ile
385                 390                 395                 400

Arg Ala Phe Tyr Leu Arg Leu Ala Glu Gln Leu Ala Ser Leu Arg Pro
            405                 410                 415

<210> SEQ ID NO 25
<211> LENGTH: 416
<212> TYPE: PRT
<213> ORGANISM: Bacillus sp. L2

<400> SEQUENCE: 25

Met Lys Cys Cys Arg Ile Met Phe Val Leu Leu Gly Leu Trp Phe Val
1               5                   10                  15

Phe Gly Leu Ser Val Pro Gly Gly Arg Thr Glu Ala Ala Ser Leu Arg
            20                  25                  30

Ala Asn Asp Ala Pro Ile Val Leu Leu His Gly Phe Thr Gly Trp Gly
            35                  40                  45

Arg Glu Glu Met Phe Gly Phe Lys Tyr Trp Gly Gly Val Arg Gly Asp
50                  55                  60

Ile Glu Gln Trp Leu Asn Asp Asn Gly Tyr Arg Thr Tyr Thr Leu Ala
65                  70                  75                  80

Val Gly Pro Leu Ser Ser Asn Trp Asp Arg Ala Cys Glu Ala Tyr Ala
            85                  90                  95

Gln Leu Val Gly Gly Thr Val Asp Tyr Gly Ala Ala His Ala Ala Lys
            100                 105                 110

His Gly His Ala Arg Phe Gly Arg Thr Tyr Pro Gly Leu Leu Pro Glu
            115                 120                 125

Leu Lys Arg Gly Gly Arg Ile His Ile Ile Ala His Ser Gln Gly Gly
            130                 135                 140
```

Gln Thr Ala Arg Met Leu Val Ser Leu Leu Glu Asn Gly Ser Gln Glu
145                 150                 155                 160

Glu Arg Glu Tyr Ala Lys Ala His Asn Val Ser Leu Ser Pro Leu Phe
                165                 170                 175

Glu Gly Gly His His Phe Val Leu Ser Val Thr Thr Ile Ala Thr Pro
            180                 185                 190

His Asp Gly Thr Thr Leu Val Asn Met Val Asp Phe Thr Asp Arg Phe
            195                 200                 205

Phe Asp Leu Gln Lys Ala Val Leu Glu Ala Ala Val Ala Ser Asn
210                 215                 220

Val Pro Tyr Thr Ser Gln Val Tyr Asp Phe Lys Leu Asp Gln Trp Gly
225                 230                 235                 240

Leu Arg Arg Gln Pro Gly Glu Ser Phe Asp His Tyr Phe Glu Arg Leu
                245                 250                 255

Lys Arg Ser Pro Val Trp Thr Ser Thr Asp Thr Ala Arg Tyr Asp Leu
                260                 265                 270

Ser Val Ser Gly Ala Glu Lys Leu Asn Gln Trp Val Gln Ala Ser Pro
            275                 280                 285

Asn Thr Tyr Tyr Leu Ser Phe Ser Thr Glu Arg Thr Tyr Arg Gly Ala
290                 295                 300

Leu Thr Gly Asn His Tyr Pro Glu Leu Gly Met Asn Ala Phe Ser Ala
305                 310                 315                 320

Val Val Cys Ala Pro Phe Leu Gly Ser Tyr Arg Asn Pro Thr Leu Gly
                325                 330                 335

Ile Asp Asp Arg Trp Leu Glu Asn Asp Gly Ile Val Asn Thr Val Ser
                340                 345                 350

Met Asn Gly Pro Lys Arg Gly Ser Ser Asp Arg Ile Val Pro Tyr Asp
            355                 360                 365

Gly Thr Leu Lys Lys Gly Val Trp Asn Asp Met Gly Thr Tyr Asn Val
            370                 375                 380

Asp His Leu Glu Ile Ile Gly Val Asp Pro Asn Pro Ser Phe Asp Ile
385                 390                 395                 400

Arg Ala Phe Tyr Leu Arg Leu Ala Glu Gln Leu Ala Ser Leu Leu Pro
                405                 410                 415

<210> SEQ ID NO 26
<211> LENGTH: 417
<212> TYPE: PRT
<213> ORGANISM: Geobacillus sp. SF1

<400> SEQUENCE: 26

Met Met Lys Gly Cys Arg Val Met Phe Val Leu Leu Gly Leu Trp Phe
1               5                   10                  15

Val Phe Gly Leu Ser Val Pro Gly Gly Arg Thr Glu Ala Ala Ser Pro
                20                  25                  30

Arg Ala Asn Asp Ala Pro Ile Val Leu Leu His Gly Phe Thr Gly Trp
            35                  40                  45

Gly Arg Glu Glu Met Leu Gly Phe Lys Tyr Trp Gly Gly Val Arg Gly
        50                  55                  60

Asp Ile Glu Gln Trp Leu Asn Asp Asn Gly Tyr Arg Thr Tyr Thr Leu
65                  70                  75                  80

Ala Val Gly Pro Leu Ser Ser Asn Trp Asp Arg Ala Cys Glu Ala Tyr
                85                  90                  95

Ala Gln Leu Val Gly Gly Thr Val Asp Tyr Gly Ala Ala His Ala Ala
                100                 105                 110

Lys His Gly His Ala Arg Phe Gly Arg Thr Tyr Pro Gly Leu Leu Pro
            115                 120                 125

Glu Leu Lys Arg Gly Gly Arg Val His Ile Ile Ala His Ser Gln Gly
130                 135                 140

Gly Gln Thr Ala Arg Met Leu Val Ser Leu Leu Glu Asn Gly Ser Gln
145                 150                 155                 160

Glu Glu Arg Glu Tyr Ala Lys Glu His Asn Val Ser Leu Ser Pro Leu
                165                 170                 175

Phe Glu Gly Gly His Arg Phe Val Leu Ser Val Thr Thr Ile Ala Thr
            180                 185                 190

Pro His Asp Gly Thr Thr Leu Val Asn Met Val Asp Phe Thr Asp Arg
        195                 200                 205

Phe Phe Asp Leu Gln Lys Ala Val Leu Glu Ala Ala Val Ala Ser
210                 215                 220

Asn Ala Pro Tyr Thr Ser Glu Ile Tyr Asp Phe Lys Leu Asp Gln Trp
225                 230                 235                 240

Gly Leu Arg Arg Glu Pro Gly Glu Ser Phe Asp His Tyr Phe Glu Arg
                245                 250                 255

Leu Lys Arg Ser Pro Val Trp Thr Ser Thr Thr Ala Arg Tyr Asp
        260                 265                 270

Leu Ser Val Ser Gly Ala Glu Lys Leu Asn Gln Trp Val Gln Ala Ser
        275                 280                 285

Pro Asn Thr Tyr Tyr Leu Ser Phe Ala Thr Glu Arg Thr Tyr Arg Gly
        290                 295                 300

Ala Leu Thr Gly Asn Tyr Tyr Pro Glu Leu Gly Met Asn Ala Phe Ser
305                 310                 315                 320

Ala Val Val Cys Ala Pro Phe Leu Gly Ser Tyr Arg Asn Pro Thr Leu
                325                 330                 335

Gly Ile Asp Asp Arg Trp Leu Glu Asn Asp Gly Ile Val Asn Thr Val
            340                 345                 350

Ser Met Asn Gly Pro Lys Arg Gly Ser Ser Asp Arg Ile Val Pro Tyr
        355                 360                 365

Asp Gly Ala Leu Lys Lys Gly Val Trp Asn Asp Met Gly Thr Tyr Asn
    370                 375                 380

Val Asp His Leu Glu Ile Ile Gly Val Asp Pro Asn Pro Ser Phe Asp
385                 390                 395                 400

Ile Arg Ala Phe Tyr Leu Arg Leu Ala Glu Gln Leu Ala Ser Leu Gln
                405                 410                 415

Pro

<210> SEQ ID NO 27
<211> LENGTH: 289
<212> TYPE: PRT
<213> ORGANISM: Streptomyces lividans

<400> SEQUENCE: 27

Met Pro Met Lys Ile Asn Arg Tyr Ala Ile Gly Ser Ala Ala Leu Ala
1               5                   10                  15

Ala Gly Leu Leu Met Ser Ser Ala Phe Ala Val Asn Pro Gly Gly
            20                  25                  30

Gly Gly Ser Gly Phe Ala Ser Leu Tyr Asn Arg Ala Glu Ser Asp Gly
        35                  40                  45

Arg Cys Ser Val Thr Arg Leu Asn Val Gly Ser Ser Thr Phe Tyr Ile
    50                  55                  60

```
Pro Arg Asp Pro Ser Asn Pro Asn Ala Arg Phe Asn Val Leu Val Trp
 65                  70                  75                  80

Gly Asn Gly Thr Gly Asn Ser Leu Thr Tyr Ala Thr Leu Leu Glu
             85                  90                  95

Ser Val Ala Ser His Cys Ile Ala Val Ala Ala Asn Thr Ala Asn
            100                 105                 110

Ser Gly Thr Gly Val Glu Met Gln Glu Ala Tyr Asn Ser Leu Arg Ser
            115                 120                 125

Arg Tyr Gly Asn Ile Leu Gly Ser Lys Val Cys Thr Ala Gly His Ser
130                 135                 140

Gln Gly Gly Gly Ser Phe Asn Ala Ala Asn Arg Ile Gly Ala Asn
145                 150                 155                 160

Cys Val Ile Pro Val Gln Pro Asp Thr Arg Phe Thr Thr Arg Ile Tyr
                165                 170                 175

Ser Pro Leu Ala Ser His Val Glu Val Ile Thr Leu Trp Gly Gln Ile
            180                 185                 190

Asp Thr Leu Ala Pro Ala Ser Gly Asn Arg Ser Asn Val Glu Arg Ala
            195                 200                 205

Ser Thr Ile Leu Thr Gln Val Glu Thr Ser Gly Glu Gly His Phe Ala
210                 215                 220

Pro Val Ser Gly Arg Gly Gly Lys Ile Gly Thr Met Phe Arg Met Ala
225                 230                 235                 240

Asn Ile Ala Gln Leu Ser Asn Asp Pro Ala Thr Ala Gln Glu Phe Arg
                245                 250                 255

Arg Ala Phe Trp Gly Pro Thr Thr Asp Tyr Thr Ala Ser Thr Ser His
            260                 265                 270

Pro Asp Ile Ser Glu Val Arg Arg Asn Ala Ala Ala Gln Ala Thr Thr
            275                 280                 285

Pro

<210> SEQ ID NO 28
<211> LENGTH: 302
<212> TYPE: PRT
<213> ORGANISM: Fervidobacterium nodosum

<400> SEQUENCE: 28

Met Tyr Tyr Asn Asn Gly Ile Pro Val Tyr Arg Thr Ile Lys Glu Ile
 1               5                  10                  15

Lys Pro Phe Phe Glu Tyr Thr Lys Val Ser Glu Val Tyr Trp Glu Arg
             20                  25                  30

Pro Val Pro Glu Ile Val Lys Ile Arg Asp Gly Glu Leu Ser Val Val
             35                  40                  45

Leu Ile His Gly Ile Asp Pro Met Glu Val Asn Gly Ser Trp Thr Leu
     50                  55                  60

Tyr Lys Glu Tyr Phe Val Asn Thr Trp Asn Ser Leu Leu Pro Lys Asn
 65                  70                  75                  80

Cys Gly Leu Tyr Ile Phe Ile Tyr Pro Thr Leu Asp Val Pro Leu Glu
             85                  90                  95

Glu Thr Ala Lys Ile Leu Val Asp Glu Ile Ile Lys Leu Asn Lys Lys
            100                 105                 110

Val Asn Ile Tyr Ala His Ser Met Gly Gly Ile Leu Leu Arg Tyr Val
            115                 120                 125

Leu Gln Asn Glu Glu Phe Arg Glu Phe Val Asn Lys Ile Ile Phe Ala
130                 135                 140
```

```
Gly Thr Pro His Leu Gly Thr Pro Leu Ala Asn Phe Val Val Leu Asp
145                 150                 155                 160

Lys Ser Val Leu Lys Phe His Pro Lys Trp Asp Ile Ile Lys Thr Val
                165                 170                 175

Ile Leu Met Ala Asn Thr Ala Trp Val Phe Ile Asp Ala Pro Asn Tyr
            180                 185                 190

Lys Tyr Leu Thr Phe Gly Phe Glu Lys Pro Glu Ile Pro Glu Asn Ile
            195                 200                 205

Asn Phe Met Asn Phe Ala Ala Lys Ile Asn Ala Asn Thr Ser Ser Ile
            210                 215                 220

Val Lys Asn Leu Ile Asn Thr Asp Phe Phe Ser Ser Ile Ala Leu Gln
225                 230                 235                 240

Ile Leu Glu Ser Thr Ile Lys Ile Ile Tyr Pro Lys Asp Ser Asp Phe
                245                 250                 255

Thr Gln Asn Asp Gly Met Val Pro Leu Phe Ser Ala Thr Tyr Tyr Gly
            260                 265                 270

Asn Glu Lys Val Phe Glu Gly Phe Asp His Ala Asp Leu Ala Ile Ser
            275                 280                 285

Glu Thr Ile Val Lys Glu Ala Ile Lys Tyr Phe Phe Gly Glu
            290                 295                 300
```

<210> SEQ ID NO 29
<211> LENGTH: 389
<212> TYPE: PRT
<213> ORGANISM: Geobacillus sp. SBS-4S

<400> SEQUENCE: 29

```
Met Ala Ala Ser Arg Ala Asn Asp Ala Pro Ile Val Leu Leu His Gly
1               5                   10                  15

Phe Thr Gly Trp Gly Arg Glu Glu Met Phe Gly Phe Lys Tyr Trp Gly
                20                  25                  30

Gly Val Arg Gly Asp Ile Glu Gln Trp Leu Asn Asp Asn Gly Tyr Arg
            35                  40                  45

Thr Tyr Thr Leu Ala Val Gly Pro Leu Ser Ser Asn Trp Asp Arg Ala
50                  55                  60

Cys Glu Ala Tyr Ala Gln Leu Val Gly Gly Thr Val Asp Tyr Gly Ala
65                  70                  75                  80

Ala His Ala Ala Lys His Gly His Ala Arg Phe Gly Arg Thr Tyr Leu
                85                  90                  95

Gly Leu Leu Pro Glu Leu Lys Arg Gly Arg Ile His Ile Ile Ala
            100                 105                 110

His Ser Gln Gly Gly Gln Thr Ala Arg Met Leu Val Ser Leu Leu Glu
            115                 120                 125

Asn Gly Ser Gln Glu Glu Arg Glu Tyr Ala Lys Ala His Asn Val Ser
            130                 135                 140

Leu Ser Pro Leu Phe Glu Gly Gly His His Phe Val Leu Ser Val Thr
145                 150                 155                 160

Thr Ile Ala Thr Pro His Asp Gly Thr Thr Leu Val Asn Met Val Asp
                165                 170                 175

Phe Thr Asp Arg Phe Phe Asp Leu Gln Lys Ala Val Leu Glu Ala Ala
            180                 185                 190

Ala Val Ala Ser Asn Val Pro Tyr Thr Ser Gln Val Tyr Asp Phe Lys
            195                 200                 205

Leu Asp Gln Trp Gly Leu Arg Arg Gln Pro Gly Glu Ser Phe Asp His
```

```
                210                 215                 220
Tyr Phe Glu Arg Leu Lys Arg Ser Pro Val Trp Thr Ser Thr Asp Thr
225                 230                 235                 240

Ala Arg Tyr Asp Leu Ser Val Ser Gly Ala Glu Lys Leu Asn Gln Trp
                245                 250                 255

Val Gln Ala Ser Pro Asn Thr Tyr Tyr Leu Ser Phe Ala Thr Glu Arg
                260                 265                 270

Thr Tyr Arg Gly Ala Leu Thr Gly Asn Tyr Tyr Pro Glu Leu Gly Met
                275                 280                 285

Asn Ala Phe Ser Ala Val Val Cys Ala Pro Phe Leu Gly Ser Tyr Arg
                290                 295                 300

Asn Pro Thr Leu Gly Ile Asp Asp Arg Trp Leu Glu Asn Asp Gly Ile
305                 310                 315                 320

Val Asn Thr Val Ser Met Asn Gly Pro Lys Arg Gly Ser Ser Asp Arg
                325                 330                 335

Ile Val Pro Tyr Asp Gly Ala Leu Lys Lys Gly Val Trp Asn Asp Met
                340                 345                 350

Gly Thr Tyr Asn Val Asp His Leu Glu Ile Ile Gly Val Asp Pro Asn
                355                 360                 365

Pro Ser Phe Asp Ile Arg Ala Phe Tyr Leu Arg Leu Ala Glu Gln Leu
    370                 375                 380

Ala Ser Leu Gln Pro
385

<210> SEQ ID NO 30
<211> LENGTH: 1024
<212> TYPE: DNA
<213> ORGANISM: Artificial Sequence
<220> FEATURE:
<223> OTHER INFORMATION: SYNTHESIZED

<400> SEQUENCE: 30
atgaaatgct gtcggattat gtttgtgttg ttaggtctgt ggttcgtgtt cggcttatct      60
gtccctggtg ggcgcactga agcggcgtcc ttacgcgcca atgatgctcc gattgtgtta     120
ctccatgggt ttaccggttg gggtcgtgag gaaatgtttg gtttcaagta ttggggcggc     180
gtgcgcggcg atatcgaaca atggctgaac gacaacggtt atcgtactta tactctggcg     240
gtcggtccgc tctctagcaa ctgggaccgg gcgtgtgaag cgtatgctca gttagtcggc     300
gggactgtcg attatggggc tgcccatgcg gctaagcacg ccatgcgcg gtttggccgc      360 acttatcccg gcctgttgcc ggaattgaaa cgtggtggcc gcatccatat catcgcccac     420
agccaagggg ggcagactgc ccgcatgtta gtctctctct tagagaacgg tagccaagaa     480
gagcgggagt acgccaaggc gcataacgtg tctttgtctc cgttgtttga aggtggtcat     540
cattttgtgt tgagtgtgac taccatcgcc actcctcatg acgggactac tttagtcaac     600
atggttgatt tcaccgatcg ctttttttgac ttgcaaaaag cggtgttgga agcggcggct     660
gtcgccagca acgtgccgta cactagtcaa gtatacgatt ttaagctcga ccaatggggt     720
ctgcgccgcc agccgggtga atctttcgac cattattttg aacggctcaa gcgctcccct     780
gtttggactt ccactgatac cgcccgctac gattatccg tttccggtgc tgagaagttg      840
aatcaatggg tgcaagctag cccgaatact tattatttga gtttctctac tgaacggact     900
tatcgcggtg cgctcactgg caaccattat cccgaactcg gtatgaatgc tttcagcgcg     960
gtcgtatgcg ctccgttttct cggttcttac cgcaatccga ctctcggcat tgacgaccgt    1020
``` tggt                                                               1024

<210> SEQ ID NO 31
<211> LENGTH: 876
<212> TYPE: DNA
<213> ORGANISM: Artificial Sequence
<220> FEATURE:
<223> OTHER INFORMATION: SYNTHESIZED

<400> SEQUENCE: 31
atgcgtagct ccttagtgct gttcttcctc tctgcttgga ctgccttggc tcggcctgtt    60
cgtcgtgctg ttcctcaaga tctgctcgac cagtttgaac tcttttctca atattctgct   120
gccgcttact gtgctgctaa caatcatgct cctgtgggct ctgacgtaac ttgctctgag   180
aatgtctgcc ctgaggtaga tgctgctgac gctacttttc tctattcttt tgaagattct   240
ggtttaggcg atgttaccgg cttactcgct ctcgacaaca ctaataaact gatcgtcctc   300
tctttccgcg gctctcgttc tgtagagaac tggatcgcta acctcgccgc cgacctgact   360
gaaatttctg acatctgctc cggctgcgag gggcatgtcg gcttcgttac ttcttggcgt   420
tctgtagccg acactattcg tgagcaggtg cagaatgccg tgaacgagca tcccgattac   480
cgcgtggtct ttaccggtca tagcttgggt ggcgctctgg ctactattgc cgctgctgct   540
ctgcgtggta atggttacaa tatcgacgtg ttctcttatg gcgctccccg cgtcggtaac   600
cgtgcttttg ctgaattcct gaccgctcag actggcggca ccctgtatcg catcacccat   660
accaatgata tcgtccctcg tctccctcct cgtgactggg gttacagcca ctctagccct   720
gagtactggg tcacttctgg taacgacgtc cctgtgaccg ctaacgacat caccgtcgtg   780
gagggcatcg attccaccga cgggaacaac caggggaata tccctgacat cccttctcat   840
ttatggtatt tcggtcccat ttctgagtgt gattaa                             876

<210> SEQ ID NO 32
<211> LENGTH: 870
<212> TYPE: DNA
<213> ORGANISM: Artificial Sequence
<220> FEATURE:
<223> OTHER INFORMATION: SYNTHESIZED

<400> SEQUENCE: 32
atgcccatga aaattaatcg ttacgctatt ggttctgccg ccttagctgc cggtttatta    60
atgtcctctg ccgctttcgc cgttaatcct ggtggtggtg gttctggttt cgcctcctta   120
tacaaccgtg ccgaatctga cggtcgttgc tctgttaccc gttaaacgt gggttcttct    180 accttctaca tccctcgtga cccctctaac cccaacgccc gtttcaacgt gttagtgtgg   240
ggtaatggta ccggtggtaa ctccttaacc tatgctactt tattagaatc tgttgccagt   300
cactgcatcg ctgtagccgc tgccaacacc gccaactccg gtaccggtgt ggaaatgcag   360
gaagcttaca actctttacg ttcccgttat ggtaacatct taggttccaa agtgtgcact   420
gccggtcact ctcagggtgg tggtggttcc ttcaacgccc caaccgtat cggtgccaac    480 tgcgtgatcc ctgtgcagcc tgatacccgt ttccaccactc ggatctactc tcctttagct   540
tctcatgtgg aagtgatcac cttatggggt cagatcgaca ctttagctcc cgcctctggt   600
aaccgttcta acgttgaacg ggcctctacc atcttaaccc aggttgaaac ttccggtgaa   660
ggtcactttg ccctgtgtc tggtcgtggt ggtaaaatcg gtactatgtt ccgtatggcc    720
aacatcgccc agttatctaa cgatcctgcc actgcccagg aattccgtcg ggctttctgg   780
ggtcctacca ctgattacac cgcctccact tctcatcccg atatctctga agtgcgtcgt   840

| | |
|---|---|
| aacgccgccg cccaggctac cacccttaa | 870 |

<210> SEQ ID NO 33
<211> LENGTH: 912
<212> TYPE: DNA
<213> ORGANISM: Artificial Sequence
<220> FEATURE:
<223> OTHER INFORMATION: SYNTHESIZED

<400> SEQUENCE: 33

| | |
|---|---|
| atggtgtact acaacaacgg catccccgtg taccggacca tcaaagaaat caaacccttc | 60 |
| tttgaataca ccaaagtctc ggaagtgtac tgggaacggc ccgtgcccga aatcgtgaaa | 120 |
| atccgggatg gcgaactgtc agtggtgctc attcacggca ttgaccccat ggaagtgaac | 180 |
| ggtagttgga ccctgtacaa agaatacttt gtgaatacct ggaatagtct gctgcccaaa | 240 |
| aattgtggtc tgtacatctt tatctacccc accctggatg tgcccctgga gaaaccgcc | 300 |
| aaaattctgg tcgatgaaat catcaaactg aataaaaaag tgaatatcta cgcccacagt | 360 |
| atgggtggca ttctgctgcg gtacgtgctg caaaatgaag aatttcggga atttgtgaac | 420 |
| aaaatcatct cgccggcac ccccaccctg ggcaccccgc tggccaattt tgtggtgctg | 480 |
| gacaagagcg tgctgaagtt tcaccccaaa tgggacatca tcaagaccgt gattctgatg | 540 |
| gccaataccg cgtgggtgtt tattgatgcg cccaattaca atacctgac ctttggcttt | 600 |
| gaaaaacccg aaattcccga aatatcaat tttatgaatt ttgccgccaa aatcaacgcc | 660 |
| aacaccagta gcatcgtgaa aaatctgatc aataccgatt tttttcatc tattgcgctg | 720 |
| caaattctcg aaagtaccat caagatcatt taccccaaag attccgattt tacccaaaat | 780 |
| gatgggatgg tgcccctgtt cagcgcgacc tactacggta tgaaaaggt gtttgaaggc | 840 |
| tttgaccacg ccgacctggc cattagcgag accattgtga aggaagcgat caaatacttt | 900 |
| tttggcgaat aa | 912 |

<210> SEQ ID NO 34
<211> LENGTH: 1024
<212> TYPE: DNA
<213> ORGANISM: Artificial Sequence
<220> FEATURE:
<223> OTHER INFORMATION: SYNTHESIZED

<400> SEQUENCE: 34

| | |
|---|---|
| atgatgaaag ctgccgggt gatggttgtg ttgctcggtt tatgctttgt gttcggctta | 60 |
| tcggtcccgg gtgggcggac tgaagcggct tccttacgcg ccaatgatgc gccgattgtg | 120 |
| ttactccatg ggtttaccgg ttggggtcgt gaggaaatgt ttggtttcaa gtattggggc | 180 |
| ggcgtgcgcg gcgatatcga acaatggctg aacgacaacg ttatcgtac ttatactctg | 240 |
| gcggtcggtc cgctctcgag caactgggac cgggcgtgtg aagcgtatgc tcagttagtc | 300 |
| ggcgggactg tcgattatgg ggctgcccat gcggctaagc acggccatgc gcggtttggc | 360 |
| cgcacttatc ccggcctgtt gccggaattg aaacgtggtg gccgcatcca tatcatcgcc | 420 |
| cacagccaag gggggcagac tgcccgcatg ttagtctcgc tcttagagaa cggtagccaa | 480 |
| gaagagcggg agtacgccaa ggcgcacaac gtgtcgttgt caccgttgtt tgaaggtggt | 540 |
| catcattttg tgttgagtgt gactaccatc gccactcctc atgacgggac tactttagtc | 600 |
| aacatggttg atttcaccga tcgcttttt gacttgcaaa aagcggtgtt ggaagcggcg | 660 |
| gctgtcgcca gcaacgtgcc gtacactagt caagtatacg attttaagct cgaccaatgg | 720 |

```
ggtctgcgcc gtcagccggg cgaatcgttc gaccattatt ttgaacggct caagcgctcc    780
cctgtctgga cttcgaccga taccgcccgc tacgatttat ccgtttccgg tgctgagaag    840
ttgaatcaat gggtgcaagc tagcccgaat acttattatt tgagtttctc tactgaacgg    900
acttatcgcg gtgcgctcac tggcaaccat tatcccgaac tcggtatgaa cgctttcagc    960
gcggtcgtat gcgctccgtt tctcggttcg taccgcaatc cgactttagg cattgacagt   1020
catt                                                                1024
```

<210> SEQ ID NO 35
<211> LENGTH: 639
<212> TYPE: DNA
<213> ORGANISM: Artificial Sequence
<220> FEATURE:
<223> OTHER INFORMATION: SYNTHESIZED

<400> SEQUENCE: 35

```
atgaaatttg taaaacggcg gatcattgcc ctggtaacca ttttgatgct gtctgttacc     60
tcgctgtttg cgttgcagcc gtcagccaaa ccgctgaac acaatcccgt cgttatggtt    120
cacggtattg cgggggcctc attcaattt gcgggcatta agagctatct cgtatctcag    180
ggctggtcgc gggacaagct gtatgccgtt gattttgg acaagaccgg caccaattat    240
aacaatggcc cggtattatc acggtttgtg caaaaggttt tagatgaaac cggtgcgaaa    300
aaagtggata ttgtcgctca cagcatgggg ggcgcgaaca ccctgtacta catcaaaaat    360
ctggacggcg gcaataaagt tgccaacgtc gtgaccctgg gcggcgcgaa ccgtttgacc    420
accggcaagg cgctgccggg caccgatccc aatcaaaaga ttttatacac ctccatttac    480
agcagtgccg atatgattgt catgaattac ttatcacggt tagatggtgc tcggaacgtt    540
caaatccatg gcgttggcca catcggcctg ctgtacagca gccaagtcaa cagcctgatt    600
aaagaagggc tgaacggcgg gggccagaat accaattaa                           639
```

<210> SEQ ID NO 36
<211> LENGTH: 1024
<212> TYPE: DNA
<213> ORGANISM: Artificial Sequence
<220> FEATURE:
<223> OTHER INFORMATION: SYNTHESIZED

<400> SEQUENCE: 36

```
atggtttcca aaagcttttt tttggctgct gcggtaaacg tggttggcgt tttggctcaa     60
gctcctaccg ctgttctcaa tgataacgaa gtcattactg gtgtgctgga gggtcaagtt    120
gatactttca aaggcatccc ctttgctgac ccgcccgttg ctgacttgcg gtttaagcat    180
cctcaaagtt ttactggctc ttaccagggt ctgcaagcca aggattttag ctccgcttgt    240
atgcaaattg atccctacaa ctctctgacc attctggaca atgttctgaa cttgggcaaa    300
attattcctg aagacttccg gggccccatt tatgacatgg ccaagggtac cgtgtcaatg    360
agtgaggatt gtctgtacct gaacgttttc cgtcccgctg gtaccaagcc tagtgataag    420
ttacctgtta tggtttggat ttatggtggt gctttcatct atggttcttc tgctgcttac    480
cctggtaacg gctacgttaa ggaaagtgtc aaaatgggcc agcccgttgt gtttgtttct    540
attaactacc gtactggtcc ctttggctt tgggtggtg atggcattac tgctgaaggc    600
aataccaact ctggttttgca cgaccagcgt aagggtctgg agtgggttag cgacaatatt    660
gccaactttg gtggtgaccc tgataaggtt atgatctttg gtgagtctgc tggcgccatg    720
agtgttggtc atcagctgat tgcttatggt ggtgacaaca cttacaatgg caagcccctg    780
```

| | |
|---|---|
| ttccattctg ctattctgca gtctggcggt cctctccctt actatgactc tacctccgtt | 840 |
| ggtcccgaaa aggcttacaa ccggtttgct gaatatgctg gctgtgatac tactgctagt | 900 |
| gacgttgaca ttttgcaatg tctccgcagc aaatctagcc aagttttgca cgatgcccaa | 960 |
| aactcgtatg acttaaagga cctgtttggc ctcctcccg aatttctggg ctttggtccc | 1020 |
| cggc | 1024 |

<210> SEQ ID NO 37
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 37

| | |
|---|---|
| caagctgttg acaattaatc atccggctcg tataatgtgt ggaaga | 46 |

<210> SEQ ID NO 38
<211> LENGTH: 964
<212> TYPE: DNA
<213> ORGANISM: Artificial Sequence
<220> FEATURE:
<223> OTHER INFORMATION: SYNTHESIZED

<400> SEQUENCE: 38

| | |
|---|---|
| ctctagctag agtcgacctg caggggggggg ggggaaagcc acgttgtgtc tcaaaatctc | 60 |
| tgatgttaca ttgcacaaga taaaatata tcatcatgaa caataaaact gtctgcttac | 120 |
| ataaacagta atacaagggg tgttatgagc catattcaac gggaaacgtc ttgctcgagg | 180 |
| ccgcgattaa attccaacat ggatgctgat ttatatgggt ataaatgggc tcgcgataat | 240 |
| gtcgggcaat caggtgcgac aatctatcga ttgtatggga agcccgatgc gccagagttg | 300 |
| tttctgaaac atggcaaagg tagcgttgcc aatgatgtta cagatgagat ggtcagacta | 360 |
| aactggctga cggaatttat gcctcttccg accatcaagc attttatccg tactcctgat | 420 |
| gatgcatggt tactcaccac tgcgatcccc gggaaaacag cattccaggt attagaagaa | 480 |
| tatcctgatt caggtgaaaa tattgttgat gcgctggcag tgttcctgcg ccggttgcat | 540 |
| tcgattcctg tttgtaattg tccttttaac agcgatcgcg tatttcgtct cgctcaggcg | 600 |
| caatcacgaa tgaataacgg tttggttgat gcgagtgatt ttgatgacga gcgtaatggc | 660 |
| tggcctgttg aacaagtctg gaaagaaatg cataagcttt tgccattctc accggattca | 720 |
| gtcgtcactc atggtgattt ctcacttgat aaccttattt ttgacgaggg gaaattaata | 780 |
| ggttgtattg atgttggacg agtcggaatc gcagaccgat accaggatct tgccatccta | 840 |
| tggaactgcc tcggtgagtt ttctccttca ttacagaaac ggcttttca aaaatatggt | 900 |
| attgataatc ctgatatgaa taaattgcag tttcatttga tgctcgatga gttttctaa | 960 |
| tcag | 964 |

<210> SEQ ID NO 39
<211> LENGTH: 852
<212> TYPE: DNA
<213> ORGANISM: Artificial Sequence
<220> FEATURE:
<223> OTHER INFORMATION: SYNTHESIZED

<400> SEQUENCE: 39

| | |
|---|---|
| tctggttcca gagcctgatt ccctcataat caagggttca ttgactagtc tttccaaaga | 60 |

```
aattttctttt tccttgacta atgggtgctg gcgagacgca attaccacga ggggattttc      120
taaaaagtgg cggatattaa tatcaagatt tgagggcggt ttacccaaaa agtataaatc      180
gtctaaatta ttcgccaaac gctccaaaat ttgttgacga ttgccaattt gtagagagat      240
ggaaatgcct ggatattgtt gacgaaattc ccccaaaagt cgtggcacaa atatttgcc       300 tgtggtaata gttgctaggc gcaggttacc tttttttaag ccctggaggt cagcaatcac      360
ttcctgcaat tgatccaggc aagaggtaat gttttttgcta gcgtctaaaa ccgcttgtcc    420
tgcttcggtt aaatagattt ttcggccaat ttgttcataa agcggcaccc cgatcgcctt     480
ggtgagttgc ttcatctgct gggaaaccgt gggctgggtc agaaacaatt cctccgccgc    540
cttggtgaaa ctccccgtcc tggcgatcgc cgcaaaaacc tcaaattggt ggagggtggc    600
attttccata gtggattaat tttatagact acttctataa attacataaa aaattggata     660
tttatctatt tttagctttc cttaataatc agatcattca agtcccttg gattagtcat      720 tgtcctcggg caggcagttt aaagcgtccc ctggtttacc tagcctagga gccccagtgc    780
tcttccgtaa accggggata tccatggcgc ttatttaatt tttctgtctg cctttttca      840 tagaaaaaat ca                                                          852

<210> SEQ ID NO 40
<211> LENGTH: 843
<212> TYPE: DNA
<213> ORGANISM: Artificial Sequence
<220> FEATURE:
<223> OTHER INFORMATION: SYNTHESIZED

<400> SEQUENCE: 40
atcaaagtta tgggttcatt caatcgacgt aaattttgc tcacctccgc cgccactgcc       60 acagggctt tatttctgaa gggttgtgcc ggcaatcccc ccgatcccaa cgccgccagc     120
accggtacta acccttctcc ccaagcggcc ggggatatta gcccagaaat gatgcccgaa    180
accgccaata tcaaactagg ctacattccc attgtggaag ctgccccatt gatcattgct    240
caagaaaaag gtttctttgc caaatatggc atgaccggtg tggaagtctc caaacaagcc    300
aactgggcct ccgctagaga taacgtcacc attggttccc agggaggcgg catcgatggc    360
ggccaatggc aaatgcccat gcctcacctg attacgaag ggatcattac caatggcaac     420
aaggtgccca tgtatgtatt ggcccaattg attacccagg gaaatggtat tgccgtagca    480
ccaatgcatg aaggcaaagg ggtaaacctg gatatcacca agcggcgga ctatatcaag      540 ggctttaaca aaaccaatgg ccgcaaattt aaggcagccc acaccttccc taacgttaac    600
caagattttt ggattcgtta ctggtttgcg gccggaggcg ttgatcctga caccgatatt    660
gacctactgg ctgtgcctcc cgctgaaaca gtccagggca tgcgcaacgg taccatggat    720
gcttttagca ctggagatcc ttggccctat cgcatcgtga cagaaaacat tggctacatg    780
gccggtttaa ctgcccaaat ttggccctat caccggaag agtacctcgc cattcgagcg     840
gat                                                                    843

<210> SEQ ID NO 41
<211> LENGTH: 34
<212> TYPE: DNA
<213> ORGANISM: Artificial Sequence
<220> FEATURE:
<223> OTHER INFORMATION: SYNTHESIZED

<400> SEQUENCE: 41
tctggttcca gagcctgatt ccctcataat caag                                   34
```

```
<210> SEQ ID NO 42
<211> LENGTH: 26
<212> TYPE: DNA
<213> ORGANISM: Artificial Sequence
<220> FEATURE:
<223> OTHER INFORMATION: SYNTHESIZED

<400> SEQUENCE: 42
atccgctcga atggcgaggt actctt                                    26

<210> SEQ ID NO 43
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 43
gccttttttc atagaaaaaa tcaagctgtt gacaattaat catccg              46

<210> SEQ ID NO 44
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 44
cggatgatta attgtcaaca gcttgatttt ttctatgaaa aaaggc              46

<210> SEQ ID NO 45
<211> LENGTH: 44
<212> TYPE: DNA
<213> ORGANISM: Artificial Sequence
<220> FEATURE:
<223> OTHER INFORMATION: SYNTHESIZED

<400> SEQUENCE: 45
aagtcgacaa gcatgcaaag ctctctagct agagtcgacc tgca                44

<210> SEQ ID NO 46
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 46
ttgaatgaac ccataacttt gatctgatta gaaaaactca tcgagc              46

<210> SEQ ID NO 47
<211> LENGTH: 47
<212> TYPE: DNA
<213> ORGANISM: Artificial Sequence
<220> FEATURE:
<223> OTHER INFORMATION: SYNTHESIZED

<400> SEQUENCE: 47
tccggctcgt ataatgtgtg gaactttaag aaggagatat acatatg             47

<210> SEQ ID NO 48
<211> LENGTH: 47
<212> TYPE: DNA
<213> ORGANISM: Artificial Sequence
<220> FEATURE:
```

<223> OTHER INFORMATION: SYNTHESIZED

<400> SEQUENCE: 48
catatgtata tctccttctt aaagttccac acattatacg agccgga                47

<210> SEQ ID NO 49
<211> LENGTH: 45
<212> TYPE: DNA
<213> ORGANISM: Artificial Sequence
<220> FEATURE:
<223> OTHER INFORMATION: SYNTHESIZED

<400> SEQUENCE: 49
taatctcgag caccaccacc accctctagc tagagtcgac ctgca                  45

<210> SEQ ID NO 50
<211> LENGTH: 45
<212> TYPE: DNA
<213> ORGANISM: Artificial Sequence
<220> FEATURE:
<223> OTHER INFORMATION: SYNTHESIZED

<400> SEQUENCE: 50
tgcaggtcga ctctagctag agggtggtgg tggtgctcga gatta                  45

<210> SEQ ID NO 51
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 51
gctcgatgag ttttctaat cagatcaaag ttatgggttc attcaa                  46

<210> SEQ ID NO 52
<211> LENGTH: 46
<212> TYPE: DNA
<213> ORGANISM: Artificial Sequence
<220> FEATURE:
<223> OTHER INFORMATION: SYNTHESIZED

<400> SEQUENCE: 52
ttgaatgaac ccataacttt gatctgatta gaaaaactca tcgagc                 46

<210> SEQ ID NO 53
<211> LENGTH: 34
<212> TYPE: DNA
<213> ORGANISM: Artificial Sequence
<220> FEATURE:
<223> OTHER INFORMATION: SYNTEHSIZED

<400> SEQUENCE: 53
atgcggccgc atgcgtagct ccttagtgct gttc                              34

<210> SEQ ID NO 54
<211> LENGTH: 33
<212> TYPE: DNA
<213> ORGANISM: Artificial Sequence
<220> FEATURE:
<223> OTHER INFORMATION: SYNTHESIZED

<400> SEQUENCE: 54
ctggatcctt aatcacactc agaaatggga ccg                               33

```
<210> SEQ ID NO 55
<211> LENGTH: 36
<212> TYPE: DNA
<213> ORGANISM: Artificial Sequence
<220> FEATURE:
<223> OTHER INFORMATION: SYNTHESIZED

<400> SEQUENCE: 55
atgcggccgc atgcccatga aaattaatcg ttacgc                          36

<210> SEQ ID NO 56
<211> LENGTH: 32
<212> TYPE: DNA
<213> ORGANISM: Artificial Sequence
<220> FEATURE:
<223> OTHER INFORMATION: SYNTHESIZED

<400> SEQUENCE: 56
ctggatcctt aagggtggt agcctgggcg gc                               32

<210> SEQ ID NO 57
<211> LENGTH: 37
<212> TYPE: DNA
<213> ORGANISM: Artificial Sequence
<220> FEATURE:
<223> OTHER INFORMATION: SYNTHESIZED

<400> SEQUENCE: 57
atgcggccgc atgaaatgct gtcggattat gtttgtg                         37

<210> SEQ ID NO 58
<211> LENGTH: 30
<212> TYPE: DNA
<213> ORGANISM: Artificial Sequence
<220> FEATURE:
<223> OTHER INFORMATION: SYNTHESIZED

<400> SEQUENCE: 58
ctggatcctt aaggctgcaa gctcgccaac                                 30
```

PHOTOSYNTHETIC MICROORGANISMS EXPRESSING THERMOSTABLE LIPASE

CROSS REFERENCE TO RELATED APPLICATIONS

This application claims priority to U.S. Provisional Application Ser. No. 61/648,920, filed May 18, 2012, which is hereby incorporated by reference.

GOVERNMENTAL RIGHTS

This invention was made with government support under DE-AR0000011 awarded by the Department of Energy. The government has certain rights in the invention.

FIELD OF THE INVENTION

The invention encompasses a recombinant photosynthetic microorganism engineered to inducibly release the contents of the microorganism.

BACKGROUND OF THE INVENTION

Cheap renewable energy is a major goal of many countries and hardly needs a justification. Not only does renewable energy provide energy independence and security but can often provide carbon neutral or better clean energy. But not all forms of renewable energy are equal. Currently wind, solar, hydro and geothermal power are excellent supplements to the power grid, but cannot be efficiently converted into liquid biofuels needed for our cars, ships and planes. There will be a high demand for biodiesel and other liquid biofuels into the foreseeable future.

Liquid biofuels can be roughly classified by the source (feedstock) and production methods. First generation biofuels like ethanol from corn are now established industries, but the trend is to move away from using food crops as the primary feedstock for energy production. Second generation biofuels like cellulosic ethanol use biomass as the primary feedstock. The biomass is obtained from the "waste" left over after food crops have been processed, or from other energy crops like switchgrass, Miscanthus, and "energycane". While eliminating the ethical dilemma of tapping into the world's food supply for fuel, cellulosic ethanol is still neither the most efficient way to produce biofuels nor a viable replacement for the majority of the nations fuel needs. Recycling biomass waste into fuel is a great idea, but growing energy crops just to harvest and digest them back into biofuel is not the most efficient use of energy, water, or arable land.

Third generation biofuels have typically been defined as fuels from photosynthetic organisms. The organisms are grown, harvested, and then the fuel precursors are extracted from the biomass. Photosynthetic microbes such as algae and cyanobacteria are the most efficient organisms for solar energy conversion, typically yielding lipids in the range of about 20-30% of dry weight. While photosynthetic microorganisms will theoretically out produce any plant based biofuel systems, costs associated with extraction continue to be a barrier to making these biofuels competitive with fossil fuels.

Hence, there is a need in the art for a microbe capable of producing biofuels or biofuel precursors while decreasing processing and extraction costs.

SUMMARY OF THE INVENTION

One aspect of the present invention encompasses a photosynthetic microorganism, wherein the microorganism comprises a nucleic acid cassette comprising an inducible promoter operably-linked to a nucleic acid encoding a thermostable lipase capable of hydrolyzing the lipid membranes of the microorganism.

Another aspect of the present invention encompasses a method for releasing the cell contents from a photosynthetic microorganism. The method comprises (a) introducing into the photosynthetic microorganism a nucleic acid cassette comprising an inducible promoter operably-linked to a nucleic acid encoding a thermostable lipase capable of hydrolyzing the lipid membranes of the microorganism; (b) culturing the photosynthetic microorganism; (c) inducing the promoter to express the thermostable lipase; (d) incubating the photosynthetic microorganisms at a temperature capable of activating the thermostable lipase, whereupon the thermostable lipase hydrolyzes the lipid membrane of the photosynthetic microorganism, releasing the intracellular contents from the photosynthetic microorganism.

Other aspects and iterations are described in more detail below.

REFERENCE TO COLOR FIGURES

The application file contains at least one photograph executed in color. Copies of this patent application publication with color photographs will be provided by the Office upon request and payment of the necessary fee.

DETAILED DESCRIPTION OF THE INVENTION

Figure 1:
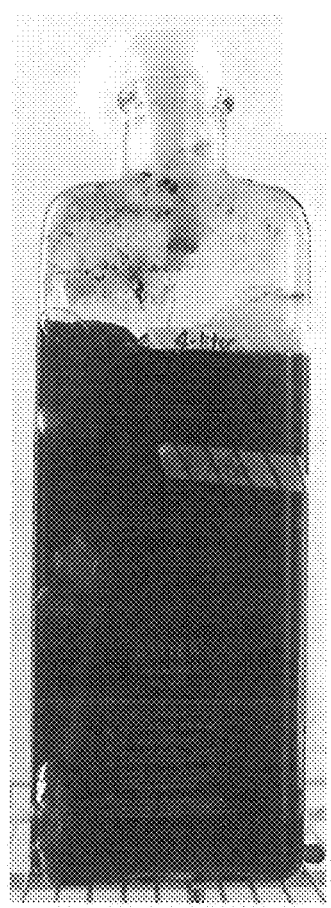
FIG. 1 depicts images during continuous semi-batch production experiment with thermorecovery. (A) The 4-liter semi-batch continuously growing SD338 culture. (B) $CO_2$ limitation pretreatment in a separation funnel. (C) Centrifuge-concentrated biomass: left, a concentrated biomass after pretreatment; middle, a concentrated biomass had been kept at 46° C. for one day; right, a concentrated biomass had been kept at 46° C. for two days.
Figure 1:
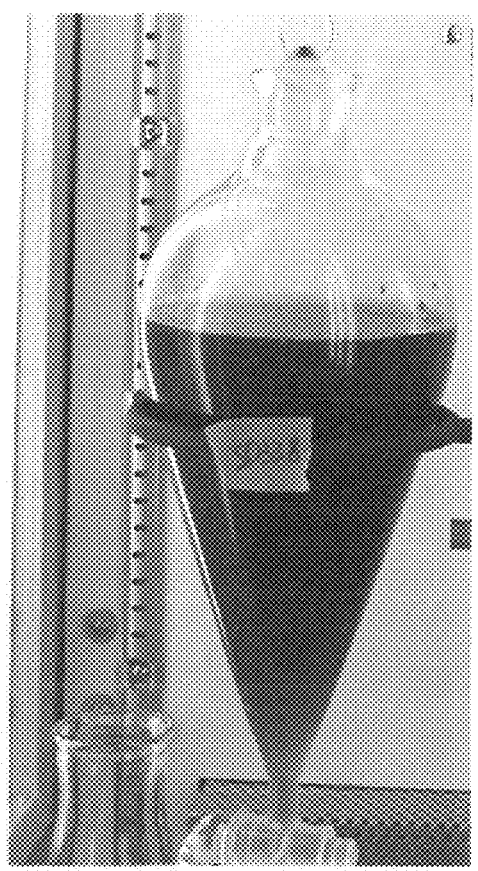
Figure 1:
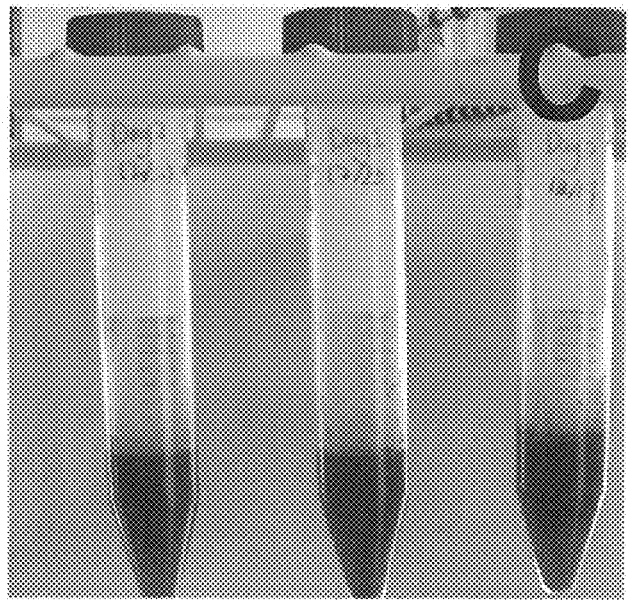

The present invention encompasses a recombinant photosynthetic microorganism engineered to inducibly release the contents of the microorganism. In particular, the present invention provides a recombinant photosynthetic microorganism capable of producing biofuels and biofuel precursors while decreasing processing and extraction costs. The photosynthetic microorganism of the invention may decrease costs by providing an efficient mechanism for the lysis of the photosynthetic microorganism, which saves time and utilizes less solvent than other extraction methods.

I. Recombinant Photosynthetic Microorganism

One aspect of the present invention provides a recombinant photosynthetic microorganism, wherein the microorganism comprises a nucleic acid cassette comprising an inducible promoter operably-linked to a nucleic acid encoding a thermostable lipase capable of hydrolyzing the lipid membranes of the microorganism to facilitate extraction and processing of cell contents, including biofuels, from the microorganism. The photosynthetic microorganism, biofuel and biofuel precursor production, and the nucleic acid cassette are discussed in more detail below.

(a) Photosynthetic Microorganism

The term "photosynthetic microorganism" as used herein, refers to any prokaryotic unicellular cyanobacterium or eukaryotic unicellular or multicellular alga. In some embodiments, the photosynthetic microorganism of the invention may be a eukaryotic alga. Non-limiting examples of an alga that may be used for the invention may include an alga belonging to the groups archaeplastida such as rhodophyta (Red algae), chlorophyta (Green algae), or glaucophyta; rhizaria or excavata such as chlorarachniophytes and euglenids; heterokonts such as bacillariophyceae (Diatoms), axodine, bolidomonas, eustigmatophyceae, phaeophyceae (Brown algae), chrysophyceae (Golden algae), raphidophyceae, synurophyceae and xanthophyceae (Yellow-green algae); cryptophyta; dinoflagellates; and haptophyta.

In preferred embodiments, a photosynthetic microorganism of the invention may be a cyanobacterium. Non limiting examples of cyanobacteria suitable for the invention include cyanobacteria belonging to the order Chroococcales, cyanobacteria belonging to the order Nostocales, and cyanobacteria belonging to the order Stigonematales. In some embodiments, the cyanobacterium belongs to the order Nos-tocales. In other embodiments, the cyanobacterium belongs to the order Stigonematales. In yet other embodiments, the cyanobacterium belongs to the order Chroococcales. In a preferred embodiment, the bacterium is derived from the genus *Synechocystis*. For instance, a bacterium of the invention may be derived from *Synechocystis* PCC sp. 6803 having ATCC #27184.

(b) Thermostable Lipase

The recombinant photosynthetic microorganism of the invention comprises a nucleic acid cassette comprising an inducible promoter operably-linked to a nucleic acid encoding a thermostable lipase able to hydrolyze acylglycerols. Such an enzme may degrade membrane lipids into free fatty acids, increasing the amount of free fatty acids harvestable from a photosynthetic microorganism, and making the harvest less labor intensive. In one embodiment, the lipase may be a lipolytic enzyme that hydrolyzes diacylglycerols, including MGDG (monogalactosyl diacylglycerol), DGDG (digalactosyl diacylglycerol), PG (phosphatidylglycerol), and SQDG (sulfoquinovosyl diacylglycerol). In another embodiment, the lipase may be a lipase that hydrolyzes triacylglycerols. In yet another embodiment, the lipase may be a lipolytic enzyme that hydrolyzes monoacylglycerols. In still yet another embodiment, the lipase may be a lipolytic enzyme from a bacterium, e.g., *Staphylococcus hyicus*. In a further embodiment, the lipase may be a lipolytic enzyme from a fungus, e.g., *Fusarium oxysporum*. In one embodiment, the lipase may be a lipolytic enzyme from an animal, e.g., guinea pig.

In preferred embodiments, the lipase is thermostable. Thermostable lipase activity increases with temperature, reaches a maximum at the optimal temperature, and then drops above the optimal temperature due to protein denaturation. The term "thermostable lipase" as used herein, refers to any lipase enzyme characterized by an optimal temperature higher than the ambient temperature at which the photosynthetic microorganism grows. As used herein, "optimal temperature" refers to the temperature at which the enzyme has the greatest activity. Accordingly, the thermostable lipase may be expressed in the photosynthetic microorganism at a temperature conducive for growth of the microorganism. Because the growth temperature of the photosynthetic microorganism is lower than the optimal temperature of the thermostable lipase, the thermostable lipase protein is expressed, but lipase activity is reduced or not optimal. At harvest, the activity of the thermostable lipase may be activated by shifting the culture of photosynthetic microorganisms to a higher temperature close to the optimal temeperature of the thermostable lipase, resulting in lysis of the photosynthetic microorganism.

When the photosynthetic microorganism is a cyanobacterium, the thermostable lipase of the invention may be a thermostable lipase with an optimal temperature higher than 27° C., the ambient temperature at which the microorganism grows. Those skilled in the art recognize that the optimal temperature of a lipase may be experimentally determined. In some embodiments, the thermostable lipase of the invention may be a thermostable lipase with an optimal temperature of about 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91 92, 93, 94, 94, 96° C. or more. In other embodiments, the thermostable lipase of the invention may be a thermostable lipase with an optimal temperature of about 28, 29, 30, 31, 32, 33, 34, 35, 36, 37, 38, 39, 40° C. or more. In yet other embodiments, the thermostable lipase of the invention may be a thermostable lipase with an optimal temperature of about 35, 36, 37, 38, 39, 40, 41, 42, 43, 44, 45, 46, 47, 48, 49, 50° C. or more. In other embodiments, the thermostable lipase of the invention may be a thermostable lipase with an optimal temperature of about 40, 41, 42, 43, 44, 45, 46, 47, 48, 49, 50, 51° C. or more. In still other embodiments, the thermostable lipase of the invention may be a thermostable lipase with an optimal temperature of about 48, 49, 50, 51, 52, 53, 54, 55, 56, 57, 58, 59, 60° C. or more. In some embodiments, the thermostable lipase of the invention may be a thermostable lipase with an optimal temperature of about 55, 56, 57, 58, 59, 60, 61, 62, 63, 64, 65, 66, 67, 68, 69, 70° C. or more. In yet other embodiments, the thermostable lipase of the invention may be a thermostable lipase with an optimal temperature of about 65, 66, 67, 68, 69, 70, 71, 72, 73, 74, 75, 76, 77, 78, 79, 80, 81, 82, 83, 84, 85° C. or more. In other embodiments, the thermostable lipase of the invention may be a thermostable lipase with an optimal temperature of about 80, 81, 82, 83, 84, 85, 86, 87, 88, 89, 90, 91 92, 93, 94, 94, 96° C. or more.

A thermostable lipase of the invention may be a naturally occurring lipase from thermophilic microorganisms that subsist in high temperature environments. Alternatively, a thermostable lipase of the invention may be a lipase that was genetically engineered for thermostability. Non-limiting examples of thermostable lipases that may be used in the invention include the thermostable lipases listed in Table A. In preferred embodiments, the thermostable lipase may be a thermostable lipase listed in Table 3. In one embodiment, the thermostable lipase is the lipase encoded by the gtl nucleic acid sequence of *Geobacillus* sp. Strain T1. In another embodiment, the thermostable lipase is the lipase encoded by the tll nucleic acid sequence of *Thermomyces lanuginosus*. In yet another embodiment, the thermostable lipase is the lipase encoded by the sll nucleic acid sequence of *Streptomyces lividans*. In another embodiment, the thermostable lipase is the lipase encoded by the btl nucleic acid sequence of *Bacillus stearothermophilus* P1. In an additional embodiment, the thermostable lipase is the lipase encoded by the bsl nucleic acid sequence of *Bacillus subtilis* strain 168. In yet another embodiment, the thermostable lipase is the lipase encoded by the ggl nucleic acid sequence of *Galactomyces geotrichum* Y05. In an exemplary embodiment, the thermostable lipase is the lipase encoded by the fnl nucleic acid sequence of *Fervidobacterium nodosum* Rt17-B1.

TABLE A

Thermostable lipases.

| Organism | Lipase accession | Protein id | Lipase sequence |
|---|---|---|---|
| *Bacillus stearothermophilus* str. P1 SEQ ID NO: 1 | AF237623 | AAF40217.1 | MMKGCRVMVVLLGLCFVFGLSVPGGR TEAASLRANDAPIVLLHGFTGWGREEM FGFKYWGGVRGDIEQWLNDNGYRTYT LAVGPLSSNWDRACEAYAQLVGGTVD YGAAHAAKHGHARFGRTYPGLLPELKR GGRIHIIAHSQGGQTARMLVSLLENGSQ EEREYAKAHNVSLSPLFEGGHHFVLSV TTIATPHDGTTLVNMVDFTDRFFDLQKA VLEAAAVASNVPYTSQVYDFKLDQWGL RRQPGESFDHYFERLKRSPVWTSTDT ARYDLSVSGAEKLNQWVQASPNTYYLS FSTERTYRGALTGNHYPELGMNAFSAV VCAPFLGSYRNPTLGIDSHWLENDGIV NTISMNGPKRGSNDRIVPYDGTLKKGV WNDMGTYNVDHLEIIGVDPNPSFDIRAF YLRLAEQLASLQP |
| *Bacillus stearothermophilus* str. T-6; NCIMB 4022 SEQ ID NO: 2 | AF429311 | AAL28099.1 | MMKCCRRVALVLLGLWFVFCISVLGGR AEAAASRANDAPIVLLHGFTGWGREEM FGFKYWGGVRGDIEQWLNDNGYRTYT LAVGPLSSNWDRACEAYAQLVGGTVD YGAAHAAKHGHARFGRTYPGLLPELKR GGRIHIIAHSQGGQTARMLVSLLENGSQ EEREYAKAHNVSLSPLFEGGHHFVLSV TTIATPHDGTTLVNMVDFTDRFFDLQKA VLKAAAVASNVPYTSQVYDFKLDQWGL RRQPGESFDQYFERLKRSPVWTSTDT ARYDLSVPGAEKLNQWVKASPNTYYLS FATERTYRGALTGNYYPELGMNAFSAV VCAPFLGSYRNATLGIDDRWLENDGIV NTFSMNGPKRGSTDRIVPYDGTIKKGV WNDMGTYNVDHLEVIGVDPNPLFDIRA FYLRLAEQLASLQP |
| *Geobacillus stearothermophilus* sp. TW1 SEQ ID NO: 3 | AY786185 | AAX11388.1 | MMKGCRVMFVLLGLWLVFGLSVPGGR AEAATSRANDAPIVLLHGFTGWGREEM FGFKYWGGVRGDIEQWLNDNGYRTYT LAVGPLSSNWDRACEAYAQLVGGTVD YGAAHAAKHGHARFGRTYPGLLPELKR GGRIHIIAHSQGGQTARMLVSLLENGSQ EEREYAKAHNVSLSPLFEGGHHFVLSV TTIATPHDGTTLVNMVDFTDRFFDLQKA VLEAAAVASNVPYTSQVYDFKLDQWGL RRQPGESFDHYFERLKRSPVWTSTDT ARYDLSVSGAEKLNQWVQASPNTYYLS FATERTYRGALTGNYYPELGMNAFSAV VCAPFLGSYRNPTLGIDDRWLENDGIV NTVSMNGPKRGSSDRIVPYDGALKKGV WNDMGTYNVDHLEIIGVDPNPSFDIRAF YLRLAEQLASLQP |

TABLE A-continued

Thermostable lipases.

| Organism | Lipase accession | Protein id | Lipase sequence |
|---|---|---|---|
| Geobacillus stearothermophilus strain 5 SEQ ID NO: 4 | DQ923401 | ABK27875.1 | GLVVGYGLCSAYRSRGAAEAASPRAN DAPIVLLHGFTGWGREEMLGFKYWGG VRGDIEQWLNDNGYRTYTLAVGPLSSN WDRACEAYAQLVGGTVDYGAAHAAKH GHARFGRPYPGLLAGIERRKPASIQSV HRPREGRRAGMLGFRSLGETGGQRR GGEYAQGSHNRGRLVGPFVLRGGHPF LCRAVTDHSQTPSGREPTPCKHGLISP DPLFLTCQKGGAWKRRLVRQPTAPYH KRNYTILSLGPMGGLRREPRRIRSTIYF GTAQAPPLSGHRTRYPPRYDLIRSRGL RRGIRLGESQPNTYYLELFYPNGRIEEL |
| Geobacillus stearothermophilus strain str. ARM1 SEQ ID NO: 5 | EF042975 | ABK34427.1 | MMKCCRRVALVLLGLWFVFCISVLGGR AEAAASRANDAPIVLLHGFTGWGREEM FGFKYWGGVRGDIEQWLNDNGYRTYT LAVGPLSSNWDRACEAYAQLVGGTVD YGAAHAAKHGHARFGRTYPGLLPELKR GGRIHIIAHSQGGQTARMLVSLLENGSQ EEREYAKAHNVSLSPLFEGGHHFVLRV TTIATPHDGTTLVNMVDFTDRFFDLQKA VLKAAAVASNVPYTSQVYDFKLDQWGL RRQPGESFDQYFERLKRSPVWTSTDT ARYDLSVPGAEKLNQWVKASPNTYYLS FATERTYRGALTGNYYPELGMNAFSAV VCAPFLGSYRNATLGIDDRWLENDGIV NTFSMNGPKRGSTDRIVPYDGTIKKGV WNDMGTYNVDHLEVIGVDPNPLFDIRA FYLRLAEQLASLQP |
| Bacillus stearothermophilus str. L1 SEQ ID NO: 6 | U78785 | AAC12257.1 | MMKGCRVMVVLLGLWFVFGLSVPGGR TEAASPRANDAPIVLLHGFTGWGREEM LGFKYWGGVRGDIEQWLNDNGYRTYT LAVGPLSSNWDRACEAYAQLVGGTVD YGAAHAANDGHARFGRTYPGLLPELKR GGRVHIIAHSQGGQTARMLVSLLENGS QEEREYAKEHNVSLSPLFEGGHRFVLS VTTIATPHDGTTLVNMVDFTDRFFDLQK AVLEAAAVASNAPYTSEIYDFKLDQWG LRREPGESFDHYFERLKRSPVWTSTDT ARYDLSVPGAETLNRWVKASPNTYYLS FSTERTYRGALTGNYYPELGMNAFSAI VCAPFLGSYRNAALGIDSHWLGNDGIV NTISMNGPKRGSNDRIVPYDGTLKKGV WNDMGTYKVDHLEVIGVDPNPSFNIRA FYLRLAEQLASLRP |
| Thermophilic fungus Thermomyces lanuginosus isolate T 03 SEQ ID NO: 7 | EU004197 | ABV69592.1 | MRSSLVLFFLSAWTALARPVRRAVPQD LLDQFELFSQYSAAAYCAANNHAPVGS DVTCSENVCPEVDAADATFLYSFEDSG LGDVTGLLALDNTNKLIVLSFRGSRSVE NWIANLAADLTEISDICSGCEGHVGFVT SWRSVADTIREQVQNAVNEHPDYRVVF TGHSLGGALATIAAAALRGNGYNIDVFS YGAPRVGNRAFAEFLTAQTGGTLYRIT HTNDIVPRLPPRDWGYSHSSPEYWVTS GNDVPVTANDITVVEGIDSTDGNNQGNI PDIPSHLWYFGPISECD |
| Galactomyces geotrichum str. Y05 SEQ ID NO: 8 | DQ841279 | ABI13535.1 | MVSKSFFLAAAVNVVGVLAQAPTAVLN DNEVITGVLEGQVDTFKGIPFADPPVAD LRFKHPQSFTGSYQGLQAKDFSSACM QIDPYNSLTILDNVLNLGKIIPEDFRGPIY DMAKGTVSMSEDCLYLNVFRPAGTKPS DKLPVMVWIYGGAFIYGSSAAYPGNGY VKESVKMGQPVVFVSINYRTGPFGFLG GDGITAEGNTNSGLHDQRKGLEWVSD NIANFOGDPDKVMIFGESAGAMSVGHO LIAYGGDNTYNGKPLFHSAILQSGGPLP YYDSTSVGPEKAYNRFAEYAGCDTTAS DVDILQCLRSKSSQVLHDAQNSYDLKD LFGLLPEFLGFGPRPDGDILPGSAFELY RSGRYAKVPYITGNQEDEGTVLAPVAL NATTTPHVKKWLQYIFNQASDSSIERVL ELYPQTLSEGSPFRTGILNALTPQFKRV AAILSDLLFQSPRRIMLNATKDVNRWTY ISTHLHNLVPFLGTFHGNELVIQFNVNV |

TABLE A-continued

Thermostable lipases.

| Organism | Lipase accession | Protein id | Lipase sequence |
|---|---|---|---|
| | | | GPADSYLRYFISFANHHDPNVGTNLLT WNKYTDEGKEMLEIKMFDNSMRTDDF RIEGISNFESDVNLYG |
| Geobacillus thermocatenulatus str. DSM 730 SEQ ID NO: 9 | X95309 | CAA64621.1 | MMKGCRVMVVLLGLWFVFGLSVPGGR TEAASPRANDAPIVLLHGFTGWGREEM LGFKYWGGVRGDIEQWLNDNGYRTYT LAVGPLSSNWDRACEAYAQLVGGTVD YGAAHAAKHGHARFGRTYPGLLPELKR GGRVHIIAHSQGGQTARMLVSLLENGS QEEREYAKAHNVSLSPLFEGGHHFVLS VTTIATPHDGTTLVNMVDFTDRFFDLQK AVLKAAAVASNVPYTSQVYDFKLDQWG LRRQPGESFDHYFERLKRSPVWTSTDT ARYDLSIPGAEKLNQWVQASPNTYYLS FSTERTHRGALTGNYYPELGMNAFSAV VCAPFLGSYRNEALGIDDRWLENDGIV NTVSMNGPKRGSSDRIVPYDGTLKKGV WNDMGTCNVDHLEVIGVDPNPSFDIRA FYLRLAEQLASLRP |
| Geobacillus thermoleovorans str. ID-1 SEQ ID NO: 10 | AF134840 | AAD30278.1 | MKCCRVMFVLLGLWLVFGLSVSGGRA EAAASRANDAPIVLLHGFTGWGREEMF GFKYWGGVRGDIEQWLNDNGYRTYTL AVGPLSSNWDRACEAYAQLVGGTVDY GAAHAAKHGHARFGRTYPGLLPELKRG GRIHIIAHSQGGQTARMLVSLLENGSQE EREYAKAHNVSLSPLFEGGHHFVLSVT TIATPHDGTTLVNMVDFTDRFFDLQKAV LEAAAVASNVPYTSQVYDFKLDQWGLR RQPGESFDHYFERLKRSPVWTSTDTA RYDLSVSGAEKLNQWVQASPNTYYLSF ATERTYRGALTGNYYPELGMNAFSAVV CAPFLGSYRNPTLGIDDRWLENDGIVN TVSMNGPKRGSSDRIVPYDGALKKGV WNDMGTYNVDHLEIIGVDPNPSFDIRAF YLRLAEQLASLRP |
| Geobacillus thermoleovorans str. NY SEQ ID NO: 11 | AY095260 | AAM21774.1 | MKGCRVMFVLLGLWLVFGLSVPGGRA EAATSRANDAPIVLLHGFTGWGREEMF GFKYWGGVRGDIEQWLNDNGYRTYTL AVGPLSSNWDRACEAYAQLVGGTVDY GAAHAAKHGHARFGRTYPGLLPELKRG GRIHIIAHSQGGQTARMLVSLLENGSQE EREYAKAHNVSLSPLFEGGHHFVLSVT TIATPHDGTTLVNMVDFTDRFFDLQKAV LEAAAVASNAPYTSEIYDFKLDQWGLR REPGESFDHYFERLKRSPVWTSTDTAR YDLSVPGAETLNRWVKASPNTYYLSFS TERTYRGALTGNYYPELGMNAFSAIVC APFLGSYRNAALGIDSHWLENDGIVNTI SMNGPKRGSSDRIVPYDGALKKGVWN DMGTYNVDHLEIIGVDPNPSFDIRAFYL RLAEQLASFGP |
| Geobacillus thermoleovorans str. IHI-91 SEQ ID NO: 12 | AY149997 | AAN72417.1 | MKCCRVMFVLLGLWLVFGLSVSGGRA EAAASRANDAPIVLLHGFTGWGREEMF GFKYWGGVRGDIEQWLNDNGYRTYTL AVGPLSSNWDRACEAYAQLVGGTVDY GAAHAAKHGHARFGRTYPGLLPELKRG GRIHIIAHSQGGQTARMLVSLLENGSQE EREYAKAHNVSLSPLFEGGHHFVLSVT TIATPHDGTTLVNMVDFTDRFFDLQKAV LEAAAVASNVPYTSQVYDFKLDQWGLR RQPGESFDHYFERLKRSPVWTSTDTA RYDLSVSGAEKLNQWVQASPNTYYLSF ATERTYRGALTGNYYPELGMNAFSAVV CAPFLGSYRNPTLGIDDRWLENDGIVN TVSMNGPKRGSSDRIVPYDGALKKGV WNDMGTYNVDHLEIIGVDPNPSFDIRAF YLRLAEQLASLRP |
| Geobacillus thermoleovorans str. YN SEQ ID NO: 13 | DQ298518 | ABC48693.1 | MKCCRVMFVLLGLWLVFGLSVPGGRA EAATSRANDAPIVLLHGFTGWGREEMF GFKYWGGVRGDIEQWLNDNGYRTYTL AVGPLSSNWDRACEAYAQLVGGTVDY GAAHAAKHGHARFGRTYPGLLPELKRG GRIHIIAHSQGGQTARMLVSLLENGSQE EREYAKAHNVSLSPLFEGGHHFVLSVT TIATPHDGTTLVNMVDFTDRFFDLQKAV |

TABLE A-continued

Thermostable lipases.

| Organism | Lipase accession | Protein id | Lipase sequence |
|---|---|---|---|
| | | | LEAAAVASNAPYTSEIYDFKLDQWGLR REPGESFDHYFERLKRSPVWTSTDTAR YDLSVPGAETLNRWVKASPNTYYLSFS TERTYRGALTGNYYPEFGMNAFSAIVC APFFGSYRNAALGIDSHWLENDGIVNTI SMNGPKRGSSDRIVPYDGALKKGVWN DMGTYNVDHLEIIGVDPNPSFDIRAFYL RLAEQLASLRP |
| *Geobacillus thermoleovorans* SEQ ID NO: 14 | EF123044 | ABL74242.1 | MKGCRVMFVLLGLWLVFGLSVPGGRA EAATSRANDAPIVLLHGFTGWGREEMF GFKYWGGVRGDIEQWLNDNGYRTYTL AVGPLSSNWDRACEAYAQLVGGTVDY GAAHAAKHGHARFGRTYPGLLPELKRG GRIHIIAHSQGGQTARMLVSLLENGSQE EREYAKAHNVSLSPLFEGGHHFVLSVT TIATPHDGTTLVNMVDFTDRFFDLQKAV LEAAAVASNAPYTSEIYDFKLDQWGLR REPGESFDHYFERLKRSPVWTSTDTAR YDLSVPGAETLNRWVKASPNTYYLSFS TERTYRGALTGNYYPELGMNAFSAIVC APFLGSYRNAALGIDSHWLENDGIVNTI SMNGPKRGSSDRIVPYDGALKKGVWN DMGTYNVDHLEIIGVDPNPSFDIRAFYL RLAEQLASFGP |
| *Bacillus* sp. NG-27 str. NG-27 SEQ ID NO: 15 | AF015445 | AAB70918.1 | MLKTLRKPFIAGLALSLLLTGGASSVFA QGNGQAGPPKGGIFKEGEKGNGNVQP FAWQVASLADRYEESFDIGAAVEPHQL NGRQGKVLKHHYNSIVAENAMKPISLQ PEEGVFTWDGADAIVEFARKNNMNLRF HTLVWHNQVPDWFFLDEEGNPMVEET NEAKRQANKELLLERLETHIKTVVERYK DDVTAWDVVNEVVDDGTPNERGLRES VWYQITGDEYIRVAFETARKYAGEDAKL FINDYNTEVTPKRDHLYNLVQDLLADGV PIDGVGHQAHIQIDWPTIDEIRTSMEMF AGLGLDNQVTELDVSLYGWPPRPAFPT YDAIPQERFQAQADRYNQLFELYEELD ADLSSVTFWGIADNHTWLDDRAREYND GVGKDAPFVFDPNYRVKPAFWRIID |
| uncultured bacterium from metagenomic library colon IAF5-2 SEQ ID NO: 16 | EU660533 | ACC95208.1 | MPITARNTLASLLLASSALLLSGTAFAAN PPGGDPDPGCQTDCNYQRGPDPTDAY LEAASGPYTVSTIRVSSLVPGFGGGTIH YPTNAGGGKMAGIVVIPGYLSFESSIEW WGPRLASHGFVVMTIDTNTIYDQPSQR RDQIEAALQYLVNQSNSSSSPISGMVD SSRLAAVGWSMGGGGTLQLAADGGIK AAIALAPWNSSINDFNRIQVPTLIFACQL DAIAPVALHASPFYNRIPNTTPKAFFEM TGGDHWCANGGNIYSALLGKYGVSWM KLHLDQDTRYAPFLCGPNHAAQTLISEY RGNCPY |
| *Bacillus* sp. TP10A.1 str. TP10A.1 SEQ ID NO: 17 | AF141874 | AAF63229.1 | MMKCCRRVALVLLGLWLVFCLSVPGG RAEAAASRANDAPIVLLHGFTGWGREE MFGFKYWGGVRGDIEQLLNAQGYRTY TLAVGPLSSNWDRACEAYAQLVGGTV DYGAAHAAKHGHARFGRTYPGLLPELK RGGRVHIIAHSQGGQTARMLVSLLENG SKEEREYAKAHNVSLSPLFEGGHNFVL SVTTIATPHDGTTLVNMVDFTDRFFDLQ KAVLKAAAVASNVPYTSQVYDFKLDQW GLRRQPGESFDQYFERLKQSPVWTSA DTARYDLSVPGAEALNQWVQASPNTY YLSFATERTYRGALTGNYYPELGMNVF SAAVCAPFLGSYRNAALGIDDRWLEND GIVNTFSMNGPKRGSTDRIVPYDGTLK KGVWNDMGTYNVDHLEVIGVDPNPLF DIHAFYLRLAEQLASLRP |
| *Aneurinibacillus thermoaerophilus* strain HZ SEQ ID NO: 18 | GU272057 | ADC84241.1 | MQKERKNQYPIVLVHGFAGWGRDEML GVKYWGGMHDIQEDLKQYGYETHTAV VGPFSSNWDRACELYAQLVGGTVDYG AAHAEKYGHDRFGRTYPGLLKNWDGE HKIHLIGHSMGGQTVRVLTQLLKEGSQ EEREYAKKHGVQLSPLFEGGKSWVHS VTTIATPNDGTTLADVVTQLIPAAQQIM GLAAAVSGNTNVPVYDFKLDQWGLKR |

TABLE A-continued

Thermostable lipases.

| Organism | Lipase accession | Protein id | Lipase sequence |
|---|---|---|---|
| | | | KAGESFVHYADRVWNSGIWTNTKDISA WDLKPEGAKELNNWVKAQPDVYYFSY SGEATFRSLITGHHLPDLTMNKLITPFGI FLGCYGSDEKWWQNDGIVNTISMNGP KLGSTDEIVPYDGTPKIGKWNDMGIQE NWDHADYIGLSLSYVLGIEKIEDFYRGV ADMLGSLSVR |
| *Bacillus* sp. Tosh str. Tosh SEQ ID NO: 19 | AY095262 | AAM21775.1 | MMKCCRVMFVLLGLWLVFGLSVPGGR AEAATSRANDAPIVLLHGFTGWGREEM FGFKYWGGVRGDIEQWLNDNGYRTYT LAVGPLSSNWDRACEAYAQLVGGTVD YGAAHAAKHGHARFGRTYPGLLPELKR GGRIHIIAHSQGGQTARMLVSLLENGSQ EEREYAKAHNVSLSPLFEGGHHFVLSV TTIATPHDGTTLVNMVDFTDRFFDLQKA VLEAAAVASNAPYTSEIYDFKLDQWGL RREPGESFDHYFERLKRSPVWTSTDTA RYDLSVPGAETLNRWVKASPNTYYLSF STERTYRGALTGNYYPELGMNAFSAIV CAPFLGSYRNAALGIDSHWLENDGIVN TISMSGPKRGSSDRIVPYDGALKKGVW NDMGTYNVDHLEIIGVDPNPSFDIRAFY LRLAEQLASLRP |
| *Geobacillus zalihae* strain T1 SEQ ID NO: 20 | AY260764 | AAO92067.2 | MKCCRIMFVLLGLWFVFGLSVPGGRTE AASLRANDAPIVLLHGFTGWGREEMFG FKYWGGVRGDIEQWLNDNGYRTYTLA VGPLSSNWDRACEAYAQLVGGTVDYG AAHAAKHGHARFGRTYPGLLPELKRGG RIHIIAHSQGGQTARMLVSLLENGSQEE REYAKAHNVSLSPLFEGGHHFVLSVTTI ATPHDGTTLVNMVDFTDRFFDLQKAVL EAAAVASNVPYTSQVYDFKLDQWGLR RQPGESFDHYFERLKRSPVWTSTDTA RYDLSVSGAEKLNQWVQASPNTYYLSF STERTYRGALTGNHYPELGMNAFSAVV CAPFLGSYRNPTLGIDDRWLENDGIVN TVSMNGPKRGSSDRIVPYDGTLKKGV WNDMGTYNVDHLEIIGVDPNPSFDIRAF YLRLAEQLASLQP |
| *Bacillus subtilis* subsp. subtilis str. 168 SEQ ID NO: 21 | NC_000964 | NP_388152.1 | MKFVKRRIIALVTILMLSVTSLFALQPSA KAAEHNPVVMVHGIGGASFNFAGIKSY LVSQGWSRDKLYAVDFWDKTGTNYNN GPVLSRFVQKVLDETGAKKVDIVAHSM GGANTLYYIKNLDGGNKVANVVTLGGA NRLTTGKALPGTDPNQKILYTSIYSSAD MIVMNYLSRLDGARNVQIHGVGHIGLLY SSQVNSLIKEGLNGGGQNTN |
| *Bacillus subtilis* subsp. subtilis str. 168 SEQ ID NO: 22 | NC_000964 | NP_388716 | MKKVLMAFIICLSLILSVLAAPPSGAKAE SVHNPVVLVHGISGASYNFFAIKNYLISQ GWQSNKLYAIDFYDKTGNNLNNGPQLA SYVDRVLKETGAKKVDIAHSMGGANT LYYIKYLGGGNKIQNVVTLGGANGLVSS TALPGTDPNQKILYTSIYSLNDQIVINSLS RLQGARNIQLYGIGHIGLLSNSQVNGYI KEGLNGGGLNTN |
| *Geobacillus kaustophilus* HTA426 str. HTA426 SEQ ID NO: 23 | BA000043 | BAD76271.1 | MMKCCRRVALVLLGLWFVFCISVLGGR AEAAASRANDAPIVLLHGFTGWGREEM FGFKYWGGVRGDIEQWLNDNGYRTYT LAVGPLSSNWDRACEAYAQLVGGTVD YGAAHAAKHGHARFGRTYPGLLPELKR GGRIHIIAHSQGGQTARMLVSLLENGSQ EEREYAKAHNVSLSPLFEGGHHFVLSV TTIATPHDGTTLVNMVDFTDRFFDLQKA VLEAAAVASNVPYTSQVYDFKLDQWGL RRQPGESFDHYFERLKRSPVWTSTDT ARYDLSVPGAEKLNQWVKASPNTYYLS FATERTYRGALTGNYYPELGMNAFSAV VCAPFLGSYRNATLGIDDRWLENDGIV NTFSMNGPKRGSTDRIVPYDGTIKKGV WNYMGTYNVDHLEVIGVDPNPLFDIRA FYLRLAEQLASLQP |
| *Bacillus* sp. 42 str. 42 SEQ ID NO: 24 | AY787835 | AAV35102.1 | MKCCRIMFVLLGLWFVFGLSVPGGRTE AASLRANDAPIVLLHGFTGWGREEMFG FKYWGGVRGDIEQWLNDNGYRTYTLA VGPLSSNWDRACEAYAQLVGGTVDYG |

TABLE A-continued

Thermostable lipases.

| Organism | Lipase accession | Protein id | Lipase sequence |
|---|---|---|---|
| | | | AAHAAKHGHARFGRTYPGLLPELKRGG RIHIIAHSQGGQTARMLVSLLENGSQEE REYAKAHNVSLSPWFEGGHHFVLSVTT IATPHDGTTLVNMVDFTDRFFDLQKAVL EAAAVASNVPYTSQVYDFKLDQWGLR RQPGESFDHYFERLKRSPVWTSTDTA RYDLSVSGAEKLNQWVQASPNTYYLSF STERTYRGALTGNHYPELGMNAFSAVV CAPFLGSYRNPTLGIDDRWLENDGIVN TVSMNGPKRGSSDRIVPYDGTLKKGV WNDMGTYNVDHLEIIGVDPNPSFDIRAF YLRLAEQLASLRP |
| Bacillus sp. L2 SEQ ID NO: 25 | AY855077 | AAW47928.1 | MKCCRIMFVLLGLWFVFGLSVPGGRTE AASLRANDAPIVLLHGFTGWGREEMFG FKYWGGVRGDIEQWLNDNGYRTYTLA VGPLSSNWDRACEAYAQLVGGTVDYG AAHAAKHGHARFGRTYPGLLPELKRGG RIHIIAHSQGGQTARMLVSLLENGSQEE REYAKAHNVSLSPLFEGGHHFVLSVTTI ATPHDGTTLVNMVDFTDRFFDLQKAVL EAAAVASNVPYTSQVYDFKLDQWGLR RQPGESFDHYFERLKRSPVWTSTDTA RYDLSVSGAEKLNQWVQASPNTYYLSF STERTYRGALTGNHYPELGMNAFSAVV CAPFLGSYRNPTLGIDDRWLENDGIVN TVSMNGPKRGSSDRIVPYDGTLKKGV WNDMGTYNVDHLEIIGVDPNPSFDIRAF YLRLAEQLASLLP |
| Geobacillus sp. SF1 str. SF1 SEQ ID NO: 26 | DQ009618 | AAY82869.1 | MMKGCRVMFVLLGLWFVFGLSVPGGR TEAASPRANDAPIVLLHGFTGWGREEM LGFKYWGGVRGDIEQWLNDNGYRTYT LAVGPLSSNWDRACEAYAQLVGGTVD YGAAHAAKHGHARFGRTYPGLLPELKR GGRVHIIAHSQGGQTARMLVSLLENGS QEEREYAKEHNVSLSPLFEGGHRFVLS VTTIATPHDGTTLVNMVDFTDRFFDLQK AVLEAAAVASNAPYTSEIYDFKLDQWG LRREPGESFDHYFERLKRSPVWTSTDT ARYDLSVSGAEKLNQWVQASPNTYYLS FATERTYRGALTGNYYPELGMNAFSAV VCAPFLGSYRNPTLGIDDRWLENDGIV NTVSMNGPKRGSSDRIVPYDGALKKGV WNDMGTYNVDHLEIIGVDPNPSFDIRAF YLRLAEQLASLQP |
| Streptomyces lividans SEQ ID NO: 27 | HM049169 | AD178874.1 | MPMKINRYAIGSAALAAGLLMSSAAFAV NPGGGGSGFASLYNRAESDGRCSVTR LNVGSSTFYIPRDPSNPARFNVLVWG NGTGGNSLTYATLLESVASHCIAVAAAN TANSGTGVEMQEAYNSLRSRYGNILGS KVCTAGHSQGGGGSFNAANRIGANCVI PVQPDTRFTTRIYSPLASHVEVITLWGQ IDTLAPASGNRSNVERASTILTQVETSG EGHFAPVSGRGGKIGTMFRMANIAQLS NDPATAQEFRRAFWGPTTDYTASTSHP DISEVRRNAAAQATTP |
| Fervidobacterium nodosum str. Rt17-B1 SEQ ID NO: 28 | ABS61180 | ABS61180.1 | MYYNNGIPVYRTIKEIKPFFEYTKVSEVY WERPVPEIVKIRDGELSVVLIHGIDPME VNGSWTLYKEYFVNTWNSLLPKNCGLY IFIYPTLDVPLEETAKILVDEIIKLNKKVNI YAHSMGGILLRYVLQNEEFREFVNKIIFA GTPHLGTPLANFVVLDKSVLKFHPKWDI IKTVILMANTAWVFIDAPNYKYLTFGFEK PEIPENINFMNFAAKINANTSSIVKNLINT DFFSSIALQILESTIKIIYPKDSDFTQNDG MVPLFSATYYGNEKVFEGFDHADLAISE TIVKEAIKYFFGE |
| Geobacillus sp. SBS-4S str. SBS-4S SEQ ID NO: 29 | AB457187 | BAH28804.1 | MAASRANDAPIVLLHGFTGWGREEMF GFKYWGGVRGDIEQWLNDNGYRTYTL AVGPLSSNWDRACEAYAQLVGGTVDY GAAHAAKHGHARFGRTYLGLLPELKRG GRIHIIAHSQGGQTARMLVSLLENGSQE EREYAKAHNVSLSPLFEGGHHFVLSVT TIATPHDGTTLVNMVDFTDRFFDLQKAV LEAAAVASNVPYTSQVYDFKLDWGLR RQPGESFDHYFERLKRSPVWTSTDTA |

TABLE A-continued

Thermostable lipases.

| Organism | Lipase accession | Protein id | Lipase sequence |
|---|---|---|---|
| | | | RYDLSVSGAEKLNQWVQASPNTYYLSF ATERTYRGALTGNYYPELGMNAFSAVV CAPFLGSYRNPTLGIDDRWLENDGIVN TVSMNGPKRGSSDRIVPYDGALKKGV WNDMGTYNVDHLEIIGVDPNPSFDIRAF YLRLAEQLASLQP |

In some embodiments, the recombinant photosynthetic microorganism of the invention may express one, two three, four, five, six, seven, eight or lipases. For instance, the microorganism may express more than one lipase described in Table A or more than one lipase described in Table 3.

To ensure that the synthesis of a thermostable lipase does not result in the premature lysis of a photosynthetic microorganism, the enzyme may be placed under the control of an inducible promoter as described in Section 1(c) below.

(c) Nucleic Acid Constructs for Expression of Thermostable Lipase

A photosynthetic microorganism of the invention comprises a nucleic acid cassette comprising an inducible promoter operably-linked to a nucleic acid encoding a thermostable lipase. A nucleic acid cassette of the invention may be chromosomally integrated, or may be expressed on an extra-chromosomal vector.

Methods of making a photosynthetic microorganism of the invention are known in the art. Generally speaking, a photosynthetic microorganism is transformed with a nucleic acid cassette of the invention. Methods of transformation are well known in the art, and may include electroporation, natural transformation, and calcium chloride mediated transformation. Methods of screening for and verifying chromosomal integration are also known in the art.

In a preferred embodiment, the photosynthetic microorganism is a cyanobacterium, and a method of making a cyanobacterium of the invention may comprise first transforming the cyanobacterium with a vector comprising, in part, an antibiotic-resistance marker and a negative selection marker. Chromosomal integration may be selected for by selecting for antiobiotic resistance. Next, the antibiotic-resistant strain is transformed with a similar vector comprising the target genes of interest. Chromosomal integration of the target genes may be selected for by selecting for the absence of the negative marker. For instance, if the negative marker is sacB, then one would select for sucrose resistance. For more details, see Kang et al., J. Bacteriol. (2002) 184(1):307-12, Sun et al., Appl. Environ. Microbiol. (2008) 74:4241-45, and Liu et al., PNAS (2011) 108:6899-6904, hereby incorporated by reference in their entirety.

In other embodiments, the photosynthetic microorganism is a eukaryotic alga. Nucleic acid sequences may be expressed in the nucleus or the plastid of eukaryotic algal cells. As is generally recognized in the art, chloroplasts use bacterial means for expression of nucleic acid sequences and for protein synthesis. As such, methods for regulated or constitutive expression of nucleic acid sequences in algal chloroplasts are as described for expression of nucleic acid sequences in bacteria. Methods of transforming an alga and to express nucleic acid sequences from the nucleus or the plastid of the algal cell are known in the art. For more details, see Wang et al., J. Genet. Genomics (2009) 36:387-398, Radako-vits et al., Eukaryotic Cell (2010) 9(4):486-501, Newell et al. (2003) 12:631-634, hereby incorporated by reference in their entirety.

i. Nucleic Acid Constructs

The present invention encompasses a photosynthetic microorganism comprising a nucleic acid cassette that, when expressed, induces the degradation of the lipid membrane or the peptidoglycan layer of a photosynthetic microorganism or the plastid of a photosynthetic microorganism. Typically, the nucleic acid cassette comprises an inducible promoter operably-linked to a nucleic acid sequence encoding a thermostable lipase capable of hydrolyzing lipid membranes of a photosynthetic microorganism into free fatty acids. Each component of the above nucleic acid construct is discussed in more detail below.

Methods of making a nucleic acid cassette of the invention are known in the art. Additional information may be found in Sambrook et al., Molecular Cloning: A Laboratory Manual (New York: Cold Spring Harbor Laboratory Press, 1989).

ii. Promoters

A nucleic acid cassette of the present invention comprises an inducible promoter operably-linked to a nucleic acid encoding a thermostable lipase. In some embodiments, the cassette further comprises a second constitutive promoter operably-linked to a nucleic acid encoding the thermostable lipase. When a nucleic acid comprises a first and a second promoter, the promoters may read in opposite directions, or may read in the same direction.

A. First Inducible Promoter

In certain embodiments, a nucleic acid of the invention encompasses an inducible promoter. Non-limiting examples of inducible promoters may include, but are not limited to, those induced by expression of an exogenous protein (e.g., T7 RNA polymerase, SP6 RNA polymerase), by the presence of a small molecule (e.g., IPTG, galactose, tetracycline, steroid hormone, abscisic acid), by absence of small molecules (e.g., $CO_2$, iron, nitrogen), by metals or metal ions (e.g., copper, zinc, cadmium, nickel), and by environmental factors (e.g., heat, cold, stress, light, darkness), and by growth phase. In each of the above embodiments, the inducible promoter is preferably tightly regulated such that in the absence of induction, substantially no transcription is initiated through the promoter. Additionally, induction of the promoter of interest should not typically alter transcription through other promoters. Also, generally speaking, the compound or condition that induces an inducible promoter should not be naturally present in the organism or environment where expression is sought.

In one embodiment, the inducible promoter is induced by limitation of the $CO_2$ supply to the cyanobacteria culture. By way of non-limiting example, the inducible promoter may be variants of the promoter sequences of Synechocystis PCC 6803 that are up-regulated under $CO_2$-limitation conditions, such as the promoters for cmp genes, ntp genes, ndh genes, sbt genes, chp genes, and rbc genes. In exemplary embodiments, the inducible promoter is the $P_{cmp}$ promoter wherein the inducible promoter is induced in the absence of $CO_2$.

In one embodiment, the inducible promoter is induced by iron starvation or by entering the stationary growth phase. By way of non-limiting example, the inducible promoter may be variant sequences of the promoter sequence of the *Synechocystis* PCC 6803 isiA gene. In some embodiments, the inducible promoter may be variant sequences of the promoter sequence of cyanobacterial genes that are up-regulated under Fe-starvation conditions such as isiA, or when the culture enters the stationary growth phase, such as isiA, phrA, sigC, sigB, and sigH genes.

In one embodiment, the inducible promoter is induced by a metal or metal ion. By way of non-limiting example, the inducible promoter may be induced by copper, zinc, cadmium, mercury, nickel, gold, silver, cobalt, and bismuth or ions thereof. In one embodiment, the inducible promoter is induced by nickel or a nickel ion. In an exemplary embodiment, the inducible promoter is induced by a nickel ion, such as $Ni^{2+}$. In another exemplary embodiment, the inducible promoter is the nickel inducible promoter from *Synechocystis* PCC 6803. In another embodiment, the inducible promoter may be induced by copper or a copper ion. In yet another embodiment, the inducible promoter may be induced by zinc or a zinc ion. In still another embodiment, the inducible promoter may be induced by cadmium or a cadmium ion. In yet still another embodiment, the inducible promoter may be induced by mercury or a mercury ion. In an alternative embodiment, the inducible promoter may be induced by gold or a gold ion. In another alternative embodiment, the inducible promoter may be induced by silver or a silver ion. In yet another alternative embodiment, the inducible promoter may be induced by cobalt or a cobalt ion. In still another alternative embodiment, the inducible promoter may be induced by bismuth or a bismuth ion.

In some embodiments, the promoter is induced by exposing a cell comprising the inducible promoter to a metal or metal ion. The cell may be exposed to the metal or metal ion by adding the metal to the bacterial growth media. In certain embodiments, the metal or metal ion added to the bacterial growth media may be efficiently recovered from the media. In other embodiments, the metal or metal ion remaining in the media after recovery does not substantially impede downstream processing of the media or of the bacterial gene products.

In a preferred embodiment, a cassette of the invention comprises an inducible promoter induced in the absence of $CO_2$, operably-linked to a nucleic acid encoding a thermostable lipase. In an exemplary embodiment, a cassette of the invention comprises a $P_{cmp}$ promoter (induced in the absence of $CO_2$) operably-linked to a nucleic acid encoding a thermostable lipase. The $P_{cmp}$ promoter is known in the art.

B. Second Promoter

Certain nucleic acid cassettes of the invention may comprise a second promoter. The second promoter may be an inducible promoter, or may be a constitutive promoter. If the second promoter is an inducible promoter, it may or may not be induced by the same compound or condition that induces the first inducible promoter. In one embodiment, the same compound or condition induces both the first and the second inducible promoters. In another embodiment, the first inducible promoter is induced by a different compound or condition than the second inducible promoter. Non-limiting examples of inducible promoters that may be used are detailed in section I(c)(ii)(A) above.

In certain embodiments, the second promoter is a constitutive promoter. Non-limiting examples of constitutive promoters may include constitutive promoters from Gram-negative bacteria or a bacteriophage propogating in a Gram-negative bacterium. For instance, promoters for genes encoding highly expressed Gram-negative gene products may be used, such as the promoter for Lpp, OmpA, rRNA, and ribosomal proteins. Alternatively, regulatable promoters may be used in a strain that lacks the regulatory protein for that promoter. For instance $P_{lac}$, $P_{tac}$, and $P_{trc}$ may be used as constitutive promoters in strains that lack LacI. Similarly, P22 $P_R$ and $P_L$ may be used in strains that lack the P22 C2 repressor protein, and $\lambda P_R$ and $P_L$ may be used in strains that lack the $\lambda C1$ repressor protein. In one embodiment, the constitutive promoter is from a bacteriophage. In another embodiment, the constitutive promoter is from a *Salmonella* bacteriophage. In yet another embodiment, the constitutive promoter is from a cyanophage. In some embodiments, the constitutive promoter is a *Synechocystis* promoter. For instance, the constitutive promoter may be the $P_{psbA11}$ promoter or its variant sequences, the $P_{rbc}$ promoter or its variant sequences, the $P_{cpc}$ promoter or its variant sequences, and the $P_{mpB}$ promoter or its variant sequences. In preferred embodiments, the second promoter is the $P_{trc}$ promoter.

In some embodiments, the nucleic acid cassette comprises a first inducible promoter and a second constitutive promoter operably-linked to a nucleic acid encoding a thermostable lipase. In a preferred embodiment, the nucleic acid cassette comprises a first inducible promoter induced in the absence of $CO_2$ and a second constitutive promoter, both operably-linked to a nucleic acid encoding a thermostable lipase. In an exemplary embodiment, the nucleic acid cassette comprises a first $P_{cmp}$ inducible promoter induced in the absence of $CO_2$ and a second $P_{trc}$ constitutive promoter, both operably-linked to a nucleic acid encoding a thermostable lipase.

iii. Additional Components

In certain embodiments, a nucleic acid cassette of the invention may further comprise additional components, such as a marker, a spacer domain, or a flanking sequence.

A. Markers

In one embodiment, a nucleic acid cassette of the invention comprises at least one marker. Generally speaking, a marker encodes a product that the host cell cannot make, such that the cell acquires resistance to a specific compound, is able to survive under specific conditions, or is otherwise differentiable from cells that do not carry the marker. Markers may be positive or negative markers. In some embodiments, a nucleic acid cassette of the invention may comprise both a positive marker and a negative marker. In certain embodiments, the marker may code for an antibiotic resistance factor. Suitable examples of antibiotic resistance markers may include, but are not limited to, those coding for proteins that impart resistance to kanamycin, spectromycin, streptomycin, neomycin, gentamicin (G418), ampicillin, tetracycline, and chloramphenicol. Additionally, the sacB gene may be used as a negative marker. The sacB gene is lethal in many bacteria when they are grown on sucrose media. Additionally, fluorescent proteins may be used as visually identifiable markers. Generally speaking, markers may be present during construction of the strains, but are typically removed from the final constructs. Proteins can also be marked by adding a sequence such as FLAG, HA, His tag, that can be recognized by a monoclonal antibody using immunological methods. In some embodiments, a marker may be a unique identifier of a genetically modified cyanobacterium. In other embodiments, a marker may be a unique identifier of a genetically modified chloroplast genome in a unicellular alga.

B. Spacer Domain

Additionally, a nucleic acid cassette of the invention may comprise a Shine-Dalgarno sequence, or a ribosome binding site (RBS). Generally speaking, a RBS is the nucleic acid sequence in the mRNA that binds to a 16s rRNA in the ribosome to initiate translation. For Gram-negative bacteria, the RBS is generally AGGA. The RBS may be located about 8 to about 11 bp 3' of the start codon of the first structural gene. One skilled in the art will realize that the RBS sequence or its distance to the start codon may be altered to increase or decrease translation efficiency.

C. Flanking Sequence

A cassette of the invention may also be flanked by a specific "flanking sequence." The phrase "flanking sequence" as used herein, refers to a nucleic acid sequence homologous to a chromosomal sequence. A vector comprising a flanking sequence on either side of a cassette (i.e., a left flanking sequence and a right flanking sequence) may homologously recombine with the homologous chromosome, thereby integrating the cassette between the flanking sequences into the chromosome. Generally speaking, flanking sequences may be of variable length. In an exemplary embodiment, the flanking sequences may be between about 300 and about 500 bp. In another exemplary embodiment, the left flanking sequence and the right flanking sequence are substantially the same length. For more details, see the Examples.

iv. Plasmids

A nucleic acid cassette of the invention may be part of a plasmid suitable for use in a bacterium. Such a plasmid may contain multiple cloning sites for ease in manipulating nucleic acid sequences. Numerous suitable plasmids are known in the art.

(d) Other Alterations to Facilitate Processing

A recombinant photosynthetic microorganism of the invention may comprise one or more alterations to further facilitate processing. For instance, a photosynthetic microorganism may express proteins that may be used to increase access to the cell wall to lyse the microorganism. Non limiting examples of proteins that may be used to increase access to the cell wall to lyse the microorganism may include an endolysin protein or a holin protein. Endolysins are peptidoglycan-degrading enzymes that attack the covalent linkages of the peptidoglycans that maintain the integrity of the cell wall. For instance, the endolysin gp19 from *Salmonella* phage P22 is able to degrade the 6803 polypeptidoglycan layers, and the endolysin R from *E. coli* phage A is able to compromise the polypeptidoglycan layers of the microorganism. These sequences may be expressed with different promoters with variant low transcription efficiencies to limit adverse growth effects. Holins are small membrane proteins used by bacteriophages for lysing hosts by permeabilizing host membranes. Non limiting examples of holin proteins that may be expressed in the recombinant photosynthetic microorganism of the invention to facilitate processing may include a holin from a bacteriophage that infects *Synechocystis*, from a bacteriophage that infects *Salmonella*, from a P22 phage such as the protein encoded by gene 13 of the P22 phage, from a λ phage such as the protein encoded by gene S of the λ phage, from an *E. coli* phage such as the protein encoded by gene E of *E. coli* phage PhiX174. Algal chloroplasts do not comprise a peptidoglycan-containing cell wall. As such, synthesis of endolysins encoded by the chloroplast genome would be without effect, and synthesis of holins may be sufficient to permeabilize and lyse the algal chloroplast membrane.

The endolysin or the holin proteins may be as described above with at least one, or a combination of one or more, nucleic acid deletions, substitutions, additions, or insertions which result in an alteration in the corresponding amino acid sequence of the encoded endolysin or holin protein, such as a homolog, ortholog, mimic or degenerative variant. Such an endolysin or holin may be generated using recombinant techniques such as site-directed mutagenesis (Smith Annu. Rev. Genet. 19. 423 (1985), e.g., using nucleic acid amplification techniques such as PCR (Zhao et al. Methods Enzymol. 217, 218 (1993) to introduce deletions, insertions and point mutations. Other methods for deletion mutagenesis involve, for example, the use of either BAL 31 nuclease, which progressively shortens a double-stranded DNA fragment from both the 5' and 3' ends, or exonuclease III, which digests the target DNA from the 3' end (see, e.g., Henikoff Gene 28, 351 (1984). The extent of digestion in both cases is controlled by incubation time or the temperature of the reaction or both. Point mutations can be introduced by treatment with mutagens, such as sodium bisulfite (Botstein et al. Science 229, 1193 (1985). Other exemplary methods for introducing point mutations involve enzymatic incorporation of nucleotide analogs or misincorporation of normal nucleotides or alpha-thionucleotide by DNA polymerases (Shortle et al. Proc. Natl. Acad. Sci. USA 79, 1588 (1982). PCR-based mutagenesis methods (or other mutagenesis methods based on nucleic acid amplification techniques), are generally preferred as they are simple and more rapid than classical techniques (Higuchi et al. Nucleic Acids Res. 16, 7351 (1988); Vallette et al. Nucleic Acids Res. 17, 723 (1989).

(e) Alterations to Increase Fatty Acid Secretion.

A recombinant photosynthetic microorganism of the invention may further comprise alterations to enable and/or increase fatty acid secretion. In one embodiment, a polar cell layer of the microorganism may be altered so as to increase fatty acid secretion. By way of example, the peptidoglycan layer, the outer membrane layer, and/or the S layer of a photosynthetic microorganism may be altered to enable increased fatty acid secretion. For instance, the expression of a nucleic acid encoding an S-layer protein, such as sll1951, may be decreased or eliminated. In one embodiment, the photosynthetic microorganism is a cyanobacterium, and the photosynthetic microorganism may comprise the mutation Δsll1951.

In another embodiment, the polypeptidogly can layer of a photosynthetic microorganism may be weakened to enable increased fatty acid secretion. Methods of weakening the polypeptidoglycan layer may include administering an antibiotic, such as ampicillin, to the bacterium. Care should be taken, however, to balance the ability to secrete fatty acids with the potential for cell lysis.

Another method to weaken the peptidoglycan layer may comprise down-regulating the transcription efficiency of nucleic acids encoding protein involved in peptidoglycan synthesis, such as those in the mur (e.g., slr0017, slr1423, slr1656 and sll2010) and ldh (e.g., slr0528 and slr1656) families to weaken the polypeptidoglycan layer structures. In another embodiment, a nucleic acid encoding a penicillin-binding protein such as ftsI (sll1833), mrcB (slr1710) and ponA (sll0002) may be deleted or modified. These proteins are required for the assembly of the peptidoglycan.

Yet another method to interfere with peptidoglycan synthesis is by substituting a nucleic acid for a central step in an essential pathway with one from a bacterial species, such as using an exogenous dap or alr gene. Still yet another way to weaken the polypeptidoglycan layer is to introduce one or more nucleic acid sequences encoding an endolysin from a bacteriophage. Such a nucleic acid sequence may then be expressed at low levels.

Yet another method to increase fatty acid secretion is to express or overexpress a nucleic acid sequence encoding a transporter or porin to make channels for the lipid. Many transport and efflux proteins serve to excrete a large variety of compounds, and these can possibly be modified to be selective for fatty acids. For example, *E. coli* outer membrane protein FadL is a membrane-bound fatty acid transporter, which binds long chain fatty acid with a high affinity. Other suitable transport proteins may include efflux proteins and fatty acid transporter proteins (FATP).

(f) Biofuel and Biofuel Precursor Production

The invention may be used to release any product of value synthesized in the photosynthetic microorganism. Non-limiting examples of products that may be synthesized in photosynthetic microorganism may include biofuels and biofuel precursors, hydrogen gas and biodegradable plastics such as polyhydroxybutyrate (PHB). In preferred embodiments, the products may be biofuels and biofuel precursors. Non limiting examples of biofuels and biofuel precursors that may be produced in the photosynthetic microorganism may be free fatty acids, neutral lipids, and alkanes. Methods of producing or overproducing biofuels and biofuel precursors are described below.

i. Alterations to Increase Fatty Acid Generation

A recombinant photosynthetic microorganism of the invention may comprise one or more alterations to increase fatty acid generation. For instance, a photosynthetic microorganism may comprise an alteration that enables the synthesis of an acyl-ACP thioesterase, that inhibits fatty acid degradation, that channels resources into fatty acid synthesis, that down-regulates or eliminates competing pathways, that decreases repression or feedback inhibition, and that maintains stationary phase fatty acid production. Each of these alterations are described in more detail below.

A. Acyl-ACP Thioesterase

A photosynthetic microorganism of the invention may comprise an alteration that enables the synthesis of at least one acyl-ACP thioesterase (TE). Methods of altering a microorganism to synthesize a TE are known in the art. For instance, a microorganism may be altered to express a nucleic acid encoding a TE. Such a nucleic acid may be operably linked to a regulated promoter or a constitutive promoter. In certain embodiments, a microorganism may synthesize one, two, three, four or five TEs. A nucleic acid encoding a TE may be chromosomally integrated, or may be expressed on an extrachromosomal vector. Suitable vectors are known in the art. Similarly, methods of chromosomally inserting a nucleic acid are known in the art.

In some embodiments, a microorganism may synthesize a TE that is restricted to the cytosol of the microorganism. For instance, in one embodiment, a microorganism of the invention may synthesize a variant of TesA that is restricted to the cytosol of the microorganism. By way of non-limiting example, a microorganism may synthesize *TesA. The expression of a nucleic acid encoding TesA may be regulated or constitutive. For instance, the nucleic acid may be operably linked to an inducible promoter. Non-limiting examples of a suitable inducible promoters may include $P_{nrsB}$, $P_{cmpA}$, $P_{isiA}$, $P_{sigE}$, $P_{lrtA}$, or $P_{sbD2}$. $P_{nrsB}$ is nickel inducible, $P_{cmpA}$ is inducible by $CO_2$ limitation, $P_{isiA}$ is inducible under low Fe conditions, $P_{sigE}$ is inducible during the stationary phase, $P_{lrtA}$ is dark inducible, and $P_{sbD2}$ may be induced by strong light.

Alternatively, the nucleic acid encoding a TE may be operably linked to a constitutive promoter, such as $P_{psbA2}$, $P_{cpc}$, $P_{rbc}$, $P_{petB}$, $P_{psaAB}$, $P_{hspA}$, or $P_{sigA}$.

Other TE enzymes are known in the art and may be used in the present invention. For instance, a TE from *Cinnamomum camphorum*, *Umbellularia californica*, or *Cuphea hookeriana* may be used. In another embodiment, a TE outlined in WO 2009/076559 may be used.

The selection of the TE may be determined by the desired chain length of the resulting free fatty acid. In one embodiment, a TE with a preference for shorter free fatty acids may be used. For instance, a TE with a preference for C16, C14, C12, C10 or C8 fatty acids may be used.

A nucleic acid encoding a TE may be modified for high-level expression in a photosynthetic microorganism of the invention. As used herein, "modified" refers to an alteration of a nucleic acid sequence that results in a change in the level of transcription of a nucleic acid sequence, or that results in a change in the level of synthesis of encoded protein. For instance, in one embodiment, modify may refer to altering the start codon of a nucleic acid sequence. Generally speaking, a GTG or TTG start codon, as opposed to an ATG start codon, may decrease translation efficiency ten-fold. In another embodiment, modify may refer to altering the Shine-Dalgarno (SD) sequence of a nucleic acid sequence. The SD sequence is a ribosomal binding site (RBS) generally located 6-7 nucleotides upstream of the start codon. The SD/RBS consensus sequence is AGGAGG, and variations of the consensus sequence may alter translation efficiency. In yet another embodiment, modify may refer to altering the distance between the SD sequence and the start codon. In still another embodiment, modify may refer to altering the −35 sequence for RNA polymerase recognition. In a similar embodiment, modify may refer to altering the −10 sequence for RNA polymerase binding. In an additional embodiment, modify may refer to altering the number of nucleotides between the −35 and −10 sequences. In an alternative embodiment, modify may refer to optimizing the codons of the nucleic acid sequence to alter the level of translation of the mRNA. For instance, non-A rich codons initially after the start codon of a nucleic acid sequence may not maximize translation of the corresponding mRNA. Similarly, the codons of the nucleic acid sequence may be altered so as to mimic the codons in genes encoding highly synthesized proteins of a particular organism. In a further embodiment, modify may refer to altering the GC content of the nucleic acid sequence to change the level of translation of the corresponding mRNA. Additionally, modify may refer to alterations in the DNA sequence of a gene so that the transcribed mRNA is stabilized with a reduced rate of degradation but still able to specify a protein of the original amino acid sequence. In still another embodiment, a nucleic acid may be optimized by altering the nucleic acid such that the ability of the encoded protein to form efficient enzyme complexes is affected.

Methods of altering a nucleic acid as described above are known in the art.

B. Inhibiting Fatty Acid Degradation

A recombinant photosynthetic microorganism of the invention may comprise an alteration that inhibits fatty acid degradation. For instance, the acyl-ACP synthetase (AAS) nucleic acid may be modified to decrease or eliminate expression of the nucleic acid. As described below the aas gene used to be referred to as the fadD gene. In one embodiment, aas (slr1609) is modified by replacing the aas chromosomal sequence with another sequence, such as a nucleic acid encoding a TE.

C. Alterations that Channel Resources into Fatty Acid Synthesis

In some embodiments, a recombinant photosynthetic microorganism of the invention may comprise one or more alterations that channel resources into fatty acid synthesis. In certain embodiments, this may mean decreasing or eliminating expression of a nucleic acid that is not necessary for fatty acid synthesis. For instance, a photosynthetic microorganism may comprise a mutation that decreases or eliminates expression of a nucleic acid encoding a polyhydroxyalkanoate (PHA) synthesis enzyme. Non-limiting examples may include slr1993 and slr1994. In another embodiment, a microorganism may comprise a mutation that alters synthesis of an S-layer protein. Non-limiting examples may include mutations in sll1951, such as Δsll1951. In each of the above embodiments, the mutations should not alter the fitness of the microorganism in such a way as to reduce fatty acid synthesis.

Another way to channel resources into fatty acid synthesis is to increase the expression level of nucleic acid sequences encoding proteins in the primary free fatty acid production pathway. For instance, the expression of a nucleic acid encoding a protein involved in the generation of pyruvate may be increased. By way of non-limiting example, the expression of sll0587 or sll1275 may be increased. In another embodiment, the expression of a nucleic acid encoding a protein involved in the synthesis of acetyl-CoA from pyruvate, such as pdh or odh may be increased. In yet another embodiment, a nucleic acid sequence encoding a protein involved in the synthesis of malonyl-CoA from acetyl-CoA may be altered, such as accB-CDA. Alternatively, a photosynthetic microorganism may be altered such that ACC may be overproduced by introducing a synthetic operon. Typically, the transcripts of the nucleic acids encoding the ACC subunits should be produced in relatively equal molar ratios. Non-limiting examples may include altering the photosynthetic microorganism to include the operon $P_{cpc}$ accB accC $P_{rbc}$ accD accA. In still another embodiment, the expression of a nucleic acid sequence encoding a protein involved in the synthesis of fatty acyl-ACP may be increased. For instance, the expression of a fab nucleic acid sequence may be increased (e.g. fabD, fabF, fabG, fabZ and fabl). In an alternative embodiment, the expression of a nucleic acid encoding an acyl carrier protein (such as ssl2084) may be increased. In a further embodiment, the expression of pyk may be increased.

Yet another way to channel resources into fatty acid synthesis is to optimize expression of a nucleic acid encoding a protein involved in fatty acid synthesis. For instance, the expression may be optimized as described above. Alternatively, the expression may be optimized by altering the nucleic acid sequence to increase mRNA stability. For instance, the sequence may be altered to remove stem-loop structures.

D. Alterations to Competing Pathways

A photosynthetic microorganism of the invention may be altered to reduce or eliminate the expression of a nucleic acid sequence encoding a protein that competes with fatty acid synthesis for reactants. By way of non-limiting example, the expression of slr1176 for the glycogen synthesis pathway; slr0301 (pps) for the phosphoenolpyruvate pathway; slr1192 for the predicted alcohol synthesis pathway; slr0089 and slr0090 for the vitamin E pathway; sll0920 for the oxaloacetate pathway; sll0891 for the malate synthesis pathway; sll1564 for the leucine synthesis pathway, sll0401 for the citrate pathways, and slr2132, sll1299, sll0542, slr0091 and sll0090 for the acetate pathways may be reduced or eliminated. Similarly, the expression of a nucleic acid sequence encoding a cyanophycin synthetase (such as s/r2002 or s/r2001) can be reduced or eliminated.

Expression of the above nucleic acid sequences may be reduced by altering the promoter, SD sequence, and/or start codon, etc. as described above.

E. Alterations that Decrease Repression or Feedback Inhibition

A photosynthetic microorganism of the invention may be altered to decrease repression of fatty acid synthesis or to decrease feedback inhibition of fatty acid synthesis. For instance, expression of a TE, as described above, may be used to decrease inhibition of ACC, FabH, and Fabl. Similarly, repression may be decreased by altering the promoters of nucleic acids encoding proteins involved in fatty acid synthesis so that they do not include the binding sequences for repressors.

F. Alterations to Maintain Stationary Phase Fatty Acid Production

A recombinant photosynthetic microorganism of the invention may be altered so as to allow secretion of fatty acids during stationary growth phase. Generally speaking, such alterations may include supplying a bacterium with a nucleic acid sequence encoding a protein involved in fatty acid synthesis, wherein the nucleic acid is operably linked to a promoter with increased activity in the stationary phase.

G. Fatty Acid Acyl Chain Structure Modification

A recombinant photosynthetic microorganism of the invention may be altered so as to modify the structure of the fatty acids produced. For instance, the chain length, the chain saturation, and the branching of the fatty acid may be modified. In certain embodiments, chain length may be altered by the choice of TE, as detailed above and in the examples. Furthermore, the expression of a TE may alter chain saturation.

A microorganism of the invention may be altered to produce branch chain fatty acids. Typically, such a bacterium will express one or more nucleic acid sequences encoding a protein involved in the production of branch chain fatty acids, such as a branched-chain amino acid aminotransferase, a branched-chain α-keto acid dehydrogenase complex, β-ketoacyl-ACP synthase III, acyl carrier protein, and β-ketoacyl-ACP synthase II.

ii. Alterations to Produce Neutral Lipids

A recombinant photosynthetic microorganism of the invention may comprise one or more alterations to produce neutral lipids. As used herein, the phrase "neutral lipids" refers to non-polar lipids. Non-limiting examples of neutral lipids may include triacylglycerol (TAG), steryl esters (SEs), wax ester (WE), fatty acyl methyl ester (FAME), fatty acyl ethyl ester (FAEE) and poly(3-hydroxybutyrate) (PHB). Generally speaking, neutral lipids lack charged groups and are therefore unable to integrate into bilayer membranes in substantial amounts. They serve as intracellular storage molecules for sterols, free fatty acids, and diacylglycerols (DAGs).

A photosynthetic microorganism capable of producing neutral lipids may comprise a nucleic acid sequence encoding a neutral lipid synthase. Generally speaking, a neutral lipid synthase is a synthase that aids in the expression of one or more neutral lipids. Neutral lipid synthases may be found in other prokaryotic or eukaryotic species. For instance, the first wax ester synthase (WS) as well as acyl-CoA:diacylglycerol acyltransferase (DGAT) (WS/DGAT) enzyme was identified in *A. baylyi* sp. ADP1, and its gene (atfA) was cloned into *E. coli* by Kalscheuer and Steinbüchel (2003 J. Biol. Chem. 287: 8075-82). This bacterium possesses only a single WS/DGAT enzyme. Numerous atfA homologs, however, may be found among the available genome databases of actinomycetes, especially in those of *Mycobacterium, Rhodococcus* and *Streptomycetes*. In particular, Mycobacteria possess a large number of conserved proteins with high homologies to the *A. baylyi* sp. ADP1 AtfA. By way of non-limiting example, 15 atfA homologous nucleic acid sequences were identified and characterized in *M. tuberculosis* H37Rv. Nucleic acid sequences with high homologies to the *Acinetobacter* sp. ADP1 atfA were also identified in the genome databases of several Gram-negative strains, including marine bacteria like *Hahella chejuensis*, psychrophilic strains like *Psychrobacter* sp. and *Polaromonas* sp. and even in *Bradyrhizobium japonicum*. Hence, suitable neutral lipid synthases may be derived, for example, from *Acinebacter baylyi, Rhodococcus opacus, Rhodococcus ruber, Ralstonia eutropha, Streptomyces coelicolor, Norcardia* sp., or *Mycobacterium smegmatis*. In one embodiment, the TAG synthase encoded by the atfA gene from *Acinebacter baylyi* is a non-limiting example of a neutral lipid synthase. Alternatively, suitable neutral lipid synthases may be synthesized in vitro based on a wild-type sequence derived from a prokaryotic or eukaryotic organism.

A photosynthetic microorganism capable of producing neutral lipids may also comprise a nucleic acid sequence encoding a lipid body protein. Typically a lipid body protein aids in storing the neutral lipids within the photosynthetic microorganism. A non-limiting example of a lipid body protein is a PHA inclusion protein such as PhaC, PhaZ, PhaR, and phasins such as PhaP1. Additionally, proteins associated with TAG inclusions have been referred to as granule-associated proteins (GAP) and exhibit apparent molecular masses ranging from 15 to 31 kDa. By way of non-limiting example, in *R. opacus* PD630, these were GAP15, GAP17, GAP20, GAP26, and GAP31, with the numeration indicating the apparent molecular weight (Kalscheuer et al. 2001 Arch. Microbiol. 177:20-28). The nucleic acid encoding PhaP1 may be cloned from *Ralstonia eutropha*.

The critical substrate for neutral lipids synthesis is acyl-CoA. The *A. baylyi* sp. ADP1 WS/DGAT is able to transfer acyl-CoA to diacylglycerol to produce TAG, and also able to transfer acyl-CoA to methanol or ethanol to produce FAME or FAEE respectively. In some instances, a photosynthetic microorganism does not produce a significant amount of acyl-CoA in the cell for the production of neutral lipids. For instance, cyanobacteria do not possess the acyl-CoA synthesis pathway, and thus do not have a significant amount of acyl-CoA in the cell for the production of neutral lipids. In contrast, cyanobacteria normally use acyl carrier proteins (ACP) as the intermediate acyl carriers for fatty acid synthesis and metabolism. Thus, the photosynthetic microorganism may be modified to overproduce acyl CoA.

Methods of overproducing acyl CoA in a photosynthetic microorganism can and will vary depending on the pathways that lead to synthesizing acetyl CoA microorganism or the pathways that sequester acetyl CoA in the microorganism. For instance, to overproduce acyl-CoA in cyanobacteria, free fatty acids have to be released from acyl-ACP by thioesterases. Thioesterases may be from bacteria and plants, e.g., tesA gene and its variants, and fatB genes and their variants. Then the free fatty acids have to be ligated to Coenzyme A by acyl-CoA ligases (ACL). ACL genes may be from bacteria (e.g., fadD from *E. coli*), and from yeast (e.g., faa2 from *Saccharomyces cerevisiae*). Acyl-CoA is the right substrate to produce an acyltransferase (e.g., WS/DGAT) to trans-esterify with an alcohol for a neutral lipid such as triaclyglycerols (TAG), fatty acyl methyl esters (FAME), or fatty acyl ethyl esters (FAEE).

iii. Alterations to Produce Alkanes

A recombinant photosynthetic microorganism of the invention may comprise one or more alterations to produce alkanes. As used herein, the term "alkanes" refers to linear or branched compounds that consist only of hydrogen and carbon atoms attached exclusively by saturated bonds. Alkanes are major constituents of gasoline, diesel, and jet fuel.

Alkanes are naturally produced by a diversity of microorganisms such as various strains of cyanobacteria. In essence, an acyl-acyl carrier protein reductase and an aldehyde decarbonylase together convert intermediates of fatty acid metabolism to alkanes and alkenes. A photosynthetic microorganism capable of producing alkanes may comprise a nucleic acid sequence encoding an alkane biosynthesis enzyme. Methods of construction of a photosynthetic microorganism capable of producing alkanes and methods of production of alkanes in a photosynthetic microorganism are as described in the examples below.

The photosynthetic microorganism capable of producing alkanes may produce linear or branched alkanes comprising 1 or more carbon atoms. In some embodiments, the alkanes may comprise 1, 2, 3, 4, 5, 6, 7, 8, 9, 10, 11, 12, 13, 14, 15, 16, 17, 18, 19, 20, 21, 22, 23, 24, 25, or more carbon atoms. In other embodiments, the alkanes may comprise 1, 2, 3, 4, 5, 6, 7, 8, 9, or 10 carbon atoms. In yet other embodiments, the alkanes may comprise 9, 10, 11, 12, 13, 14, 15, 16, 17, 18, 19, or 20 carbon atoms. In preferred embodiments, the alkanes may comprise 13, 14, 15, 16, or 17-carbon atoms.

(g) Biological Containment

Under certain embodiments, a live recombinant bacterium may possess the potential to survive and multiply if accidentally released into the environment. A bacterium of the invention may be altered to result in death of the altered bacterium upon accidental release into the environment. Consequently, in certain embodiments, a recombinant bacterium of the invention may comprise one or more mutations that decrease, if not preclude, the ability of the bacterium to persist in the environment. Non-limiting examples of mutations that may decrease, if not preclude, the ability of the bacterium to persist in the environment may include auxotrophic mutations that render a recombinant bacterium dependent on a nutrient or compound added to the culture medium, but is not found in the environment, mutations that produce lysis of the recombinant bacterium upon release into the environment, or combinations thereof. In one embodiment, a recombinant bacterium of the invention may comprise auxotrophic mutations that render a recombinant bacterium dependent on a nutrient or compound added to the culture medium. In another embodiment, a recombinant bacterium of the invention may comprise mutations that produce lysis of the recombinant bacterium upon release into the environment.

In a preferred embodiment, a biological containment system may comprise two recombinant bacteria with the first being unable to synthesize at least one essential unique cell constituent and the second also being unable to synthesize at least one essential unique constituent but different from that required by the first strain with the first and second strains being able to produce and secrete the precursors of the cell constituents required by the second and first strain, respectively, such that the two strains are totally dependent on each other with lethality of both strains by lysis occurring when the cultures are diluted to lower cell densities. For instance, a first recombinant bacterium comprising a mutation in the dapA or dapB gene and therefore requiring the peptidoglycan precursor DAP, and a second recombinant bacterium comprising a mutation in the alr gene and therefore requiring the peptidoglycan precursor D-alanine may be generated. Such strains may be completely dependent upon each other for synthesis of peptidoglycan and will result in lysis when one or the other recombinant bacterium is not present, or is present at low cell densities.

In an exemplary embodiment, a biological containment system comprises a first recombinant bacterium comprising a mutation in a dap gene, and a second recombinant bacterium comprising a mutation in the alr gene.

II. Method of Releasing Biofuels and Biofuel Precursors

Another aspect of the present invention is a method for releasing biofuels and biofuel precursors. The biofuels and biofuel precursors may be as described in Section I above. Generally speaking, a method of the invention comprises introducing into a photosynthetic microorganism a nucleic acid cassette comprising an inducible promoter operably-linked to a nucleic acid encoding a thermostable lipase capable of hydrolyzing the lipid membranes of the microorganism. Methods of introducing a nucleic acid cassette comprising an inducible promoter operably-linked to a nucleic acid encoding a thermostable lipase into a microorganism are described in Section I above. A method of the invention further comprises culturing the microorganism comprising the inducible promoter operably-linked to a nucleic acid encoding a thermostable lipase. Methods of culturing a photosynthetic microorganism are known in the art and detailed in the examples.

A method of the invention further comprises inducing the promoter to cause expression and subsequent synthesis of the thermostable lipase. According to the invention, in some embodiments the culture comprising the microorganism may then be concentrated. Concentrating the culture comprising the microorganism significantly reduces the biomass volume to be processed, resulting in reducing the need for space, time, equipment, reagents and energy to extract biofuels and biofuel precursors from the biomass.

A method of the invention also comprises activation of the thermostable lipase. The thermostable lipase may be activated by increasing the incubation temperature of the culture to a temperature capable of activating the thermostable lipase.

In some embodiments, when the inducible promoter is induced in the absence of $CO_2$, the promoter may be induced by confining the culture comprising the photosynthetic microorganism in sealed vessels for $CO_2$ limitation. The duration of $CO_2$ limitation can and will vary depending on the culture conditions, the strain of the microorganism and other variables, and may be determined by experimentation as described in the Examples below. In some embodiments, the promoter may be induced in the absence of $CO_2$ for about 6, 12, 24, 36, or 48 hours. In other embodiments, the promoter may be induced in the absence of $CO_2$ for about 1, 2, 3, 4, 5, 6, 7, 8, 9, or 10 days. In preferred embodiments, the promoter may be induced in the absence of $CO_2$ for about 1 day.

Methods of concentrating cultures comprising a photosynthetic microorganism are known in the art and may include centrifugation or filtration of the culture. In some embodiments, the culture comprising a photosynthetic microorganism may be concentrated to a density of about $10^9$, $10^{10}$, $10^{11}$, or $10^{12}$ cells/mL. In preferred embodiments, the culture of photosynthetic microorganisms may be concentrated to a density of about $10^{11}$ cells/mL.

Temperatures that may be used to activate the thermostable lipase are as described in Section I(b) above. In preferred embodiments, the thermostable lipase may be activated by incubating the photosynthetic microorganism of the invention at about 46° C.

Biofuels and biofuel precursors produced by the photosynthetic microorganism may be extracted from the culture media or culture biomass. Methods of extracting the fatty acids from photosynthetic microorganism cultures are known in the art and detailed in the Examples. For instance, a fatty acids biofuel may be pipetted, filtered, and/or skimmed from the culture media. In addition, the culture media may be treated to extract any remaining fatty acids dissolved in the media. Briefly, the media may be acidified and extracted with an organic solvent, such as hexane. The organic phase may then be separated and dried to give the fatty acids. In some embodiments, the media is extracted more than once with the organic solvent. For instance, the media may be extracted two, three, four or five times. Such treatment is described in the Examples.

DEFINITIONS

The term "cell wall", as used herein, refers to the peptidoglycan layer of the cell wall of a cyanobacterium, or the cell wall of algal cells comprising polysaccharides and glycoproteins. Stated another way, "cell wall" as used herein refers to the rigid layer of the cell wall.

The term "operably-linked", as used herein, means that expression of a gene is under the control of a promoter with which it is spatially connected. A promoter may be positioned 5' (upstream) of a gene under its control. The distance between the promoter and a gene may be approximately the same as the distance between that promoter and the gene it controls in the gene from which the promoter is derived. As is known in the art, variation in this distance may be accommodated without loss of promoter function.

The term "promoter", as used herein, may mean a synthetic or naturally-derived molecule which is capable of conferring, activating or enhancing expression of a nucleic acid in a cell. A promoter may comprise one or more specific transcriptional regulatory sequences to further enhance expression and/or to alter the spatial expression and/or temporal expression of same. A promoter may also comprise distal enhancer or repressor elements, which can be located as much as several thousand base pairs from the start site of transcription. In some embodiments, activators may bind to promoters 5' of the −35 RNA polymerase recognition sequence, and repressors may bind 3' to the −10 ribosome binding sequence.

EXAMPLES

The following examples illustrate various iterations of the invention.

Introduction for Examples 1-4

Renewable and carbon neutral biofuels produced by photosynthetic cyanobacteria and unicellular algae are promising alternatives to petroleum based fuels (12). The traditional downstream recovery of microalgal or cyanobacterial lipids accounts for 70-80% of the total cost of biofuel production, which involves harvesting the cells, cell digestion, and solvent extraction (11). To bypass these steps, a Green Recovery process (GR hereafter) was developed by using $CO_2$ limitation inducible promoters to control the synthesis of lipases to degrade the cyanobacterial membranes and release free fatty acids (FFA hereafter) (8). However, GR requires light to induce lysis of cells with release of FFA, since energy from photosynthesis is required for gene expression and lipase synthesis in GR (8). Due to self-shading, GR efficiency is low for condensed biomass (above 10" cells/ml), so GR is usually applied in unconcentrated cultures (i.e., normal growth conditions). In a recent continuous semi-batch experiment with a GR strain SD237 at 4-liter scale for 20 days (details discussed below), 2 l hexane was used to extract a 20 l GR lysate and recovered about 0.7 g FFA.

In order to reduce the liquid volume to be handled in GR as originally described, which requires $CO_2$ limitation in the presence of light and extraction by solvent, improvements are planned for GR with light-independence, so that the biomass can be concentrated to about 0.3% of the culture volume to enable using much less solvent for extraction. As biosynthesis is limited in the dark for phototrophs, it was decided to synthesize thermostable lipases with cultures grown at ambient temperatures before biomass concentration, and then elevate the temperature of the cell concentrates to increase lipase activities to commence digestion of membrane lipids to release FFAs. Genes encoding thermostable lipases are widely distributed in nature among thermophilic microorganisms living in various areas in relation to high temperature with oil contamination or oil discharge (5). Thermostable lipases are expected to play significant roles in industrial processing because running bioprocesses at elevated temperatures leads to higher conversion rates, increase the solubility and diffusion rates of lipids, and reduce the risk of contamination with environmental heterotrophs (3). The enzyme activity of thermostable lipases increases with temperature, reaches a maximum at the optimal temperature, and then drops above the optimal temperature due to protein denaturation (2, 5, 19). Thus, a heat-inducible self-digestion process (referred to as thermorecovery hereafter) was designed to eliminate light-dependence by synthesizing thermostable lipases at low temperature and activating them at higher temperatures.

Materials and Methods for Examples 1-4

Bacterial Strain Construction, Media, and Growth Conditions.

All SD strains are derived from *Synechocystis* sp. PCC6803 strain SD100 (7). Genes are inserted into SD strains by double-crossover recombination with a $Km^R$ cassette (9). Synthesized genes and related DNA sequences are listed in Table 1. The genes are designed by back translation from protein sequences with Gene Designer 2.0 (DNA 2.0). The primers for constructions are listed in Table 2. SD strains were grown at 27° C. in BG-11 medium under continuous illumination (140 μmol photons $m^{-2} s^{-1}$) and bubbled with air (7). The details for preservation of SD cells and growing an SD culture from a colony were previously described (9). The cell membrane damage was detected by staining with 5 μM SYTOX Green nucleic acid stain (7).

TABLE 1

Synthesized Lipase Genes and Other DNA Sequences gtl (SEQ ID NO: 30)
ATGAAATGCTGTCGGATTATGTTTGTGTTGTTAGGTCTGTGGTTCGTGTTCGG
CTTATCTGTCCCTGGTGGGCGCACTGAAGCGGCGTCCTTACGCGCCAATGAT
GCTCCGATTGTGTTACTCCATGGGTTTACCGGTTGGGGTCGTGAGGAAATGT
TTGGTTTCAAGTATTGGGGCGGCGTGCGCGGCGATATCGAACAATGGCTGAA
CGACAACGGTTATCGTACTTATACTCTGGCGGTCGGTCCGCTCTCTAGCAACT
GGGACCGGGCGTGTGAAGCGTATGCTCAGTTAGTCGGCGGGACTGTCGATT
ATGGGGCTGCCCATGCGGCTAAGCACGGCCATGCGCGGTTTGGCCGCACTT
ATCCCGGCCTGTTGCCGGAATTGAAACGTGGTGGCCGCATCCATATCATCGC
CCACAGCCAAGGGGGGCAGACTGCCCGCATGTTAGTCTCTCTCTTAGAGAAC
GGTAGCCAAGAAGAGCGGGAGTACGCCAAGGCGCATAACGTGTCTTTGTCTC
CGTTGTTTGAAGGTGGTCATCATTTTGTGTTGAGTGTGACTACCATCGCCACT
CCTCATGACGGGACTACTTTAGTCAACATGGTTGATTTCACCGATCGCTTTTTT
GACTTGCAAAAAGCGGTGTTGGAAGCGGCGGCTGTCGCCAGCAACGTGCCG
TACACTAGTCAAGTATACGATTTTAAGCTCGACCAATGGGGTCTGCGCCGCCA
GCCGGGTGAATCTTTCGACCATTATTTTGAACGGCTCAAGCGCTCCCTGTTT
GGACTTCCACTGATACCGCCCGCTACGATTTATCCGTTTCCGGTGCTGAGAA
GTTGAATCAATGGGTGCAAGCTAGCCCGAATACTTATTATTTGAGTTTCTCTAC
TGAACGGACTTATCGCGGTGCGCTCACTGGCAACCATTATCCCGAACTCGGT
ATGAATGCTTTCAGCGCGGTCGTATGCGCTCCGTTTCTCGGTTCTTACCGCAA
TCCGACTCTCGGCATTGACGACCGTTGGT tll (SEQ ID NO: 31)
ATGCGTAGCTCCTTAGTGCTGTTCTTCCTCTCTGCTTGGACTGCCTTGGCTCG
GCCTGTTCGTCGTGCTGTTCCTCAAGATCTGCTCGACCAGTTTGAACTCTTTT
CTCAATATTCTGCTGCCGCTTACTGTGCTGCTAACAATCATGCTCCTGTGGGC
TCTGACGTAACTTGCTCTGAGAATGTCTGCCCTGAGGTAGATGCTGCTGACG
CTACTTTTCTCTATTCTTTTGAAGATTCTGGTTTAGGCGATGTTACCGGCTTAC
TCGCTCTCGACAACACTAATAAACTGATCGTCCTCTCTTTCCGCGGCTCTCGT
TCTGTAGAGAACTGGATCGCTAACCTCGCCGCCGACCTGACTGAAATTTCTG
ACATCTGCTCCGGCTGCGAGGGGCATGTCGGCTTCGTTACTTCTTGGCGTTC
TGTAGCCGACACTATTCGTGAGCAGGTGCAGAATGCCGTGAACGAGCATCCC
GATTACCGCGTGGTCTTTACCGGTCATAGCTTGGGTGGCGCTCTGGCTACTA
TTGCCGCTGCTGCTCTGCGTGGTAATGGTTACAATATCGACGTGTTCTCTTAT
GGCGCTCCCCGCGTCGGTAACCGTGCTTTTGCTGAATTCCTGACCGCTCAGA
CTGGCGGCACCCTGTATCGCATCACCCATACCAATGATATCGTCCCTCGTCT
CCCTCCTCGTGACTGGGGTTACAGCCACTCTAGCCCTGAGTACTGGGTCACT
TCTGGTAACGACGTCCCTGTGACCGCTAACGACATCACCGTCGTGGAGGGCA
TCGATTCCACCGACGGGAACAACCAGGGGAATATCCCTGACATCCCTTCTCA
TTTATGGTATTTCGGTCCCATTTCTGAGTGTGATTAA sll (SEQ ID NO: 32)
ATGCCCATGAAAATTAATCGTTACGCTATTGGTTCTGCCGCCTTAGCTGCCGG
TTTATTAATGTCCTCTGCCGCTTTCGCCGTTAATCCTGGTGGTGGTGGTTCTG
GTTTCGCCTCCTTATACAACCGTGCCGAATCTGACGGTCGTTGCTCTGTTACC
CGTTTAAACGTGGGTTCTTCTACCTTCTACATCCCTCGTGACCCCTCTAACCC
CAACGCCCGTTTCAACGTGTTAGTGTGGGTAATGGTACCGGTGGTAACTCC
TTAACCTATGCTACTTTATTAGAATCTGTTGCCAGTCACTGCATCGCTGTAGCC
GCTGCCAACACCGCCAACTCCGGTACCGGTGTGGAAATGCAGGAAGCTTACA
ACTCTTTACGTTCCCGTTATGGTAACATCTTAGGTTCCAAAGTGTGCACTGCC TABLE 1-continued Synthesized Lipase Genes and Other DNA Sequences

```
GGTCACTCTCAGGGTGGTGGTGGTTCCTTCAACGCCGCCAACCGTATCGGTG
CCAACTGCGTGATCCCTGTGCAGCCTGATACCCGTTTCACCACTCGGATCTA
CTCTCCTTTAGCTTCTCATGTGGAAGTGATCACCTTATGGGGTCAGATCGACA
CTTTAGCTCCCGCCTCTGGTAACCGTTCTAACGTTGAACGGGCCTCTACCATC
TTAACCCAGGTTGAAACTTCCGGTGAAGGTCACTTTGCCCCTGTGTCTGGTC
GTGGTGGTAAAATCGGTACTATGTTCCGTATGGCCAACATCGCCCAGTTATCT
AACGATCCTGCCACTGCCCAGGAATTCCGTCGGGCTTTCTGGGGTCCTACCA
CTGATTACACCGCCTCCACTTCTCATCCCGATATCTCTGAAGTGCGTCGTAAC
GCCGCCGCCCAGGCTACCACCCCTTAA fnl (SEQ ID NO: 33)
ATGGTGTACTACAACAACGGCATCCCCGTGTACCGGACCATCAAAGAAATCA
AACCCTTCTTTGAATACACCAAAGTCTCGGAAGTGTACTGGGAACGGCCCGT
GCCCGAAATCGTGAAAATCCGGGATGGCGAACTGTCAGTGGTGCTCATTCAC
GGCATTGACCCCATGGAAGTGAACGGTAGTTGGACCCTGTACAAAGAATACT
TTGTGAATACCTGGAATAGTCTGCTGCCCAAAAATTGTGGTCTGTACATCTTTA
TCTACCCCACCCTGGATGTGCCCCTGGAAGAAACCGCCAAAATTCTGGTCGA
TGAAATCATCAAACTGAATAAAAAAGTGAATATCTACGCCCACAGTATGGGTG
GCATTCTGCTGCGGTACGTGCTGCAAAATGAAGAATTTCGGGAATTTGTGAAC
AAAATCATCTTCGCCGGCACCCCCCACCTGGGCACCCCGCTGGCCAATTTTG
TGGTGCTGGACAAGAGCGTGCTGAAGTTTCACCCCAAATGGGACATCATCAA
GACCGTGATTCTGATGGCCAATACCGCGTGGGTGTTTATTGATGCGCCCAAT
TACAAATACCTGACCTTTGGCTTTGAAAAACCCGAAATTCCCGAAAATATCAAT
TTTATGAATTTTGCCGCCAAAATCAACGCCAACACCAGTAGCATCGTGAAAAA
TCTGATCAATACCGATTTTTTTTCATCTATTGCGCTGCAAATTCTCGAAAGTAC
CATCAAGATCATTTACCCCAAAGATTCCGATTTTACCCAAAATGATGGGATGG
TGCCCCTGTTCAGCGCGACCTACTACGGTAATGAAAAGGTGTTTGAAGGCTTT
GACCACGCCGACCTGGCCATTAGCGAGACCATTGTGAAGGAAGCGATCAAAT
ACTTTTTTGGCGAATAA btl (SEQ ID NO: 34)
ATGATGAAAGGCTGCCGGGTGATGGTTGTGTTGCTCGGTTTATGCTTTGTGTT
CGGCTTATCGGTCCCGGGTGGGCGGACTGAAGCGGCTTCCTTACGCGCCAA
TGATGCGCCGATTGTGTTACTCCATGGGTTTACCGGTTGGGGTCGTGAGGAA
ATGTTTGGTTTCAAGTATTGGGGCGGCGTGCGCGGCGATATCGAACAATGGC
TGAACGACAACGGTTATCGTACTTATACTCTGGCGGTCGGTCCGCTCTCGAG
CAACTGGGACCGGGCGTGTGAAGCGTATGCTCAGTTAGTCGGCGGGACTGT
CGATTATGGGGCTGCCCATGCGGCTAAGCACGGCCATGCGCGGTTTGGCCG
CACTTATCCCGGCCTGTTGCCGGAATTGAAACGTGGTGGCCGCATCCATATC
ATCGCCCACAGCCAAGGGGGGCAGACTGCCCGCATGTTAGTCTCGCTCTTAG
AGAACGGTAGCCAAGAAGAGCGGGAGTACGCCAAGGCGCACAACGTGTCGT
TGTCACCGTTGTTTGAAGGTGGTCATCATTTTGTGTTGAGTGTGACTACCATC
GCCACTCCTCATGACGGGACTACTTTAGTCAACATGGTTGATTTCACCGATCG
CTTTTTTGACTTGCAAAAAGCGGTGTTGGAAGCGGCGGCTGTCGCCAGCAAC
GTGCCGTACACTAGTCAAGTATACGATTTTAAGCTCGACCAATGGGGTCTGC
GCCGTCAGCCGGGCGAATCGTTCGACCATTATTTTGAACGGCTCAAGCGCTC
CCCTGTCTGGACTTCGACCGATACCGCCCGCTACGATTTATCCGTTTCCGGT
GCTGAGAAGTTGAATCAATGGGTGCAAGCTAGCCCGAATACTTATTATTTGAG
TTTCTCTACTGAACGGACTTATCGCGGTGCGCTCACTGGCAACCATTATCCCG
AACTCGGTATGAACGCTTTCAGCGCGGTCGTATGCGCTCCGTTTCTCGGTTC
GTACCGCAATCCGACTTTAGGCATTGACAGTCATT bsl (SEQ ID NO: 35)
ATGAAATTTGTAAAACGGCGGATCATTGCCCTGGTAACCATTTTGATGCTGTC
TGTTACCTCGCTGTTTGCGTTGCAGCCGTCAGCCAAAGCCGCTGAACACAAT
CCCGTCGTTATGGTTCACGGTATTGGCGGGGCCTCATTCAATTTTGCGGGCA
TTAAGAGCTATCTCGTATCTCAGGGCTGGTCGCGGGACAAGCTGTATGCCGT
TGATTTTTGGGACAAGACCGGCACCAATTATAACAATGGCCCGGTATTATCAC
GGTTTGTGCAAAAGGTTTTAGATGAAACCGGTGCGAAAAAAGTGGATATTGTC
GCTCACAGCATGGGGGGCGCGAACACCCTGTACTACATCAAAAATCTGGACG
GCGGCAATAAAGTTGCCAACGTCGTGACCCTGGGCGGCGCGAACCGTTTGA
CCACCGGCAAGGCGCTGCCGGGCACCGATCCCAATCAAAAGATTTTATACAC
CTCCATTTACAGCAGTGCCGATATGATTGTCATGAATTACTTATCACGGTTAGA
TGGTGCTCGGAACGTTCAAATCCATGGCGTTGGCCACATCGGCCTGCTGTAC
AGCAGCCAAGTCAACAGCCTGATTAAGAAGGGCTGAACGGCGGGGGCCAG
AATACCAATTAA ggl (SEQ ID NO: 36)
ATGGTTTCCAAAAGCTTTTTTTTGGCTGCTGCGGTAAACGTGGTTGGCGTTTT
GGCTCAAGCTCCTACCGCTGTTCTCAATGATAACGAAGTCATTACTGGTGTGC
TGGAGGGTCAAGTTGATACTTTCAAAGGCATCCCCTTTGCTGACCCGCCCGT
TGCTGACTTGCGGTTTAAGCATCCTCAAAGTTTTACTGGCTCTTACCAGGGTC
TGCAAGCCAAGGATTTTAGCTCCGCTTGTATGCAAATTGATCCCTACAACTCT
CTGACCATTCTGGACAATGTTCTGAACTTGGGCAAAATTATTCCTGAAGACTT
CCGGGGCCCCATTTATGACATGGCCAAGGGTACCGTGTCAATGAGTGAGGAT
TGTCTGTACCTGAACGTTTTCCGTCCCGCTGGTACCAAGCCTAGTGATAAGTT
ACCTGTTATGGTTTGGATTTATGGTGGTGCTTTCATCTATGGTTCTTCTGCTGC
TTACCCTGGTAACGGCTACGTTAAGGAAAGTGTCAAAATGGGCCAGCCCGTT
```

TABLE 1-continued

Synthesized Lipase Genes and Other DNA Sequences

GTGTTTGTTTCTATTAACTACCGTACTGGTCCCTTTGGCTTTTTGGGTGGTGAT
GGCATTACTGCTGAAGGCAATACCAACTCTGGTTTGCACGACCAGCGTAAGG
GTCTGGAGTGGGTTAGCGACAATATTGCCAACTTTGGTGGTGACCCTGATAA
GGTTATGATCTTTGGTGAGTCTGCTGGCGCCATGAGTGTTGGTCATCAGCTG
ATTGCTTATGGTGGTGACAACACTTACAATGGCAAGCCCCTGTTCCATTCTGC
TATTCTGCAGTCTGGCGGTCCTCTCCCTTACTATGACTCTACCTCCGTTGGTC
CCGAAAAGGCTTACAACCGGTTTGCTGAATATGCTGGCTGTGATACTACTGCT
AGTGACGTTGACATTTTGCAATGTCTCCGCAGCAAATCTAGCCAAGTTTTGCA
CGATGCCCAAAACTCGTATGACTTAAAGGACCTGTTTGGCCTCCTCCCCGAAT
TTCTGGGCTTTGGTCCCCGGC $P_{trc}$, the -35, -10, and SD sequences are underlined from
left to right (SEQ ID NO: 37)
CAAGCTG<u>TTGACA</u>ATTAATCATCCGGCTCGTATAATGTGTGGAAGA $Km^R$, the start and stop codons are underlined from left
to right (SEQ ID NO: 38)
CTCTAGCTAGAGTCGACCTGCAGGGGGGGGGGGAAAGCCACGTTGTGTCT
CAAAATCTCTGATGTTACATTGCACAAGATAAAAATATATCATCATGAACATA
AAACTGTCTGCTTACATAAACAGTAATACAAGGGGTGTTATGAGCCATATTCA
ACGGGAAACGTCTTGCTCGAGGCCGCGATTAAATTCCAACATGGATGCTGAT
TTATATGGGTATAAATGGGCTCGCGATAATGTCGGGCAATCAGGTGCACAA
TCTATCGATTGTATGGGAAGCCCGATGCGCCAGAGTTGTTTCTGAAACATGG
CAAAGGTAGCGTTGCCAATGATGTTACAGATGAGATGGTCAGACTAAACTGG
CTGACGGAATTTATGCCTCTTCCGACCATCAAGCATTTTATCCGTACTCCTGA
TGATGCATGGTTACTCACCACTGCGATCCCCGGGAAAACAGCATTCCAGGTA
TTAGAAGAATATCCTGATTCAGGTGAAAATATTGTTGATGCGCTGGCAGTGTT
CCTGCGCCGGTTGCATTCGATTCCTGTTTGTAATTGTCCTTTTAACAGCGATC
GCGTATTCGTCTCGCTCAGGCGCAATCACGAATGAATAACGGTTTGGTTGAT
GCGAGTGATTTTGATGACGAGCGTAATGGCTGGCCTGTTGAACAAGTCTGGA
AAGAAATGCATAAGCTTTTGCCATTCTCACCGGATTCAGTCGTCACTCATGGT
GATTTCTCACTTGATAACCTTATTTTTGACGAGGGGAAATTAATAGGTTGTATT
GATGTTGGACGAGTCGGAATCGCAGACCGATACCAGGATCTTGCCATCCTAT
GGAACTGCCTCGGTGAGTTTTCTCCTTCATTACAGAAACGGCTTTTTCAAAAA
TATGGTATTGATAATCCTGATATGAATAAATTGCAGTTTCATTTGATGCTCGAT
GAGTTTTTC<u>TAA</u>TCAG Flanking region 1 (left), with partial cmpR gene (complement,
the start codon of cmpR is underlined). (SEQ ID NO: 39)
TCTGGTTCCAGAGCCTGATTCCCTCATAATCAAGGGTTCATTGACTAGTCTTT
CCAAAGAAATTTTCTTTTCCTTGACTAATGGGTGCTGGCGAGACGCAATTACC
ACGAGGGGATTTTCTAAAAAGTGGCGGATATTAATATCAAGATTTGAGGGCGG
TTTACCCAAAAAGTATAAATCGTCTAAATTATTCGCCAAACGCTCCAAAATTTG
TTGACGATTGCCAATTTGTAGAGAGATGGAAATGCCTGGATATTGTTGACGAA
ATTCCCCCAAAAGTCGTGGCACAAAATATTTGCCTGTGGTAATAGTTGCTAGG
CGCAGGTTACCTTTTTTTAAGCCCTGGAGGTCAGCAATCACTTCCTGCAATTG
ATCCAGGCAAGAGGTAATGTTTTTGCTAGCGTCTAAAACCGCTTGTCCTGCTT
CGGTTAAATAGATTTTTCGGCCAATTTGTTCATAAAGCGGCACCCCGATCGCC
TTGGTGAGTTGCTTCATCTGCTGGGAAACCGTGGGCTGGGTCAGAAACAATT
CCTCCGCCGCCTTGGTGAAACTCCCCGTCCTGGCGATCGCCGCAAAACCTC
AAATTGGTGGAGGGTGGCATTTTT<u>CAT</u>AGTGGATTAATTTTATAGACTACTTCT
ATAAATTACATAAAAAATTGGATATTTATCTATTTTTAGCTTTCCTTAATAATCA
GATCATTCAAGTCCCCTTGGATTAGTCATTGTCCTCGGGCAGGCAGTTTAAAG
CGTCCCCTGGTTTACCTAGCCTAGGAGCCCCAGTGCTCTTCCGTAAACCGGG
GATATCCATGGCGCTTATTTAATTTTTCTGTCTGCCTTTTTTCATAGAAAAAATC
A Flanking region 2 (right), with partial cmpA gene (cmpA
start codon is underlined). (SEQ ID NO: 40)
ATCAAAGTT<u>ATG</u>GGTTCATTCAATCGACGTAAATTTTTGCTCACCTCCGCCGC
CACTGCCACAGGGGCTTTATTTCTGAAGGGTTGTGCCGGCAATCCCCCCGAT
CCCAACGCCGCCAGCACCGGTACTAACCCTTCTCCCCAAGCGGCCGGGGAT
ATTAGCCCAGAAATGATGCCCGAAACCGCCAATATCAAACTAGGCTACATTCC
CATTGTGGAAGCTGCCCCATTGATCATTGCTCAAGAAAAAGGTTTCTTTGCCA
AATATGGCATGACCGGTGTGGAAGTCTCCAAACAAGCCAACTGGGCCTCCGC
TAGAGATAACGTCACCATTGGTTCCCAGGGAGGCGGCATCGATGGCGGCCA
ATGGCAAATGCCCATGCCTCACCTGATTACGGAAGGGATCATTACCAATGGC
AACAAGGTGCCCATGTATGTATTGGCCCAATTGATTACCCAGGGAAATGGTAT
TGCCGTAGCACCAATGCATGAAGGCAAAGGGGTAAACCTGGATATCACCAAA
GCGGCGGACTATATCAAGGGCTTTAACAAAACCAATGGCCGCAAATTTAAGG
CAGCCCACACCTTCCCTAACGTTAACCAAGATTTTTGGATTCGTTACTGGTTT
GCGGCCGGAGGCGTTGATCCTGACACCGATATTGACCTACTGGCTGTGCCTC
CCGCTGAAACAGTCCAGGGCATGCGCAACGGTACCATGGATGCTTTTAGCAC
TGGAGATCCTTGGCCCTATCGCATCGTGACAGAAACATTGGCTACATGGCC
GGTTTAACTGCCCAAATTTGGCCCTATCACCCGGAAGAGTACCTCGCCATTC
GAGCGGAT

TABLE 2

Primers used in this research.

| Name | SEQ ID NO: | Sequence |
|---|---|---|
| cmpR-s | 41 | TCT GGT TCC AGA GCC TGA TTC CCT CAT AAT CAA G |
| cmpA-a | 42 | ATC CGC TCG AAT GGC GAG GTA CTC TT |
| 568-S-cmpR | 43 | GCC TTT TTT CAT AGA AAA AAT CAA GCT GTT GAC AAT TAA TCA TCC G |
| cmpR-A-568 | 44 | CGG ATG ATT AAT TGT CAA CAG CTT GAT TTT TTC TAT GAA AAA AGGC |
| KM-S-568 | 45 | AAG TCG ACA AGC ATG CAA AGC TCT CTA GCT AGA GTC GAC CTG CA |
| 568-A-KM | 46 | TTG AAT GAA CCC ATA ACT TTG ATC TGA TTA GAA AAA CTC ATC GAG C |
| LIP-S-S6F1 | 47 | TCC GGC TCG TAT AAT GTG TGG AAC TTT AAG AAG GAG ATA TAC ATA TG |
| S6F1-A-LIP | 48 | CAT ATG TAT ATC TCC TTC TTA AAG TTC CAC ACA TTA TAC GAG CCG GA |
| KMR-S-LIP | 49 | TAA TCT CGA GCA CCA CCA CCA CCC TCT AGC TAG AGT CGA CCT GCA |
| LIP-A-KMR | 50 | TGC AGG TCG ACT CTA GCT AGA GGG TGG TGG TGG TGC TCG AGA TTA |
| cmpA-S-KM | 51 | GCT CGA TGA GTT TTT CTA ATC AGA TCA AAG TTA TGG GTT CAT TCA A |
| KM-A-cmpA | 52 | TTG AAT GAA CCC ATA ACT TTG ATC TGA TTA GAA AAA CTC ATC GAG C |
| EU-S-NotI | 53 | ATG CGG CCG CAT GCG TAG CTC CTT AGT GCT GTT C |
| EU-A-BamHI | 54 | CTG GAT CCT TAA TCA CAC TCA GAA ATG GGA CCG |
| HM-S-NotI | 55 | ATG CGG CCG CAT GCC CAT GAA AAT TAA TCG TTA CGC |
| HM-A-BamHI | 56 | CTG GAT CCT TAA GGG GTG GTA GCC TGG GCG GC |
| AY-S-NotI | 57 | ATG CGG CCG CAT GAA ATG CTG TCG GAT TAT GTT TGT G |
| AY-A-BamHI | 58 | CTG GAT CCT TAA GGC TGC AAG CTC GCC AAC |

$CO_2$ Limitation Pretreatment, Heat Treatment and FFA Extraction.

After cultures achieved $5 \times 10^8$ cells/ml, they were transferred to sealed vessels for $CO_2$ limitation with the same illumination to grow for one additional day. Cells were concentrated by centrifugation (SORVALL, RC5CPLUS, 6000 g×10 min) and resuspended at densities of about $10^{11}$ cells/ml. The concentrated cells were treated at various temperatures for different times. The cell lysates were extracted by one volume of hexane with 1/100 volume of 1M $H_3PO_4$, and shaken at 37° C. for 2 hours. After centrifugation (6000 g×10 min), 200 μl of the upper organic layer was collected and analyzed by GC (Gas Chromatography) (9). If the GC readings for FFA were above 500 mg/l, the samples were diluted for remeasurement.

Continuous Semi-Batch Cultivation and Recovery.

4-liter cultures were grown at 27° C. in a 5-liter glass rectangular container and aerated with 1 l air/min to a cell density of $5 \times 10^8$ cells/ml (FIG. 1A). One liter of culture was transferred into a sealed vessel for $CO_2$ limitation, and one liter of fresh BG-11 medium was added into the culture container to restore the culture volume to 4 l. For the thermorecovery strain SD338, the one-liter culture was pretreated with $CO_2$ limitation as described above for one day (FIG. 1B), concentrated into about 3 ml by centrifugation, and kept at 46° C. for two days in a thermostatic block (FIG. 1C). For the GR strain SD237, the one-liter culture was kept in the sealed flask in the light incubator for 7-10 days until the color turned yellow (FIG. 2), and the lysate was extracted by 100 ml hexane with continuous agitation for at least 12 hours at 25° C.

Statistical Analysis.

For the data expressed as means±standard deviation, student's T-test was used for pair-wise comparisons. $P<0.05$ was considered statistically significant.

Example 1

Construction of Thermorecovery Strains

Seven thermostable lipases (2, 5, 6, 13, 17-19) with optimal temperatures ranging from 40° C. to 70° C. (Table 3) were chosen. By using the double cross-over recombination method (7), the synthesized lipase genes were inserted with a constitutive promoter $P_{trc}$ into SD100 (the wild-type Synechocystis sp. PCC6803) immediately after the $CO_2$ limitation inducible promoter $P_{cmp}$ (8; herein incorporated by reference), resulting in seven SD strains each with one of the thermolipase genes (Table 3). The genotype of each strain has the general form: cmpR $P_{cmp}$ $P_{trc}$ [lipase gene] $Km^R$ cmpA (Table 1). The doubling time of these strains was determined at 27° C. based on the cell density increase during the exponential growth stage (9). The doubling times for most strains are close to that of SD100 (17.3 h) at 27° C. (Table 3), indicating that synthesis of these lipases with a constitutive promoter in SD100 cells does not significantly affect cell growth rate at a low temperature.

TABLE 3

Thermostable Lipases Used in This Research

| Protein Accession No. | Redesigned Gene | Organism | Optimal Temp. | Activity Remarks from References | SD strain | Doubling time (h) for SD strain at 27° C. |
|---|---|---|---|---|---|---|
| JC8061 | gtl | Geobacillus sp. Strain T1 | 65° C. | <10% lose for 30 min at 60° C. (5) | SD334 | 18.5 |
| ABV69591 | tll | Thermomyces lanuginosus | 60° C. | 15% lose for 1 h at 60° C. (19) | SD335 | 23.0 |

TABLE 3-continued

Thermostable Lipases Used in This Research

| Protein Accession No. | Redesigned Gene | Organism | Optimal Temp. | Activity Remarks from References | SD strain | Doubling time (h) for SD strain at 27° C. |
|---|---|---|---|---|---|---|
| ADI78874 | sll | *Streptomyces lividans* | 60° C. | <10% lose for 30 min at 60° C. (2) | SD336 | 18.1 |
| YP_001410837 | fnl | *Fervidobacterium nodosum* Rt17-B1 | 70° C. | 10% lose for 24 h at 60° C. (18) | SD338 | 21.9 |
| AAF40217 | btl | *Bacillus stearothermophilus* P1 | 55° C. | 90% lose for 12 h at 60° C. (13) | SD339 | 17.6 |
| NP_388152 | bsl | *Bacillus subtilis* strain 168 | 40° C. | secreted alkaliphilic lipase (6) | SD340 | 18.5 |
| ABI13535 | ggl | *Galactomyces geotrichum* Y05 | 50° C. | 40% lose for 24 h at 60° C. (17) | SD341 | 24.8 |

Example 2

Cell Death at Elevated Temperatures with $CO_2$ Limitation Pretreatment

Figure 3A:
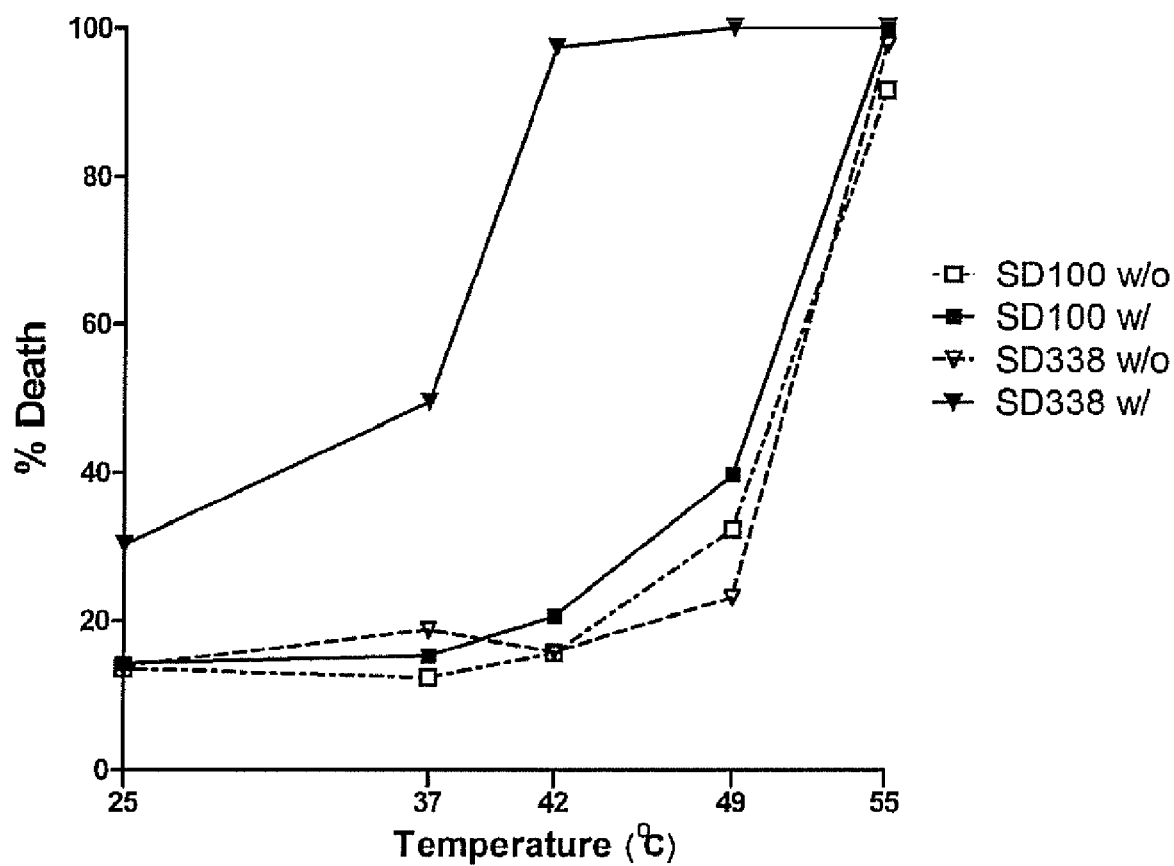
FIG. 3 depicts a graph and fluorescent microscope images showing cell death of SD338 and SD100 at elevated temperatures. (A) The cell death for SD338 and SD100 concentrates kept at different temperatures for one day. 'w/' means with one-day $CO_2$ limitation pretreatment, 'w/o' means cells were directly concentrated without the pretreatment. (B) and (C) Fluorescence microscopy for SD100 and SD338, respectively. Both samples were treated at 42° C. for one day with pretreatment, and then stained with SYTOX. Red indicates live cells, blue and green indicate dead cells.
Figure 3:
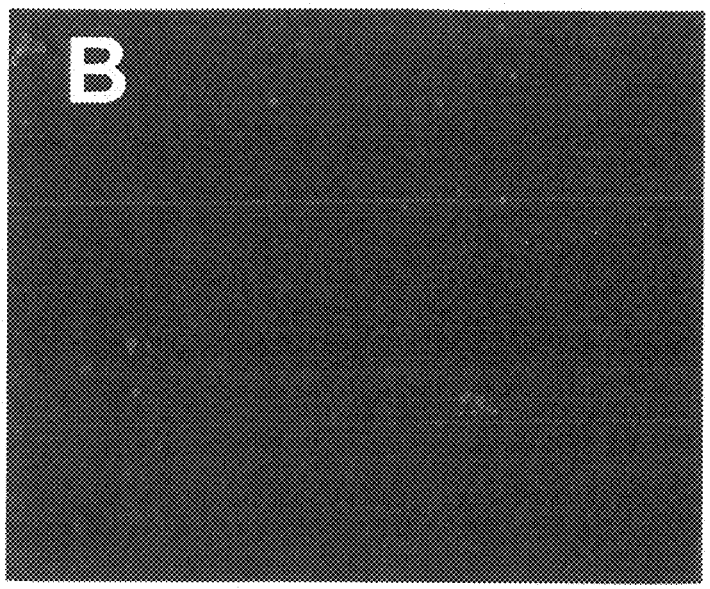
Figure 3:
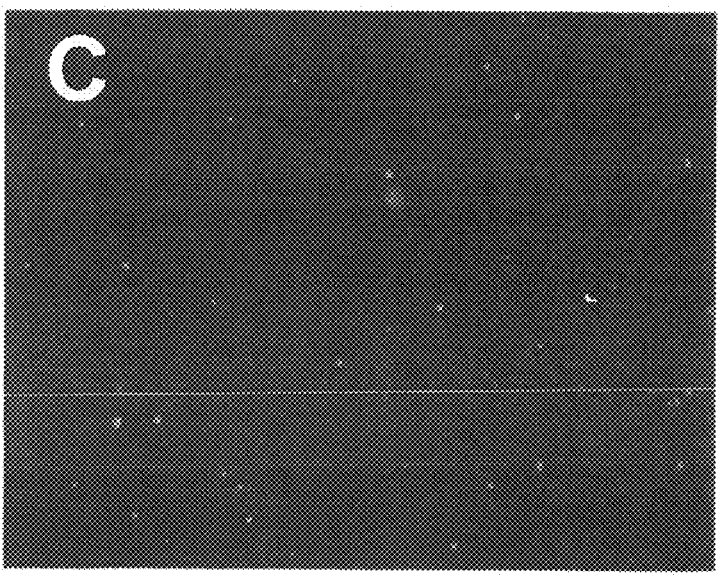

It was postulated that under the control of $P_{cmp}$ and $P_{trc}$ promoters, the thermostable lipase genes would be expressed at a basal level by $P_{trc}$ during normal growth with the expression boosted by $P_{cmp}$ under $CO_2$ limitation conditions prior to culture concentration. To test the effect of $CO_2$ limitation pretreatment, the percentages of cell death with and without the one-day $CO_2$ limitation before concentration was compared. The cell death % was measured by SYTOX staining (7) in the biomass concentrates (about $10^{11}$ cells/mL) treated by elevated temperatures (47° C.) for one day. The cell death % of a typical strain, SD338, was compared with SD100 (FIG. 3). The fractions of cell deaths for the other SD strains were similar to that of SD338 (Table 4). It was observed that cell death increased with temperature with all cells dying at 55° C. in one day (Table 4). The SD strains with recombinant thermostable thermolipase genes exhibited significantly higher death % than SD100 at elevated temperatures (Table 4, FIG. 3). $CO_2$ limitation pretreatment resulted in significantly increased cell death % compared to direct concentration without prior $CO_2$ limited growth (FIG. 3A, from 15.8% to 97.4% for SD338 at 42° C.), indicating that $CO_2$ limitation pretreatment is beneficial in the thermorecovery process.

TABLE 4

Cell Death Percentage of Thermorecovery Strains at Elevated Temperatures

| | Death % (without/with $CO_2$ limitation) Temperature | | | | |
|---|---|---|---|---|---|
| Strains | 25° C. | 37° C. | 42° C. | 49° C. | 55° C. |
| SD100 | 13.6/14.3 | 12.4/15.3 | 15.6/20.6 | 32.3/39.7 | 91.6/100 |
| SD334 | 51.5/64.2 | 64.2/62.4 | 81.7/88.7 | 85.4/99.0 | 98.6/100 |
| SD335 | 22.4/42.2 | 24.8/55.3 | 55.7/75.9 | 13.7/100 | 97.5/100 |
| SD336 | 42.6/73.6 | 61.2/69.7 | 65.7/80.1 | 56.2/100 | 100/100 |
| SD338 | 13.9/30.34 | 18.8/49.5 | 15.8/97.37 | 23.1/100 | 97.7/100 |
| SD339 | 78.9/23.5 | 2.3/30.0 | 5.5/8.5 | 22.3/99.3 | 97.1/100 |
| SD340 | 18.0/32 | 28.2/28.7 | 26.3/42.9 | 44.0/93.0 | 98.0/100 |
| SD341 | 15.8/45.4 | 25.4/41.2 | 29.3/41.7 | 29.9/100 | 99.0/100 |

Example 3

FFA Release During Thermorecovery

Figure 4A:
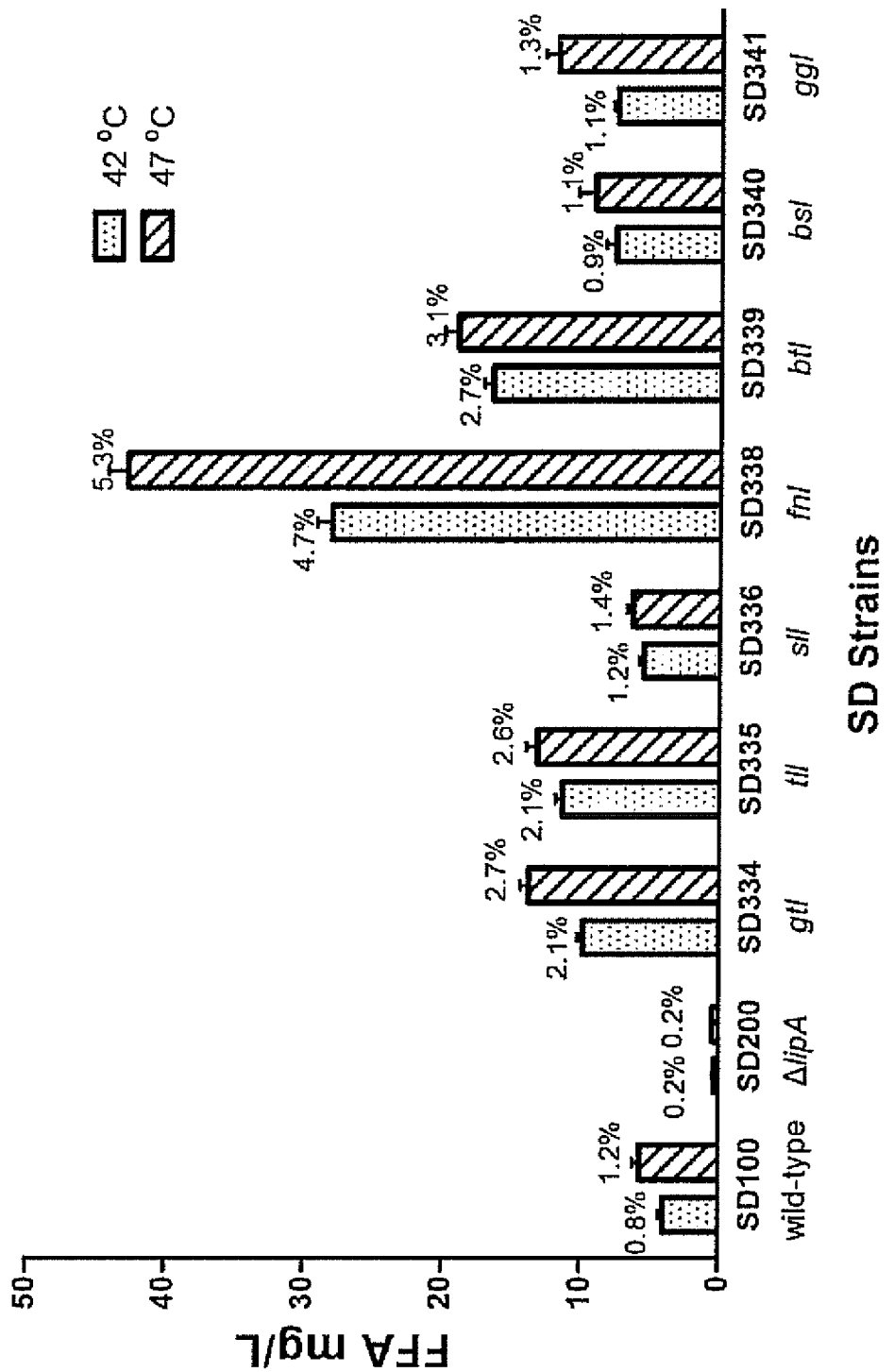
FIG. 4 depicts three graphs showing FFA yields in thermorecovery. (A) FFA yields for different SD strains during thermorecovery. The genetic information such as gene integrated is indicated below the strain names. SD200 is a control strain with a native lipase gene (lipA, sll1969) deletion. The % FFA of cell dry weight for each sample is indicated above the column. (B) FFA % of cell dry weight at different treatment times for SD338 and SD339 with SD100 as a control. 'Day 0+0' means no $CO_2$ limitation pretreatment and no heat treatment. 'Day 1+0' means one day pretreatment and no heat treatment. 'Day 1+1' means one day pretreatment and one day heat treatment. (C) FFA % of SD338 cell dry weight at various temperatures for two days with pretreatment.
Figure 5:
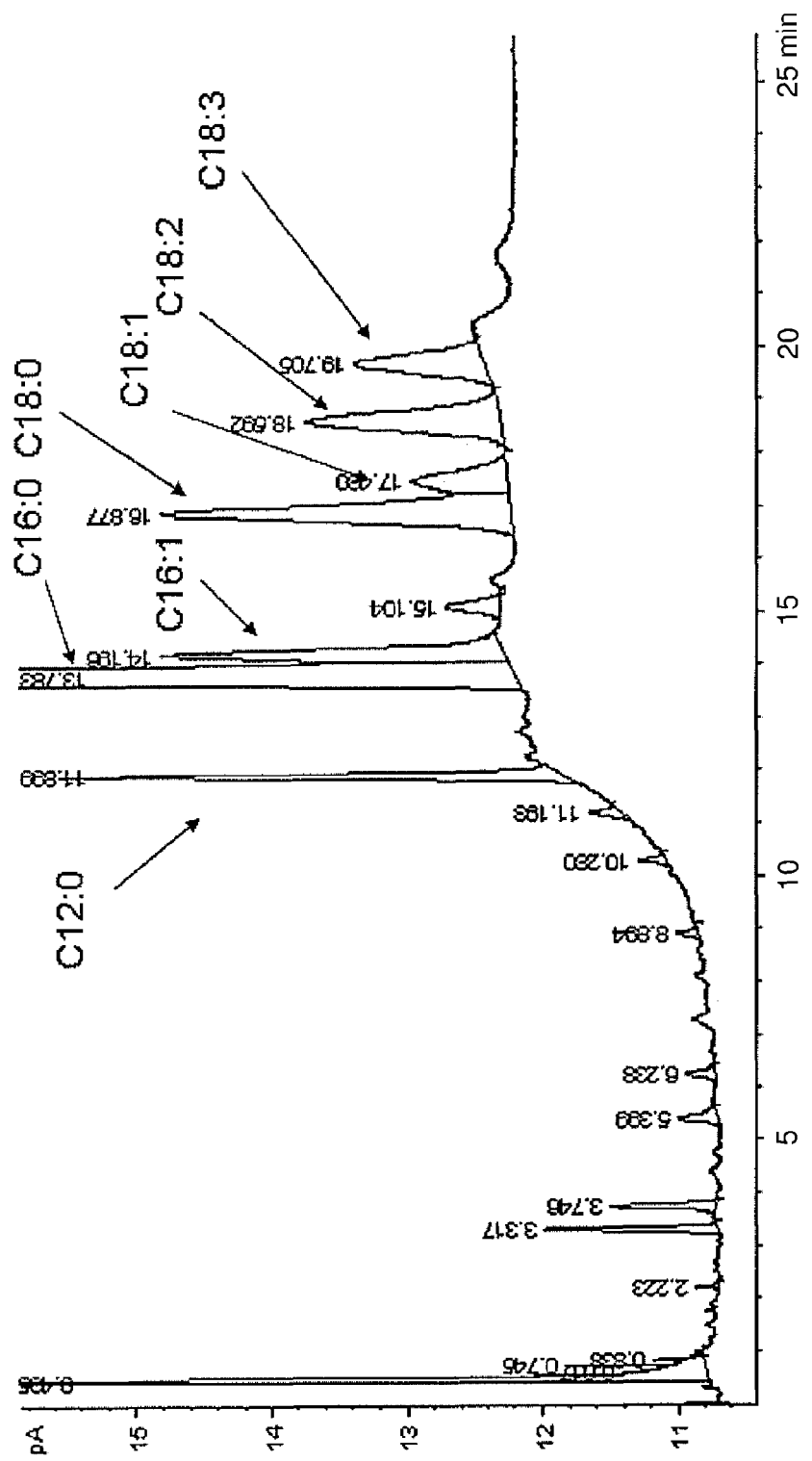
FIG. 5 depicts a gas chromatography (GC hereafter) analysis trace of the FFA released from SD338 after thermorecovery. The types of FFA are indicated for the GC peaks.

The main goal for thermorecovery is to recover FFA from cyanobacterial biomass, so the FFA yields of the SD strains was measured, and the recovery efficiencies to dry weights normalized (FIG. 4A). In this experiment, cell concentrates from 25 ml cultures after one-day $CO_2$ limitation pretreatment were treated at 42° C. and 47° C. for 24 hours. SD100 and SD200 served as controls, where SD200 (Δsll1969) is a native lipase (LipA) deficient strain (8). It was found that SD338 with fnl from *Fervidobacterium nodosum* Rt17-B1 to be the best thermorecovery strain out of the seven trial strains with a yield of 42.7 mg FFA per liter of culture at 47° C. for thermorecovery, which accounts for 5.3% of cell dry weight (FIG. 4A). It was postulated that the background FFA release for the SD100 culture is from the hydrolyzing activity of the native lipase LipA encoded by sll1969, as SD200 (Δsll1969) exhibited much lower FFA release by the same heat treatment. GC analysis showed that the main FFA species are C16:0, C18:3, C18:2, C18:1 and C18:0 (FIG. 5), the same as the SD100 membrane lipid profile (8), suggesting that the recovered FFA are hydrolyzed from membrane lipids.

Figure 4B:
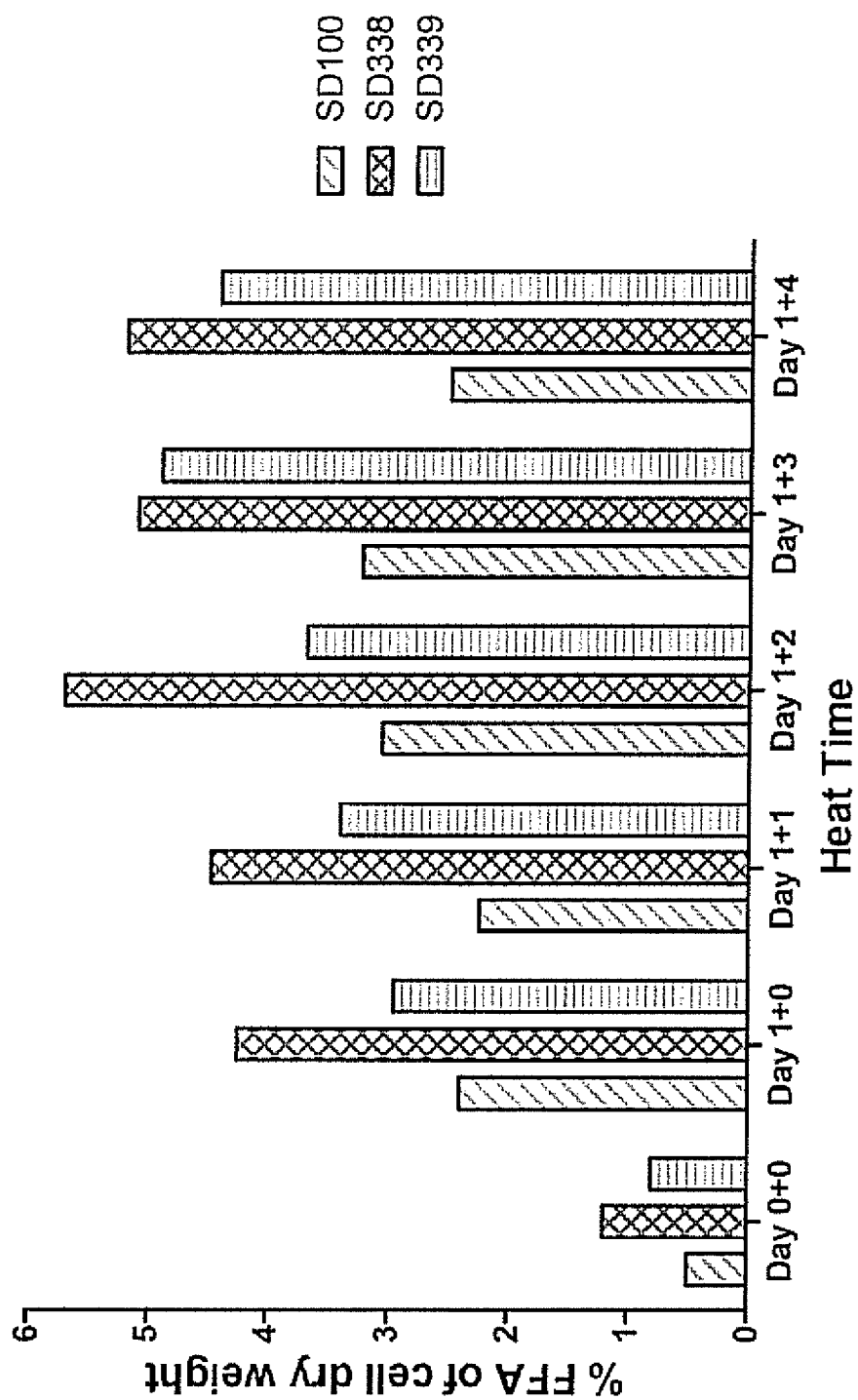
Figure 4C:
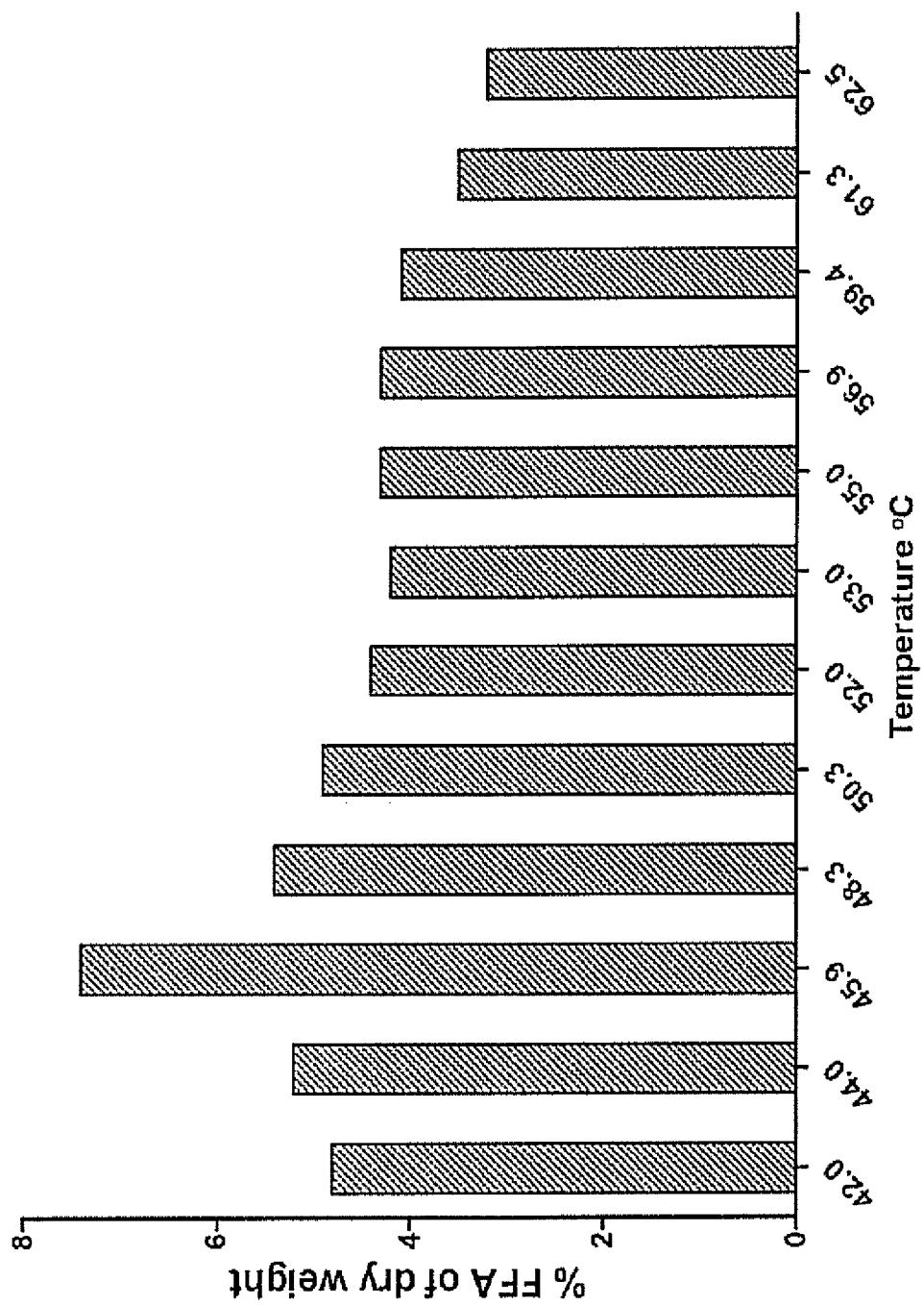

To determine the optimal heat treatment time, samples were taken from six time points: before $CO_2$ limitation pretreatment, right after $CO_2$ limitation pretreatment, and heat treatments at 47° C. for one to four days after pretreatment. Results showed that for SD338, the highest yield was measured when the culture was pretreated for one day, concentrated, and then heated at 47° C. for two days (FIG. 4B). To determine the optimal temperature for SD338 thermorecovery, a temperature gradient from 42° C. to 62.5° C. was created with 12 temperature points for two-day heat treatment after one-day pretreatment. Results showed that the optimal temperature for SD338 is around 45.9° C. Higher than that, the recovery efficiency was reduced. (FIG. 4C).

Example 4

Thermorecovery vs. GR in Continuous Production

Figure 2:
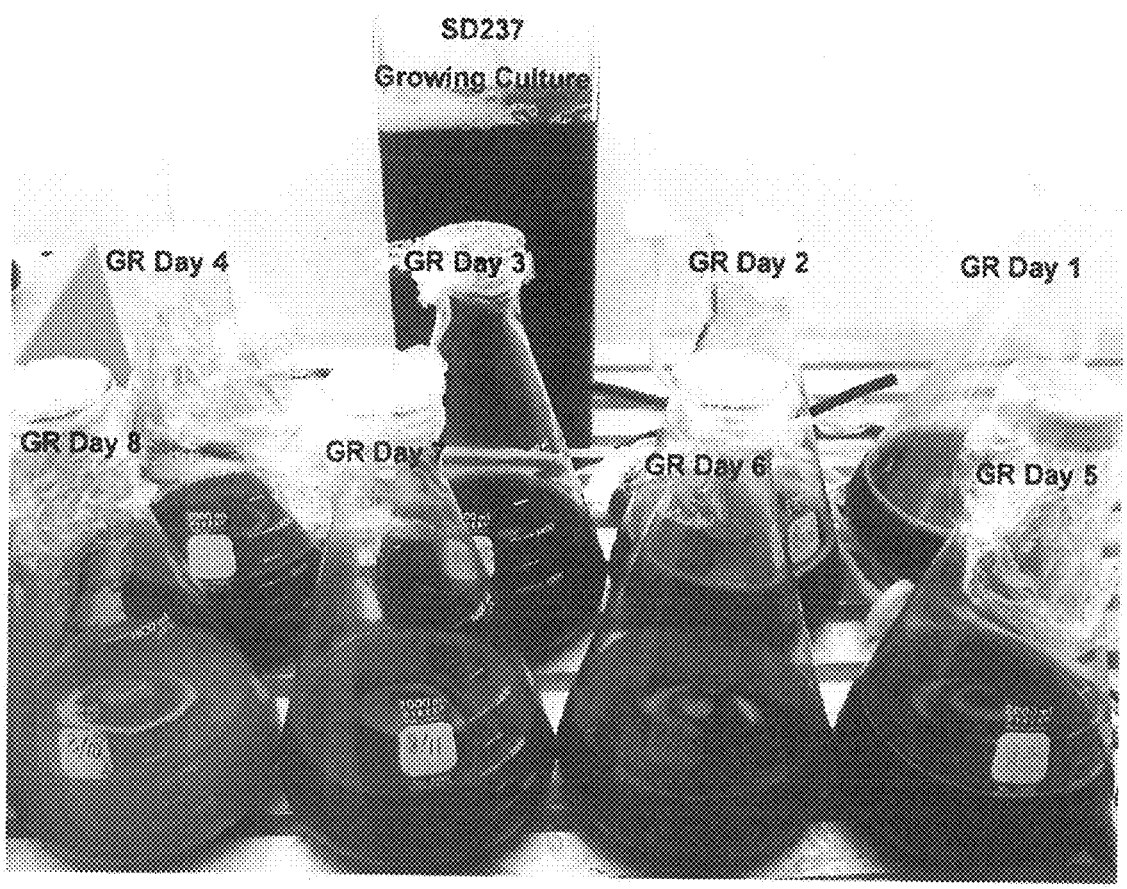
FIG. 2 depicts an image showing continuous semi-batch production experiment with Green Recovery (GR hereafter). The continuous growing SD237 culture is placed in the back of a light incubator. Two rows of SD237 cultures in sealed flasks are undergoing GR with $CO_2$ limitation, and the time they had been sealed are indicated on the flask top.
Figure 6:
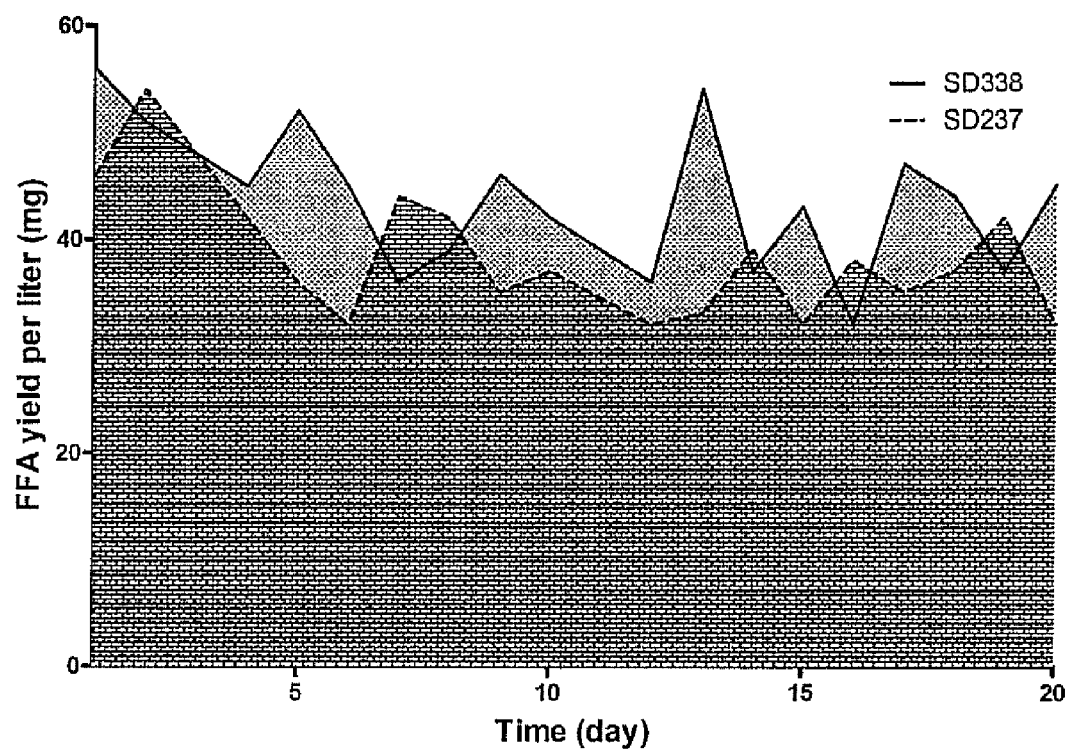
FIG. 6 depicts a graph showing FFA yields for SD338 and SD237 in continuous production experiments. Each day, one-liter of culture was drawn and one-liter fresh medium was fed to the continuous culture. SD338 underwent thermorecovery, while SD237 underwent GR.

To test the durability of thermorecovery, a semi-batch continuous production with 4-liter cultures for 20 days was performed. A 4-liter SD338 culture was grown to $5 \times 10^8$ cells/ml at 27° C., one liter culture was harvested each day, and the harvested amount was replaced with one liter fresh medium (FIG. 6). The harvested cultures were transferred into a capped separation funnel for $CO_2$ limitation pretreatment for one day, and then the cells were concentrated into 3 ml by centrifugation. Based on the optimal parameters determined above, the temperature of the biomass concentrates were elevated to 46° C. for two days, and then the lysates were extracted with 3 ml hexane. The average daily FFA yield for this thermorecovery experiment was about 43.9±6.6 mg, and this yield was maintained for 20 days without significant decrease (FIG. 6). To compare the yield and cost of the thermorecovery and GR strategies, a semi-batch continuous production was also performed with a GR strain SD237. The SD237 culture was grown in the same way as SD338. One liter SD237 culture was transferred into a sealed flask each day for GR, but the entire GR lysis process took 7 to 10 days until the whole culture discolored (FIG. 2). Each liter of lysate was then extracted with 100 ml hexane. The detailed results of these two experiments are compared in Table 5.

TABLE 5

Thermorecovery and GR in Continuous Production Experiments

| Experiment Details | Thermorecovery | GR |
|---|---|---|
| Total culture volume | 4 liters | 4 liters |
| Daily culture harvested | 1 liter | 1 liter |
| Daily refilled fresh medium | 1 liter | 1 liter |
| Time for $CO_2$ limitation | 1 day | 7-10 days |
| Lysate from daily harvested culture | 3 ml | 1 liter |
| Space for the recovery process | 1 heat block | 10x 1-l flasks with illumination |
| Hexane for daily harvested culture | 3 ml | 100 ml |
| Centrifuge volume for separating hexane | 6 ml | 1.1 liter |
| Average daily FFA yield | 43.9 ± 6.6 mg | 38.4 ± 6.2 mg |
| Water usage | Directly recyclable as supernatant | Not directly recyclable as $H_3PO_4$ and hexane added and mixed. |

From this comparison, several advantages of thermorecovery over the original GR process were found, with the biggest contribution being light-independence (Table 5). First, the time for $CO_2$ limitation with light is significantly shortened from 7-10 days for GR lysis to only one day for $CO_2$ limitation pretreatment, because the lipases only need to be synthesized during the $CO_2$ limitation pretreatment for the thermorecovery process, whereas they need to be synthesized and lyse the cells throughout the GR process. The light independence of thermorecovery saves the illumination period for each harvested culture. Second, the daily biomass volume to be processed is much less for thermorecovery (3 ml) than for GR (1 l). This significantly reduces the space, solvent and energy required for FFA recovery. In the extraction process, the smaller volumes in the thermorecovery process reduces the hexane usage from 1/10 of original culture volume to 1/200, and also saves energy during the separation of hexane from the FFA-depleted aqueous phase by centrifugation. Third, the average daily FFA yield for thermorecovery (44 mg) is higher than that for the GR process (38 mg). The higher lipase concentration for the thermorecovery process due to culture concentration following the $CO_2$ limitation pretreatment is another basis for the superiority over the GR process in which the lipases are diluted into the whole culture volume when membrane damage precludes lipase retention inside the cells leading to a much reduced level of lipase enzyme activity.

Discussion for Examples 1-4

Thermorecovery was developed when the disadvantage of the light dependence as a defect of the GR process was realized. This was remediated by synthesizing thermostable thermotolerant lipases during growth in the presence of light before commencement of FFA recovery with subsequent induction of lipase activities in concentrated cultures in the dark by elevated temperatures. With thermorecovery, the biomass volume to be processed is significantly reduced, resulting in much less space, time, equipment, reagents and energy to handle the biomass. Elevating the temperature of biomass concentrates from 27° C. to 46° C. needs about 240 J per liter of culture, and the use of solar energy to supply the heat for elevating the temperature is proposed. At higher temperatures, the risk of FFA biodegradation by contaminating FFA-consuming heterotrophs is also limited. Thus, it is expected that production costs of FFA with thermorecovery at large scale will be drastically lowered from using the GR process.

Thermorecovery was designed to be highly compatible with the current industrial microalgal biofuel process. First, the genetics for thermorecovery is straightforward, with only one thermostable lipase gene needing to be expressed in a microalgal cell. With the current genetic techniques for algae (16), this is feasible for most species. Second, for most production areas, the temperatures for algal open ponds generally range from 20° C. to 30° C. (1), and this ensures the normal growth of algal biomass without display of thermotolerant lipase activities. Third, the water and nutrients can be easily recycled by the industrial algal cultivation process (15). Fourth, thermorecovery can be directly plugged into the current algal biofuel process, which includes cultivation, flocculation, concentration, cell digestion and extraction (15). It is anticipated that adoption of thermorecovery will significantly reduce the cost in cell digestion and extraction by just heating the biomass. It is also anticipated that with the destruction of microalgae cells, the triaclyglycerol content in an algal cell will be released and easily recovered.

In the thermorecovery process most of the lipids in the cyanobacterial biomass are recovered. This will leave a significant amount of proteins, carbohydrates and nucleic acids in the lysate (4). Many biofuel fermentation systems have been established, such as fatty-acid-derived biofuels (14), or C4 and C5 alcohols (4), or biodiesel by heterotrophic algae (10). The microalgal lysate after thermorecovery may be suitable for some of these fermentation techniques, and the lysate may be used as nutrients for producing additional biofuels or other valuable products.

References for Examples 1-4.

1. Converti A, Casazza A A, Ortiz E Y, Perego P, Del Borghi M. 2009. Effect of temperature and nitrogen concentration on the growth and lipid content of Nannochloropsis oculata and *Chlorella vulgaris* for biodiesel production. Chem. Eng. Process. 48:1146-1151.
2. Cote A, Shareck F. 2010. Expression and characterization of a novel heterologous moderately thermostable lipase derived from metagenomics in *Streptomyces lividans*. J. Ind. Microbiol. Biotechnol. 37:883-891.
3. Gao X, Cao S, Zhang K. 2000. Production, properties and application to nonaqueous enzymatic catalysis of lipase from a newly isolated *Pseudomonas* strain. Enzyme Microb. Technol. 27:74-82.
4. Huo Y X, Cho K M, Rivera J G, Monte E, Shen C R, Yan Y, Liao J C. 2011. Conversion of proteins into biofuels by engineering nitrogen flux. Nat. Biotechnol. 29:346-351.
5. Leow T C, Rahman R N, Basri M, Salleh A B. 2004. High level expression of thermostable lipase from *Geobacillus* sp. strain T1. Biosci. Biotechnol. Biochem. 68:96-103.

6. Lesuisse E, Schanck K, Colson C. 1993. Purification and preliminary characterization of the extracellular lipase of *Bacillus subtilis* 168, an extremely basic pH-tolerant enzyme. Eur. J. Biochem. 216:155-160.
7. Liu X, Curtiss R, 3rd. 2009. Nickel-inducible lysis system in *Synechocystis* sp. PCC 6803. Proc. Natl. Acad. Sci. U.S.A. 106:21550-21554.
8. Liu X, Fallon S, Sheng J, Curtiss R, 3rd. 2011. $CO_2$-limitation-inducible Green Recovery of fatty acids from cyanobacterial biomass. Proc. Natl. Acad. Sci. U.S.A. 108: 6905-6908.
9. Liu X, Sheng J, Curtiss R, 3rd. 2011. Fatty acid production in genetically modified cyanobacteria. Proc. Natl. Acad. Sci. U.S.A. 108:6899-6904.
10. Miao X, Wu Q. 2006. Biodiesel production from heterotrophic microalgal oil. Bioresour. Technol. 97:841-846.
11. Molina Grima E, Belarbi E H, Acien Fernandez F G, Robles Medina A, Chisti Y. 2003. Recovery of microalgal biomass and metabolites: process options and economics. Biotechnol. Adv. 20:491-515.
12. Peralta-Yahya P P, Keasling J D. 2010. Advanced biofuel production in microbes. Biotechnol. J. 5:147-162.
13. Sinchaikul S, Sookkheo B, Phutrakul S, Pan F M, Chen S T. 2001. Optimization of a thermostable lipase from *Bacillus stearothermophilus* P1: overexpression, purification, and characterization. Protein Expr. Purif. 22:388-398.
14. Steen E J, Kang Y, Bokinsky G, Hu Z, Schirmer A, McClure A, Del Cardayre S B, Keasling J D. 2010. Microbial production of fatty-acid-derived fuels and chemicals from plant biomass. Nature. 463:559-562.
15. Stephens E, Ross I L, Mussgnug J H, Wagner L D, Borowitzka M A, Posten C, Kruse O, Hankamer B. 2010. Future prospects of microalgal biofuel production systems. Trends Plant Sci. 15:554-564.
16. Wang H H, Yin W B, Hu Z M. 2009. Advances in chloroplast engineering. J. Genet. Genomics. 36:387-398.
17. Yan J, Yang J, Xu L, Yan Y. 2007. Gene cloning, overexpression and characterization of a novel organic solvent tolerant and thermostable lipase from *Galactomyces geotrichum* Y05. J Mol Catal B: Enzym. 49:28-35.
18. Yu S, Yu S, Han W, Wang H, Zheng B, Feng Y. 2010. A novel thermophilic lipase from *Fervidobacterium nodosum* Rt17-B1 representing a new subfamily of bacterial lipases. J. Mol. Cata. I B: Enzym. 66:81-89.
19. Zheng Y, Guo X, Song N, Li D. 2011. Thermophilic lipase from *Thermomyces lanuginosus*: Gene cloning, experssion and characterization. J. Mol. Catal. B: Enzym. 69:127-132.

Example 5

Alkane Biosynthesis in Cyanobacteria

Figure 7:
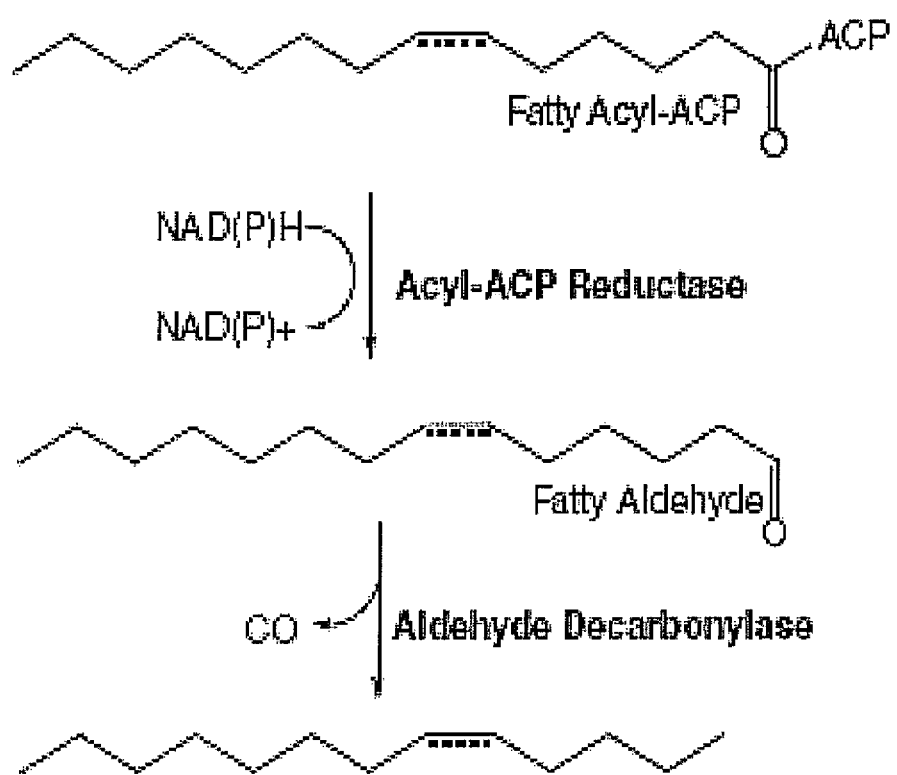
FIG. 7 depicts the alkane biosynthesis pathway in cyanobacteria.

Alkanes, the major constituents of gasoline, diesel, and jet fuel, are naturally produced by diverse species. Alkanes have been reported in a diversity of microorganisms, and the most consistent reports are from the cyanobacteria. An alkane biosynthesis pathway from cyanobacteria was well known (FIG. 7). The pathway consists of an acyl-acyl carrier protein reductase and an aldehyde decarbonylase, which together convert intermediates of fatty acid metabolism to alkanes and alkenes. The aldehyde decarbonylase is related to the broadly functional nonheme diiron enzymes. Heterologous expression of the alkane operon in *Escherichia coli* leads to the production and secretion of C13 to C17 mixtures of alkanes and alkenes. These genes and enzymes can now be leveraged for the simple and direct conversion of renewable raw materials to fungible hydrocarbon fuels.

Figure 8:
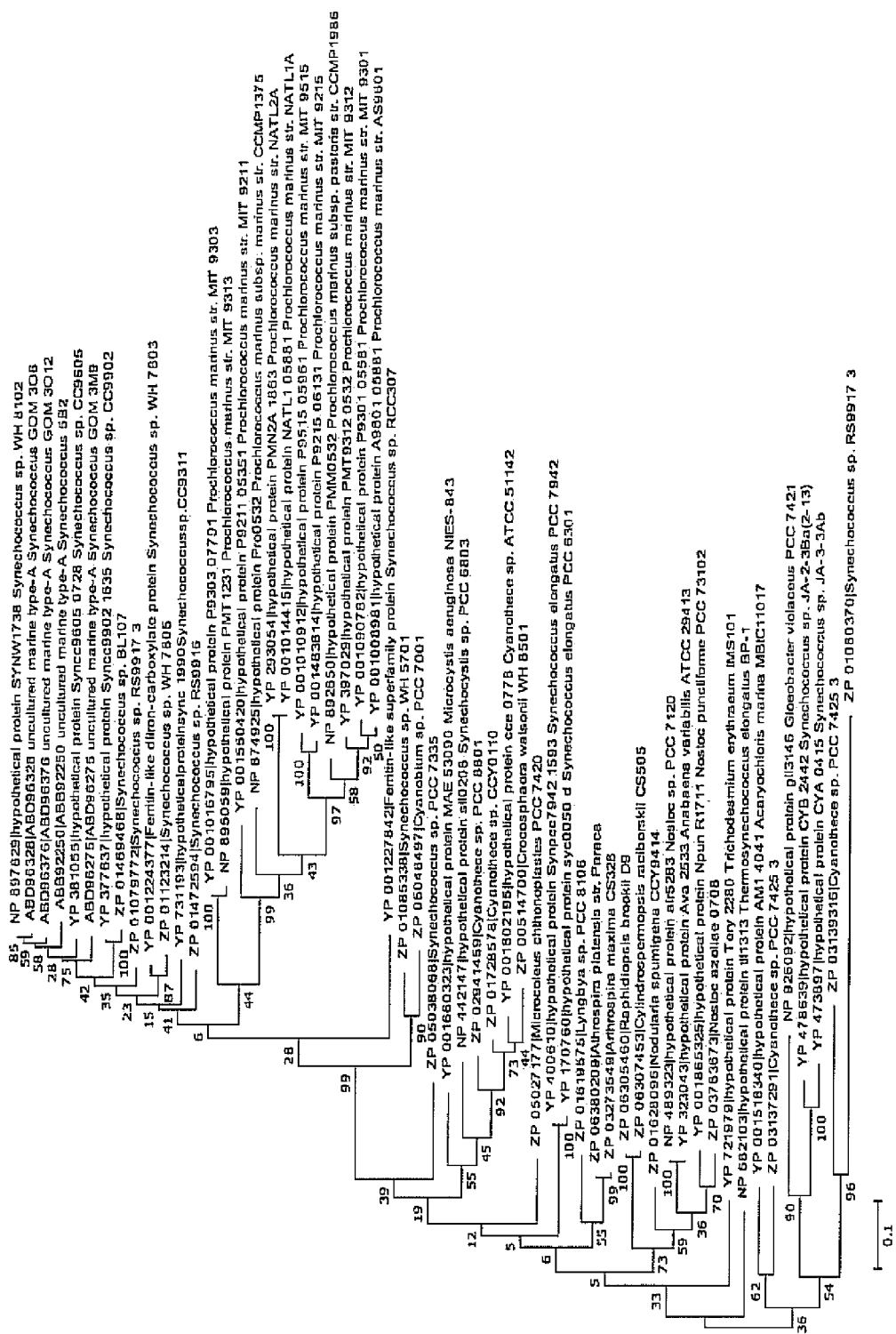
FIG. 8 depicts a phylogentic tree of alkane biosynthesis genes in cyanobacteria. Of these alkane biosynthesis genes, ten genes from *Synechococcus* sp. PCC 7942, *Prochlorococcus marinus* subsp. *Pastoris* str. CCMP 1986, *Nostoc punctiorme* PCC 73102, *Thermosynechococcus elongatus* BP-1, and *Gloebacter violaceus* PCC 7421, were chose for alkane overproduction in *Synechocystis* PCC sp. 6803.

With bioinformatics analysis, the phylogenetic relationship of the alkane production genes in cyanobacteia as shown in FIG. 8 were found. From these alkane production genes, ten alkane biosynthesis genes from five cyanobacterial spieces (i.e., *Synechococcus* sp. PCC 7942, *Prochlorococcus marinus* subsp. *Pastoris* str. CCMP 1986, *Nostoc punctiorme* PCC 73102, *Thermosynechococcus elongatus* BP-1, and *Gloebacter violaceus* PCC 7421) were chosen for overexpression in *Synechocystis* PCC sp. 6803. The strain constructions are listed in Table 6. Some of these alkane overproduction strains are built on the base of a Green Recovery strain such as SD237, so that they are able to release intracellular alkanes with $CO_2$ limitation.

TABLE 6

Alkane overexpression strain constructions.

| Alkane Strains | Genotype | Alkane gene sources |
|---|---|---|
| SD293 | Δsll1951-15::PpsbA210 orf1593 orf1594 | *Synechococcus* 7942 (original) |
| SD294 | Pcmp43::fol RBS shl RBS Δsll1951-15::PpsbA210 aac (7942) Ptrc adc (73102) | *Synechococcus* 7942 *Nostoc* 73102 |
| SD295 | Pcmp43::fol RBS shl RBS Δsll1951-15::PpsbA210 orf1593 orf1594 | *Synechococcus* 7942 (original) |
| SD298 | Pcmp43::fol RBS shl RBS Δ(slr1993-slr1994)-14:: PpsbA210 aac (7942) Ptrc adc (73102) | *Synechococcus* 7942 *Nostoc* 73102 |
| SD303 | Pcmp43::fol RBS shl RBS Δ(slr1993-slr1994)-14:: PpsbA210 aac (7942) Ptrc adc (73102) Δsll1951-15:: PpsbA210 orf1593 orf1594 | *Synechococcus* 7942 *Nostoc* 73102 |
| SD307 | Pcmp43::fol RBS shl RBS Δ(slr1993-slr1994)-14:: PpsbA210 aac (7942) Ptrc adc (73102) Δsll1951-15:: PpsbA210 orf1593 orf1594 Δ(slr2001-slr2002)-17::P psbA210 Ptrc aac (BP-1) Ptrc adc (BP-1) | *Synechococcus* 7942 *Nostoc* 73102 *Thermosynchococcus* BP-1 |
| SD308 | Δ(slr2001-slr2002)-17::P psbA210 Ptrc aac (BP-1) Ptrc adc (BP-1) | *Thermosynchococcus* BP-1 |
| SD309 | Δ(slr2001-slr2002)-17::EHC1 Ptrc aac (1986) Ptrc adc (1986) | *Prochococcus* 1986 |
| SD310 | Δ(slr2001-slr2002)-17::EHC1 Ptrc aac (7421) Ptrc adc (7421) | *Gloebacter* 7421 |

Example 6

Alkane Overproduction in Genetic Modified *Synechocystis* SD Strains

Figure 9:
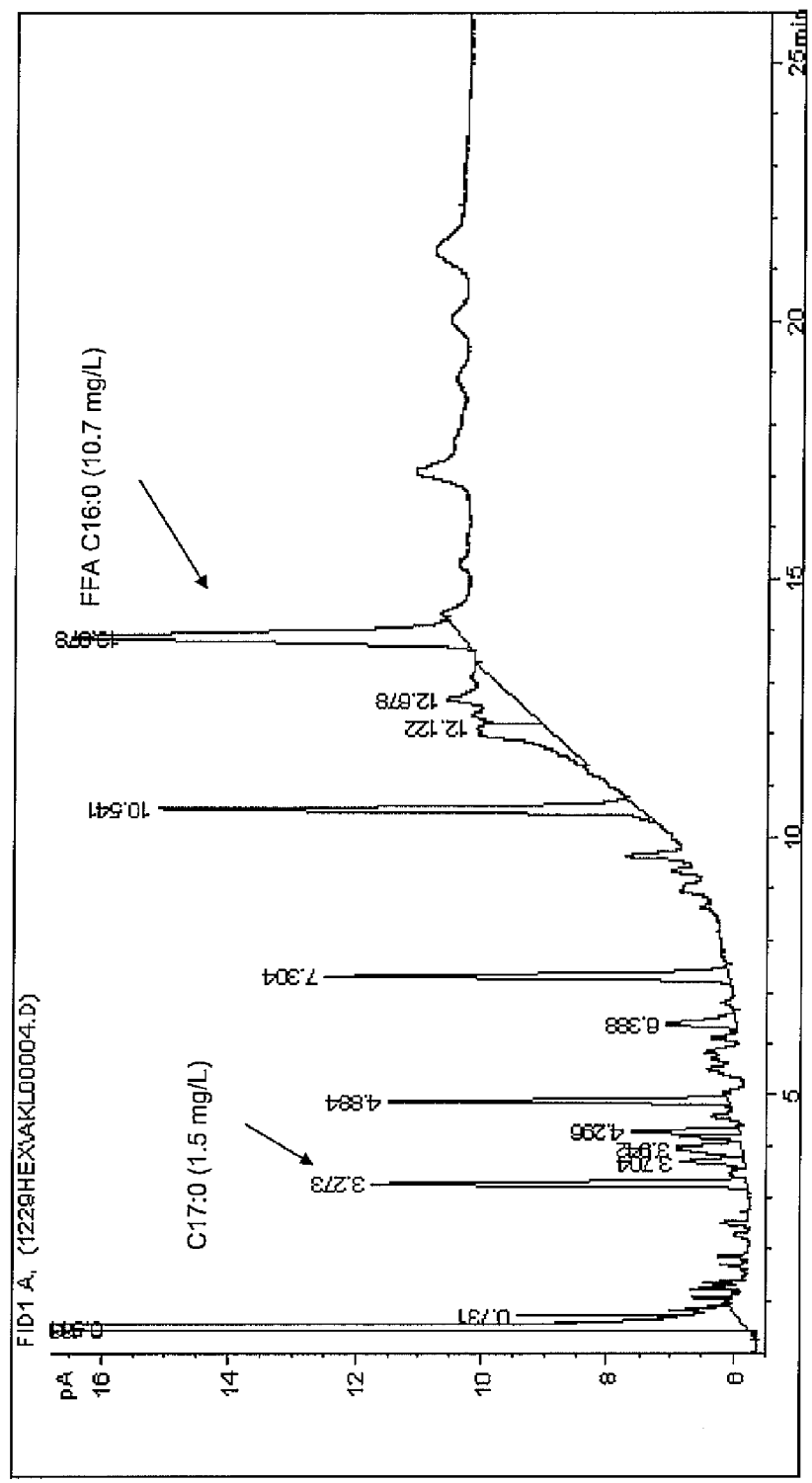
FIG. 9 depicts GC analysis of the alkane production in SD294 culture.

As shown in Table 6, nine strains were constructed for expressing the alkane biosynthesis genes from *Synechococcus* sp. PCC 7942, *Prochlorococcus marinus* subsp. *Pastoris* str. CCMP 1986, *Nostoc punctiorme* PCC 73102, *Thermosynechococcus elongatus* BP-1, and *Gloebacter violaceus* PCC 7421. Alkane biosynthesis was detected in their cultures. The GC analysis of the alkane production in SD294 culture was shown in FIG. 9, with a Heptadecane yield of 1.5 mg/L and $83.3 \times 10^{-13}$ mg/cell, which is a 55.5 fold increase from wild-type SD100 (with a yield of $1.5 \times 10^{-13}$ mg/cell) (Table 7).

TABLE 7

Alkane production in genetically modified *Synechocystis* SD strains

| Strains Gene sources and modification | WT | SD293 Syn7942 (original) ΔS-layer | SD294 Syn7942 Nostoc 73102 ΔS-layer Green Recovery | SD295 Syn7942 (original) ΔS-layer Green Recovery | SD298 Syn 7942 Nostoc 73102 ΔPHB Green Recovery | SD303 Syn 7942 Nostoc 73102 ΔS-layer ΔPHB Green Recovery |
|---|---|---|---|---|---|---|
| Cell density on Day 5 (CFU $10^8$/mL) | 6.5 | 4.3 | 1.8 | 1.4 | 1.4 | 3.0 |
| Heptadecane (C17:0) (mg/L) | 0.1 | 0.6 | 1.5 | 0.9 | 0.36 | 0.83 |
| 10-13 mg/cell | 1.5 | 14.0 | 83.3 | 64.3 | 25.7 | 27.7 |

Example 7

Alkane Overproduction with Green Recovery

Figure 10A:
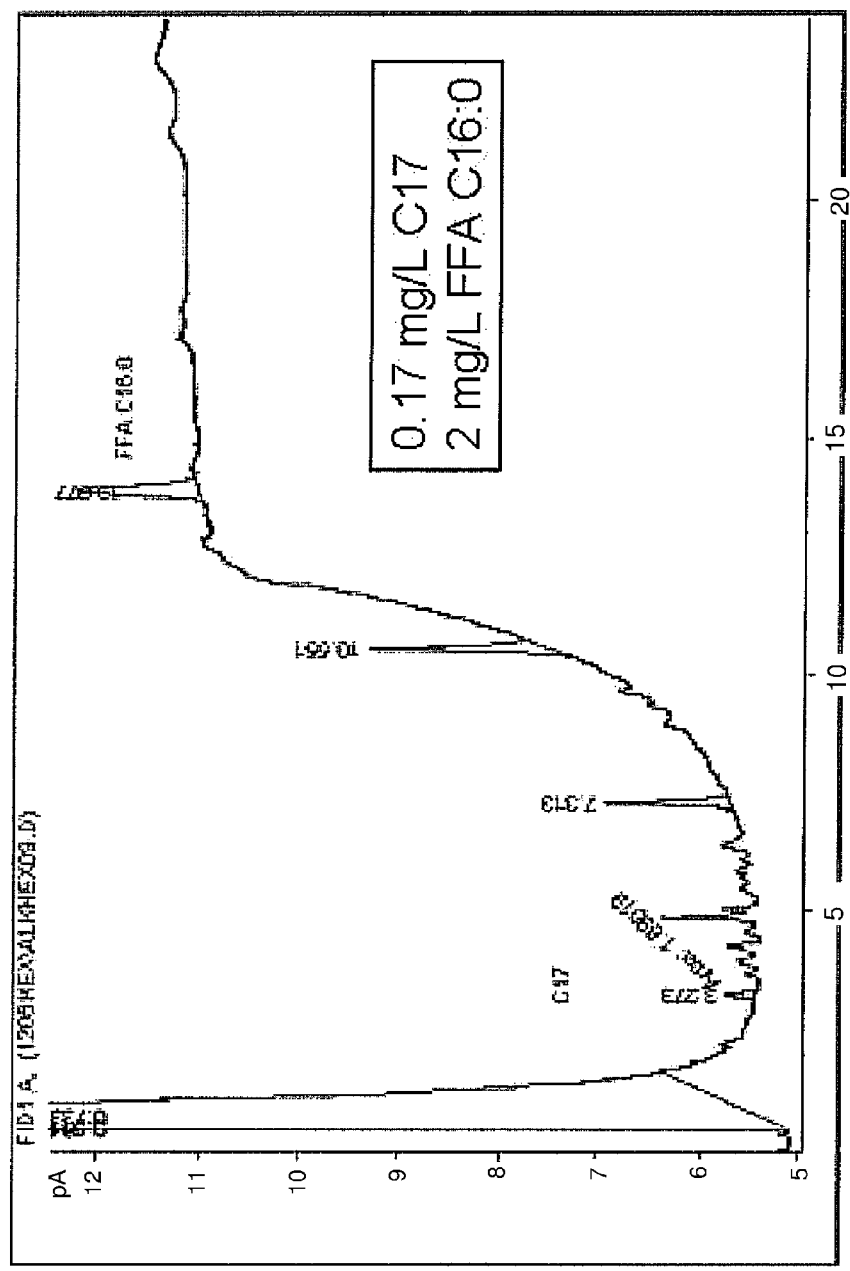
FIG. 10 depicts GC analysis of alkane production and release of alkane by Green Recovery in the SD303 culture. (A) GC analysis of a culture of SD303, which has been grown for 3 day with a cell density of $3\times10^8$ cells/ml. (B) GC analysis of the SD303 culture after Green Recovery induced by $CO_2$ limitation.
Figure 10B:
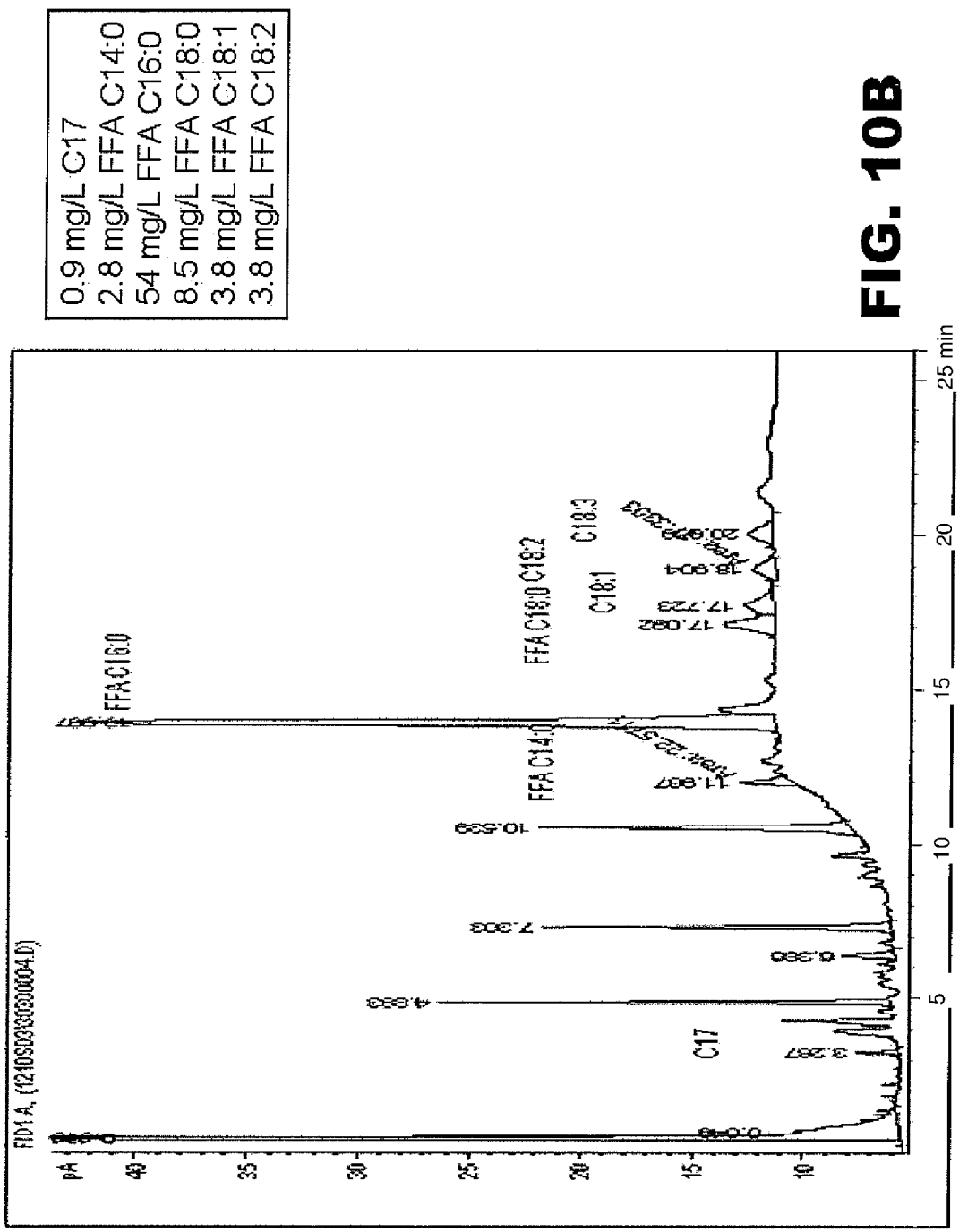

One alkane overprodution strain SD303 (P$_{cmp43}$::fol RBS shl Δ(slr1993-slr1994)-14::P$_{psbA210}$ aac P$_X$adc Δsll1951-15:: P$_{psbA210}$ orf1593 orf1594) was constructed on the base of a Green Recovery strain SD237, by overexpressing the alkane biosynthesis genes from *Nostoc punctiorme* PCC 73102 and *Synechococcus* sp. PCC 7942. The experiment showed that this strain is able to produce alkanes and undergo Green Recovery when induced by $CO_2$ limitation. As shown in FIG. 10, a culture of SD303 was grown to a cell density of $3 \times 10^8$ cells/ml, GC analysis showed that 0.17 mg/L of heptadecane was detected in the culture medium. After Green Recovery induced by $CO_2$ limitation for 3 days, 0.9 mg/L of heptadecane were released into the culture medium, also a significant amount of free fatty acids were generated by Green Recovery (FIG. 10). This experiment showed that Green Recovery is able to release the alkanes which are retained inside the cell, and also to produce free fatty acids for biofuel production.

What is claimed is:

1. A photosynthetic microorganism, wherein the microorganism comprises a nucleic acid cassette comprising an inducible promoter and a constitutive promoter operably-linked to a nucleic acid encoding a thermostable lipase capable of hydrolyzing the lipid membranes of the microorganism, wherein the thermostable lipase has an optimal temperature of about 40° C. or more.

2. The photosynthetic microorganism of claim 1, wherein the microorganism is a *Synechocystis* PCC sp. 6803 cyanobacterium having ATCC #27184.

3. The photosynthetic microorganism of claim 1, wherein the inducible promoter is induced in the absence of $CO_2$.

4. The photosynthetic microorganism of claim 1, wherein the thermostable lipase is encoded by the fnl nucleic acid sequence of *Fervidobacterium nodosum*.

5. The photosynthetic microorganism of claim 1, wherein the thermostable lipase is activated at about 46° C.

6. The photosynthetic microorganism of claim 1, wherein hydrolyzing the lipid membranes of the microorganism releases the contents of the microorganism.

7. The photosynthetic microorganism of claim 6, wherein the contents of the microorganism are biofuels and biofuel precursors.

8. The photosynthetic microorganism of claim 6, wherein hydrolyzing the lipid membrane of the cyanobacterium releases FFA.

9. The photosynthetic microorganism of claim 6, wherein hydrolyzing the lipid membrane of the cyanobacterium releases neutral lipids.

10. The photosynthetic microorganism of claim 6, wherein hydrolyzing the lipid membrane of the cyanobacterium releases alkanes.

* * * * *